US012453833B2

(12) United States Patent
Kane

(10) Patent No.: US 12,453,833 B2
(45) Date of Patent: Oct. 28, 2025

(54) NASAL RESPIRATORY APPARATUS

(71) Applicant: PNEUMA THERAPEUTICS, INC., Tuscon, AZ (US)

(72) Inventor: David M. Kane, Windham, NH (US)

(73) Assignee: PNEUMA THERAPEUTICS, INC., Tuscon, AZ (US)

( * ) Notice: Subject to any disclaimer, the term of this patent is extended or adjusted under 35 U.S.C. 154(b) by 912 days.

(21) Appl. No.: 17/416,748

(22) PCT Filed: Dec. 23, 2019

(86) PCT No.: PCT/US2019/068231
§ 371 (c)(1),
(2) Date: Jun. 21, 2021

(87) PCT Pub. No.: WO2020/132664
PCT Pub. Date: Jun. 25, 2020

(65) Prior Publication Data
US 2022/0088339 A1 Mar. 24, 2022

Related U.S. Application Data

(60) Provisional application No. 62/889,639, filed on Aug. 21, 2019, provisional application No. 62/840,669, (Continued)

(51) Int. Cl.
*A61M 16/06* (2006.01)
*A61M 16/08* (2006.01)

(52) U.S. Cl.
CPC .... *A61M 16/0672* (2014.02); *A61M 16/0655* (2014.02); *A61M 16/0683* (2013.01); (Continued)

(58) Field of Classification Search
CPC .......... A61M 16/0672; A61M 16/0655; A61M 16/0683; A61M 16/0825; A61M 16/085; (Continued)

(56) References Cited

U.S. PATENT DOCUMENTS 6,799,575 B1 * 10/2004 Carter ................ A61M 16/085 128/207.18
7,036,508 B2 * 5/2006 Kwok .............. A61M 16/0683 128/206.28
(Continued)

FOREIGN PATENT DOCUMENTS

EP 2130563 A1 12/2009
FR 2958168 A1 10/2011
(Continued)

OTHER PUBLICATIONS

International Search Report and Written Opinion issued in PCT/US2019/068231, dated Mar. 2, 2020, 9 pages.
(Continued)

*Primary Examiner* — Tu A Vo
*Assistant Examiner* — Kelsey E Baller
(74) *Attorney, Agent, or Firm* — Meunier Carlin & Curfman LLC

(57) ABSTRACT

A nasal respiratory apparatus with end tidal sampling according to various implementations is intended to support providing oxygen, ventilation, and end tidal $CO_2$ sampling of the patient oxygenation during pre-operation, undergoing anesthesia intra-operation, and post-operation during recovery. Additional features of the device include an oral shield/scoop that allows for sampling of orally ventilated end tidal $CO_2$ and a bite block that allows for oral end tidal $CO_2$ sampling and opens the patient's mouth, allowing for use of an endotracheal tube, head straps, and nares ports.

19 Claims, 74 Drawing Sheets

Section B - B

Section A - A

Related U.S. Application Data filed on Apr. 30, 2019, provisional application No. 62/806,278, filed on Feb. 15, 2019, provisional application No. 62/783,747, filed on Dec. 21, 2018.

(52) U.S. Cl.
CPC ...... *A61M 16/0825* (2014.02); *A61M 16/085* (2014.02); *A61M 16/0875* (2013.01)

(58) Field of Classification Search
CPC .......... A61M 16/0875; A61M 16/0816; A61M 16/12; A61M 16/0493; A61M 16/0666; A61M 2202/0208; A61M 2210/0618; A61M 2210/0625; A61M 2230/432; A61B 5/4836; A61B 5/082; A61B 5/087; A61B 5/097; A61B 2505/05
See application file for complete search history.

(56) References Cited

U.S. PATENT DOCUMENTS

| | | | | |
|---|---|---|---|---|
| 7,500,482 | B2 * | 3/2009 | Biederman | A61M 16/085 600/532 |
| 7,946,288 | B2 | 5/2011 | Flynn et al. | |
| 8,443,807 | B2 * | 5/2013 | McAuley | A61M 16/0683 128/207.18 |
| 8,844,529 | B2 | 9/2014 | Selvarajan et al. | |
| 9,205,215 | B2 * | 12/2015 | McAuley | A61M 16/06 |
| 2004/0129273 | A1 | 7/2004 | Hickle | |
| 2007/0068535 | A1 * | 3/2007 | Colman | A61B 90/16 128/859 |
| 2007/0240721 | A1 * | 10/2007 | Ho | A61M 16/0825 128/207.13 |
| 2008/0230067 | A1 * | 9/2008 | Kwok | A61M 16/0683 128/207.18 |
| 2009/0173350 | A1 | 7/2009 | Swanson | |
| 2010/0000534 | A1 * | 1/2010 | Kooij | A61M 16/0616 128/207.13 |
| 2010/0113956 | A1 | 5/2010 | Curti et al. | |
| 2011/0265796 | A1 * | 11/2011 | Amarasinghe | A61M 16/0683 128/206.28 |
| 2014/0018691 | A1 | 1/2014 | McNeill et al. | |
| 2015/0314098 | A1 | 11/2015 | Allum et al. | |
| 2016/0213281 | A1 * | 7/2016 | Eckerbom | A61B 5/097 |
| 2016/0220777 | A1 | 8/2016 | Weaver et al. | |
| 2016/0228035 | A1 | 8/2016 | Poormand et al. | |
| 2017/0007795 | A1 * | 1/2017 | Pedro | A61B 5/082 |
| 2017/0203070 | A1 * | 7/2017 | Lei | A61M 16/0666 |
| 2018/0078726 | A1 * | 3/2018 | Barraclough | A61M 16/0495 |

FOREIGN PATENT DOCUMENTS

| | | | | |
|---|---|---|---|---|
| WO | WO-2015156690 | A1 * | 10/2015 | A61M 16/0009 |
| WO | 2015193833 | A2 | 12/2015 | |

OTHER PUBLICATIONS

Extended European Search Report, dated Aug. 10, 2022, received in connection with corresponding EP Patent Application No. 19901160.2.

* cited by examiner

2800

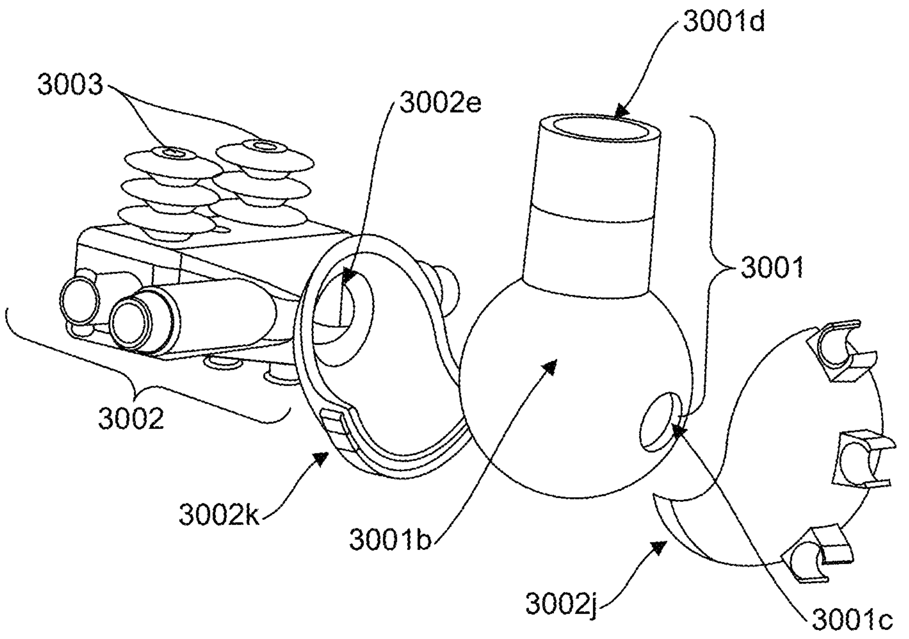
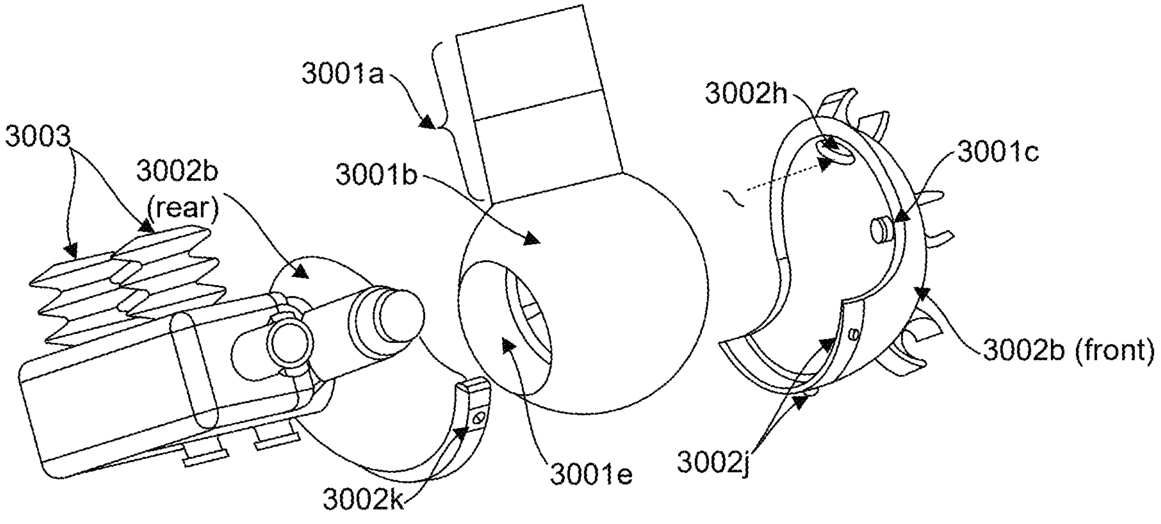
FIG. 31

Section A-A
2 Air Chamber Assembly

1. Strap pulled in Z’ direction relative to Halo assembly
2. Foam Compression Spring $K_F$ compressed by $\Delta Z$ ($Z_2 - Z_1$)
3. Left & Right portion of strap secured to Reaction Plate by looping strap hole to left and right Head Strap Connector
4. Left & Right portion of strap now in tension
5. Total force on Reaction Plate, $K_F \times \Delta Z = -F_1 - F_2$
6. Total Force on NOVA Et, $-K_F \times \Delta Z = F_1 + F_2$

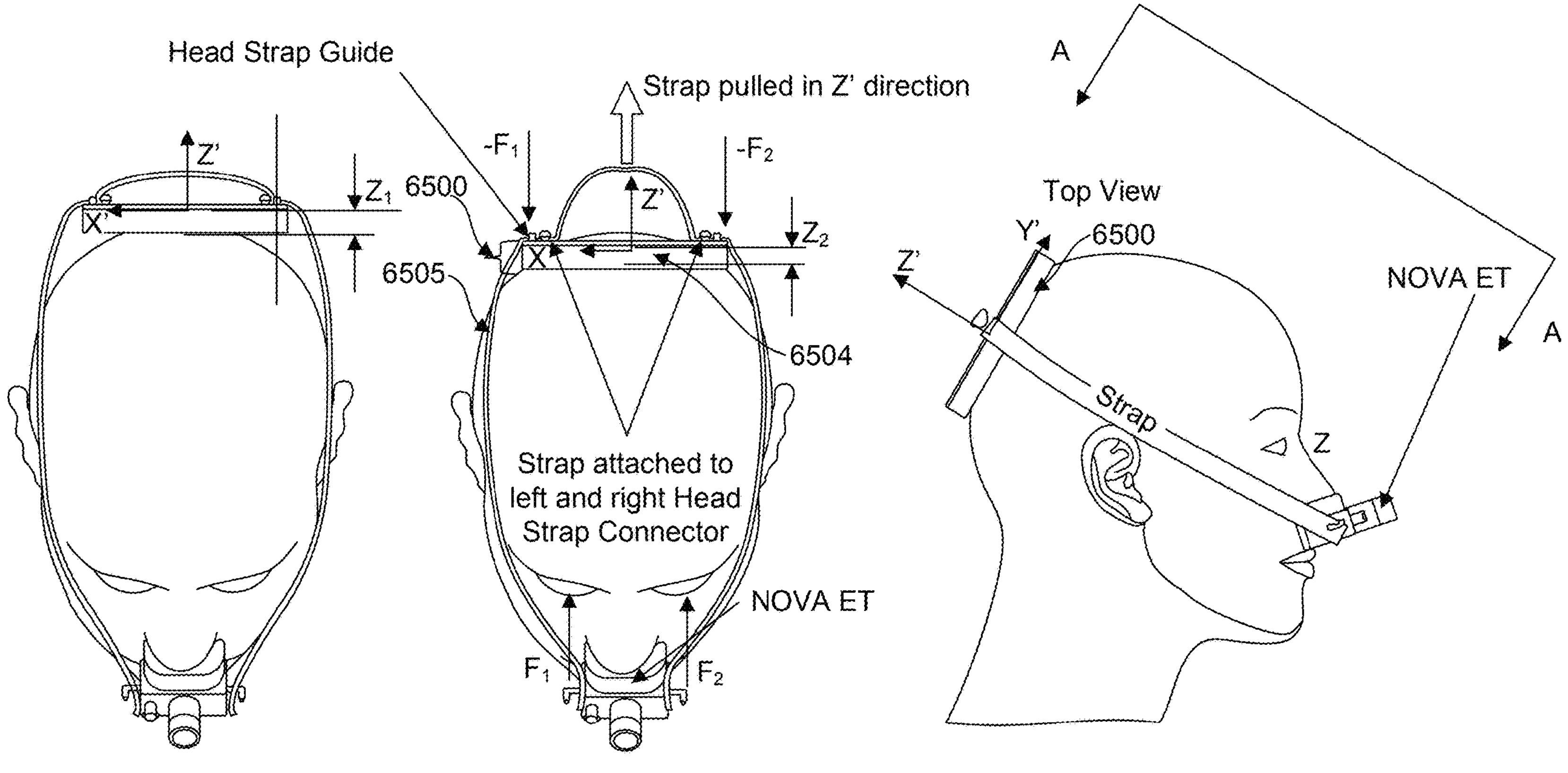

View A – A
Halo Placed Behind Head

View A – A
Strap Secured

Right Side View
Strap Secured

FIG. 67

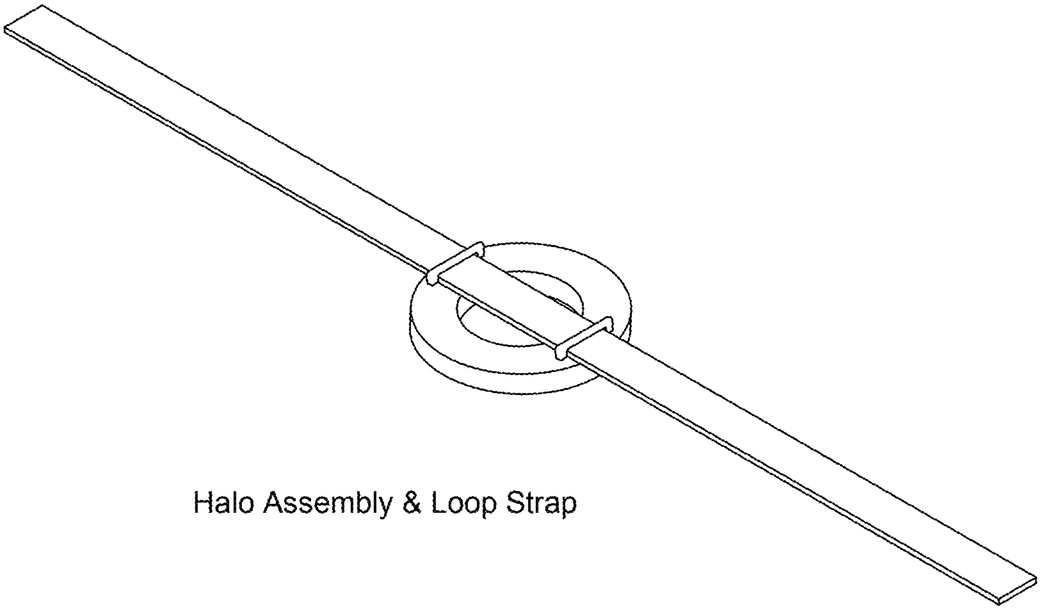
Halo Assembly & Loop Strap
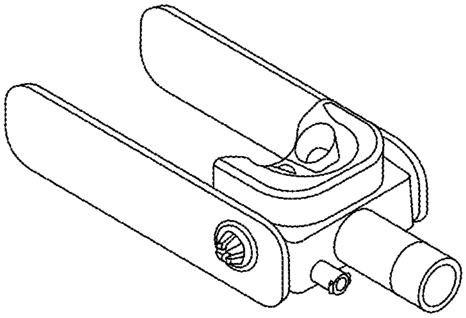
N-Vent™ Device with Hook Straps
FIG. 70

NASAL RESPIRATORY APPARATUS

This is a national stage application filed under 35 U.S.C. § 371 of International PCT Patent Application No. PCT/US2019/068231, filed Dec. 23, 2019, entitled "NASAL RESPIRATORY APPARATUS," which claims priority to U.S. Provisional Patent Application No. 62/783,747, filed Dec. 21, 2018; U.S. Provisional Patent Application No. 62/806,278, filed Feb. 15, 2019; U.S. Provisional Patent Application No. 62/840,669, filed Apr. 30, 2019; and U.S. Provisional Patent Application No. 62/889,639, filed Aug. 21, 2019, which applications are hereby incorporated by this reference in their entireties.

BACKGROUND

Field

Embodiments of the present invention relate to oxygenation, ventilation and end tidal CO2 sampling during general anesthesia and deep sedation, and specifically to a nasal mask with various related features.

Background

General anesthesia has historically utilized a full-face mask attached to an anesthesia machine to support providing anesthetic gases and oxygen, as well as ventilating the patient and monitoring exhaled end tidal $CO_2$ levels. A major issue with using a full-face mask is that the mask must be removed for oral access to place an intubation tube, resulting in an apenic period. Respiratory compromise is a common result from the apenic period for high-risk patients.

Given the trend for more minimally invasive procedures, the use of intravenous deep sedation has grown significantly. Nasal cannula are used providing nasal oxygenation, but don't provide pressurization, sometimes resulting in respiratory compromise if the nasal pharynx becomes blocked.

To address the shortcomings of full-face masks and nasal cannula, nasal ventilation masks covering the nose and sealing against the face are becoming popular. nasal ventilation masks support pressurization required to overcome blockage of the nasal pharynx, but obstruct the region near the eyes, easily lose a seal if the mask is tilted or if there is facial hair such as a mustache is present.

A nasal respiratory apparatus according to principles described herein and its various embodiments and combinations of features addresses the major shortcomings of all three of these approaches, supporting pressurized oxygenation, ventilation and end-tidal CO2 sampling via nasal ventilation system that seals via the nares and nasal vestibule. This results in a more secure seal. The device is much more compact an unobtrusive than either mask approach, allowing for oral and eye access if required.

BRIEF SUMMARY OF THE DISCLOSURE

Accordingly, the present invention is directed to nasal respiratory apparatus that obviates one or more of the problems due to limitations and disadvantages of the related art.

In accordance with the purpose(s) of an invention, as embodied and broadly described herein, this invention, in one aspect, relates to a nasal respiratory apparatus comprising an air chamber having a gas connection port, at least one nasal conduit, a nasal end tidal sample port, wherein the gas connection port is configured to receive an externally supplied gas via a gas supply tube; the at least one nasal conduit in fluid communication with the gas connection port, and the nasal end tidal sample port in fluid communication with the at least one nasal conduit for receiving sample nasal gas from the at least one nasal conduit and cause the sample nasal gas to exit the air chamber.

In another aspect, the air chamber comprises a removable end cap, the end cap comprising at least one wall of the air chamber.

In yet another aspect, the air chamber includes an isolation wall, the isolation wall substantially separating the externally supplied gas from the sample nasal gas in the air chamber.

In yet another aspect, an oral end tidal scoop may be removably connected to the air chamber, the oral end tidal scoop having an oral end tidal sampling port.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

In an aspect, inhaled gas flows from the external gas supply through the gas supply tube through the gas connection port into the air chamber and through the nasal conduit to the patient's nares; and exhaled gas flows from the patient's nares through the nasal conduit into the air chamber and through the gas connection port through the gas supply tube and through the nasal conduit into the air chamber and to the nasal end tidal sample port.

If an oral end tidal scoop is provided, exhaled gas flows from the patient's mouth into the oral end tidal scoop and to the oral end tidal sample port.

Further embodiments, features, and advantages of the nasal respiratory apparatus, as well as the structure and operation of the various embodiments of the nasal respiratory apparatus, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate the nasal respiratory apparatus. Together with the description, the figures further serve to explain the principles of the nasal respiratory apparatus described herein and thereby enable a person skilled in the pertinent art to make and use the nasal respiratory apparatus.

FIG. 31 is an exploded view of an articulated nasal respiratory apparatus.

FIG. 67 illustrates foam compression and resulting Reactive Forces on the halo assembly.

FIG. 70 illustrates a hook and loop strap configuration.

DETAILED DESCRIPTION

Reference will now be made in detail to embodiments of the nasal respiratory apparatus with reference to the accompanying figures. The same reference numbers in different drawings may identify the same or similar elements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Throughout this application, various publications may have been referenced. The disclosures of these publications in their entireties are hereby incorporated by reference into this application in order to more fully describe the state of the art to which this invention pertains.

Figure 1:
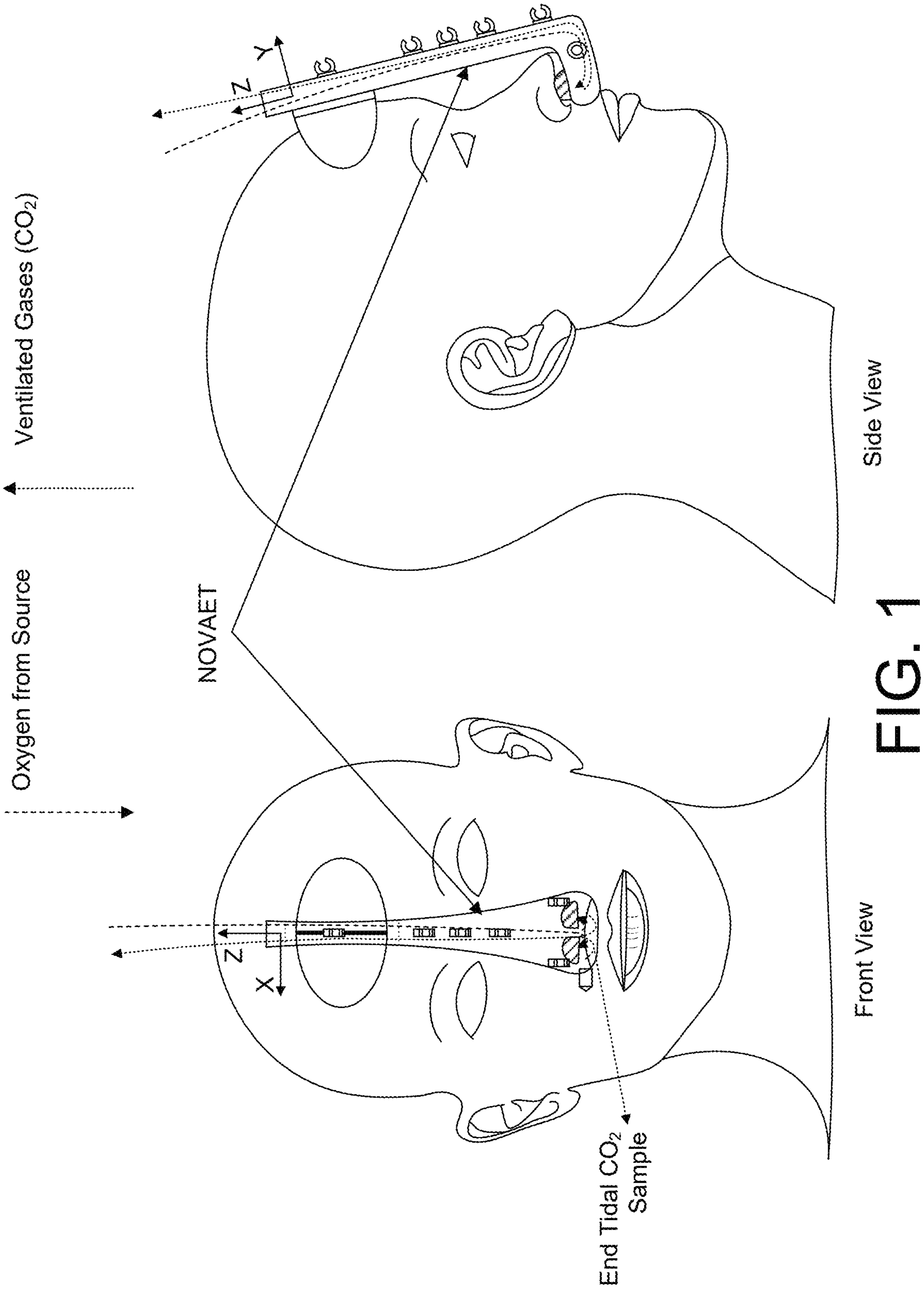
FIG. 1 illustrates a nasal respiratory apparatus according to principles described herein.
Figure 2:
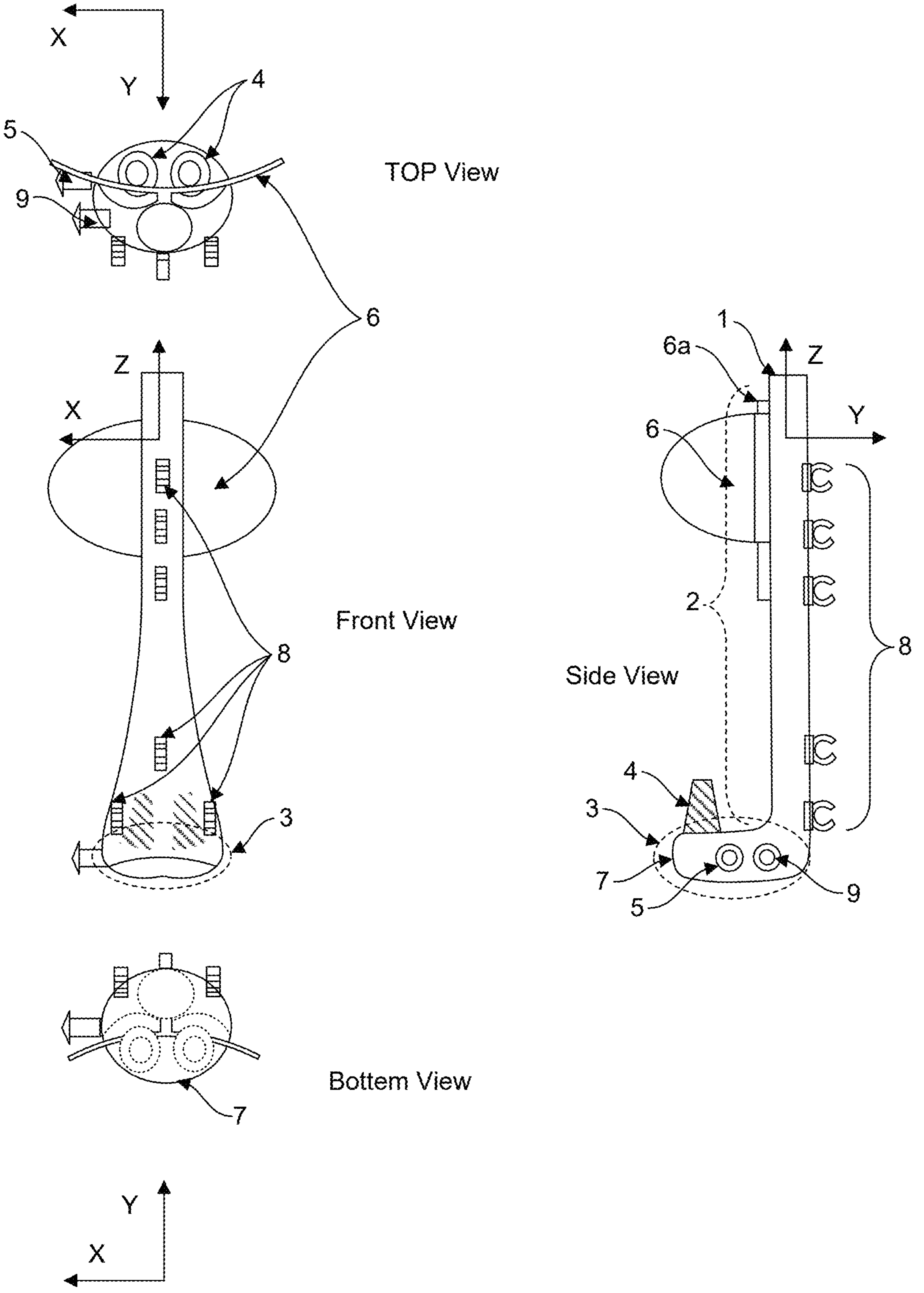
FIG. 2 illustrates a nasal respiratory apparatus according to principles described herein.

Oxygenation, ventilation and end tidal CO2 sampling of a patient with an embodiment of a nasal respiratory apparatus according to principles described herein is illustrated in FIG. 1. Elements of the nasal respiratory apparatus, including an optional end tidal (ET) $CO_2$ sample port 5 are illustrated in FIG. 2. As illustrated in FIG. 2, a gas port connection 1 provides interface with standard $O_2$ source, anesthesia machine, hyper-inflation bag, high-flow source or ventilator. The port 1 may include 8.5 mm, 11.5 mm, 15 mm or 22 mm conical connectors as defined by ISO 5356 or current equivalent standard. Other connector interfaces are possible. This port 1 may be designed to fit male or female connectors. A male connection interface is shown in FIG. 2 for the purposes of illustration.

As shown if FIG. 2, a gas supply tube 2 is a conduit containing and allowing for the flow of gas between a gas connection port 1 and the air chamber 3. The gas supply tube 2 can either be rigid or expandable. Being expandable will accommodate for different size heads and allow the tubing to expand and retract as patients move head up and down, side to side, or rotate. Air chamber 3 provides a structural and gas flow interface between the gas supply tube 2, nares ports 4 and an end tidal sampling port 5. There may be one or two nares port 4 to provide the mechanical and gas flow interface between the nares and the nasal respiratory apparatus. An outer portion of the nares port 4 provides a pressure seal in order to contain airflow between the nasal pharynx and the nasal respiratory apparatus.

The end tidal sample port 5 is an optional interface allowing for sampling the level or make up of the end tidal $CO_2$, end tidal $O_2$, or other nasally exhaled gas of interest via by a sampling device such as a Capnography Sensor, an oxygen sensor, gas analyzer or the like. The port exterior may be a standard luer lock connector that interfaces with a sampling line per ISO 80396-7: 2016(E) or current equivalent. A male or female connector can be implemented; a female interface is shown for the purposes of illustration. Alternate interfaces can be used. The end tidal sample port 5 can be on the plus or minus X-axis side of the air chamber 3.

A forehead standoff 6 may be provided to provide a cushioned mechanical interface between the nasal respiratory apparatus and the patient's forehead. Additionally, the forehead standoff 6 provides space between the gas supply tube 2 and the patient's forehead, allowing various connectors to connect to the gas supply tube 2 without interference from the forehead.

A rail 6*a* may be used in an optional configuration where the rail 6*a* is part of the gas supply tube 2. In this configuration, the forehead standoff 6 may be separate from the gas supply tube 2, constrained by the rail 6*a* in the X and Y directions, but can slide along the Z-axis, allowing the forehead standoff 6 to be centered on the forehead. This allows the nasal respiratory apparatus to accommodate a wide range of patient head sizes. The gas supply tube 2 can either be rigid or expandable. Being expandable will accommodate for different size heads and allow the tubing to expand and retract as patients move head up and down, side to side, or rotate.

A *Columella-Philtrum* to nasal respiratory apparatus interface 7 is a cushioned mechanical interface between the nasal respiratory apparatus and the patient's *Columella-Philtrum* region.

Head strap connectors 8 provide mechanical tie points 10 between the nasal respiratory apparatus and at least one head strap (not shown) that secures the nasal respiratory apparatus to the patient's head. Strap tie points 10 are illustrated in FIG. 2 for attachment of retention straps, to be described later. The head strap connector 8 side view may be nominally C-shaped in order to clamp around the head strap cord/band once the cord/band is snapped in place.

A supplementary $O_2$ port 9 may extend from the air chamber 3. The supplementary $O_2$ port 9 interfaces with an oxygen supply line (not shown) and allows for additional oxygen to be provided to the patient via a wall or other oxygen supply source (not shown). Note the supplementary $O_2$ port 9 can be on the plus or minus X-axis side of the air chamber.

Strap tie points 10 are also illustrated in FIG. 2 for attachment of retention straps, to be described later.

During the inhalation portion of the breathing cycle, pressurized gases (i.e., Oxygen ($O_2$), air anesthetic agents etc.) are provided by a source (wall $O_2$ supply, bottled $O_2$ supply, ventilation machine, anesthesia machine continuous positive airway pressure (CPAP) machine, bilevel positive airway pressure machine (BiPAP) or another device). It enters the, bilevel positive airway pressure machine via a gas connection port 1, travels through the gas supply tube 2 and the air chamber 3 finally flowing out the nares ports 4. gas leaves the nares ports 4, traveling through the patient's nasal pharynx and eventually reaches the patient's lungs, where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares ports 4, traveling through the air chamber 3, the gas supply tube 2 and out the gas connection port 1. A small amount of ventilated gas (i.e., carbon dioxide $CO_2$), oxygen, anesthetic gases, etc.) can be sampled out of the end tidal sample port 5 by a monitoring device (not shown).

Figure 3:
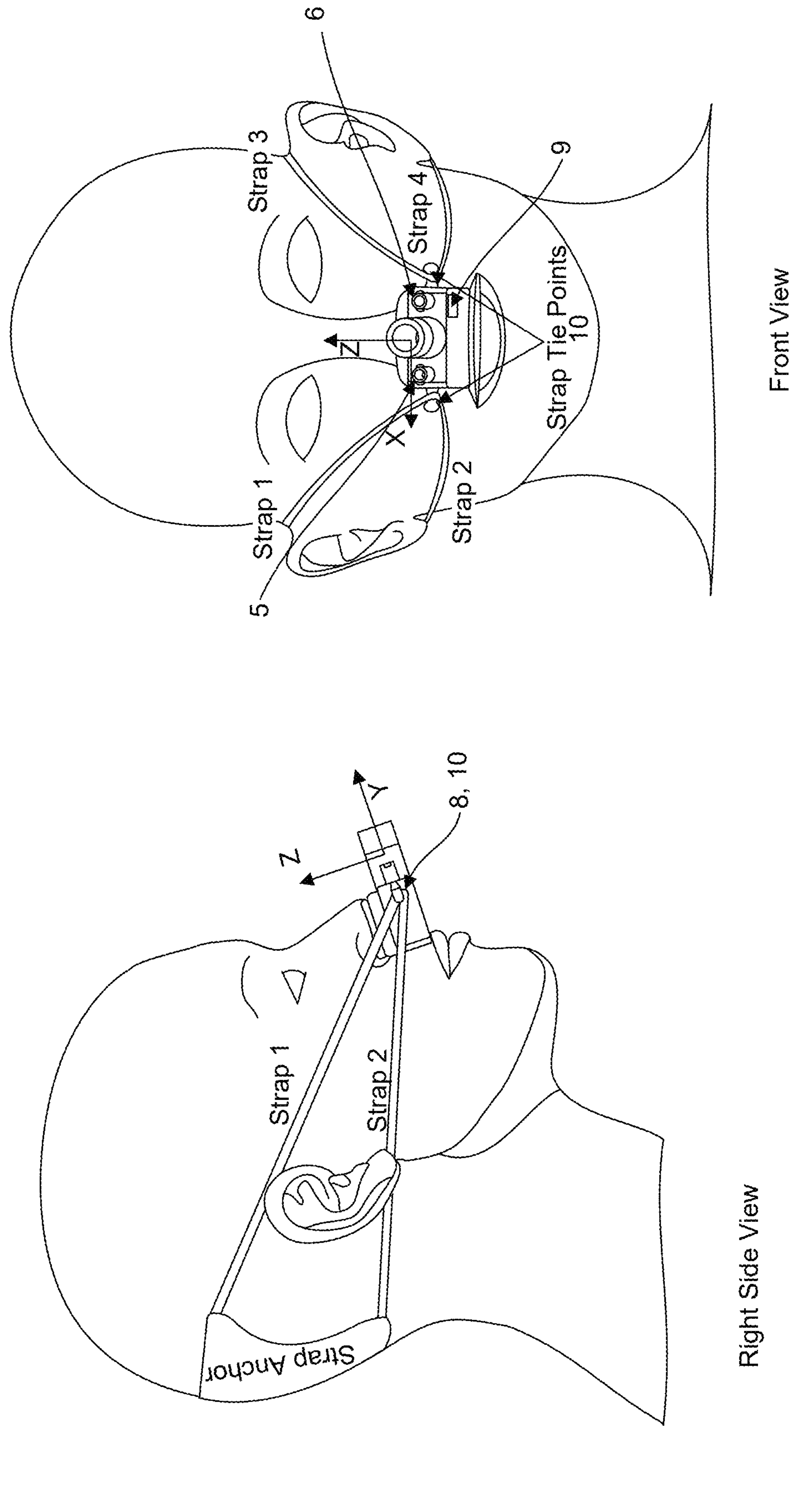
FIG. 3 illustrates a nasal respiratory apparatus according to principles described herein with nasal and oral end tidal sampling ports.

A coordinate system is used in explaining various embodiments. A right-handed X, Y, Z-axis Cartesian Coordinate system is illustrated in and referred to with respect to the features illustrated in FIGS. 3, 4 and 5. As illustrated, the, bilevel positive airway pressure machine has a gas connection port 401 parallel to the Y-axis, although the port could be parallel to the X or Z-axis. In certain circumstances, the Y-axis configuration may be advantageous over the Z-axis configuration for patient access for different types of procedures in that it can be used with the patient in a supine position (laying on the back) or lateral position with the patient lying on the left or right side.

Figure 4:
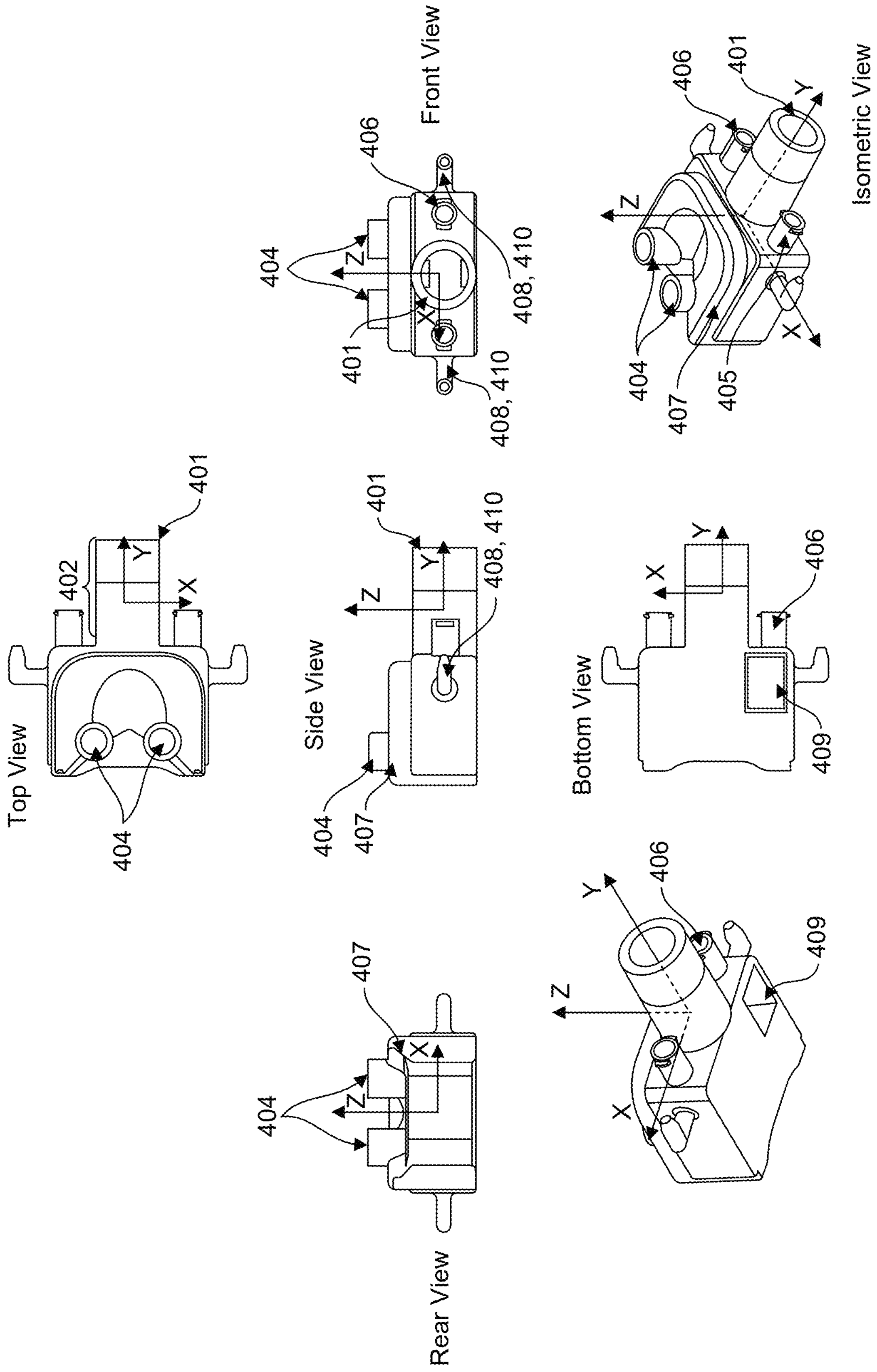
FIG. 4 illustrates a nasal respiratory apparatus according to principles described herein.

Elements of the nasal respiratory apparatus configuration with the gas connection port 401 parallel to the Y-axis are illustrated in FIG. 4. Referring to FIG. 4, gas connection port 401 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible. This port 401 is designed to fit male or female connectors. A male connection interface is shown on this illustration. Note the gas connection port or gas port connection 401 can be located in either the plus or minus direction in an orientation with its axis parallel to the X, Y or Z-axis.

gas supply tube 402 is a conduit containing and allowing for the flow of gas between the gas connection port 401 and air chamber 403. The gas supply tube 402 can either be rigid or expandable. Being expandable will accommodate for different size heads and allow the tubing to expand and retract as patients move head up and down, side to side, or rotate. Air chamber 403 provides the structural and gas flow interface between the gas supply tube 402, at least one nares port(s) 404 and the end tidal sampling port 405. The one or two nares ports 404 provide the mechanical and gas flow interface between the patient's nares and the nasal respiratory apparatus.

The nasal end tidal sample port 405 is parallel to the Y-axis and is an optional interface allowing for sampling of end tidal $CO_2$, end tidal $O_2$, or other nasally exhaled gas of interest via by a sampling device (not shown) such, etc. such as a Capnography Sensor, an oxygen sensor, or gas analyzer. The port exterior is a standard luer lock connector that interfaces with a sampling line per ISO 80396-7: 2016(E) or current equivalent. A male or female connector can be implemented, a female interface is shown in the illustration. Alternate interfaces can also exist. The end tidal port 405 can be on the plus or minus X-axis side of the air chamber. The end tidal port being along the X, Y or Z-axis and on the +/−X side or +/−Z side and +Y side is also possible. The nasal and oral end tidal sample ports 405/406 can be connected individually to a sample line of a gas monitoring device (not shown), or can both be connected to the same gas sample line via a Y flow connector (not shown).

The oral end tidal sample port 406 parallel to the Y-axis is an interface allowing for sampling composition or levels of the oral end tidal $CO_2$, end Tidal $O_2$, etc. exhaled orally by a sampling device (not shown) such as a Capnography Sensor, an oxygen sensor, or gas analyzer. The port exterior is a standard luer lock connector that interfaces with a sampling line per ISO 80396-7: 2016(E) or current equivalent. A male or female connector can be implemented; a female interface is shown for purposes of illustration. Alternate interfaces can also exist. The end tidal sample port 406 can be on the plus or minus X or Z-axis side of the air chamber 403. The nasal and oral end tidal sample ports 405/406 can be connected individually to the sample line of a gas monitoring device (not shown), or can both be connected to the same gas sample line via a Y flow connector (not shown).

A nasal dam 407 may surround the nares ports 404 and interfaces with the soft tissue of the nasal base, providing a pressure seal in order to contain airflow between the nasal pharynx and the nasal respiratory apparatus.

Head strap connectors 408 provide mechanical tie points 410 between the nasal respiratory apparatus and a head strap (not shown) that secures the nasal respiratory apparatus to the patient's head. An oral ventilation scoop 409 may be located below the air chamber 403, near the mouth of the patient. The scoop 409 may be substantially isolated from the air chamber 403 from a gas pressure and flow perspective. The scoop 409 may be common to the oral end tidal sample port 406. In such configuration, when gas is expelled from the mouth, a portion flows into the oral ventilation scoop 409 to the oral end tidal sample port 406 and onto a gas monitoring device (not shown) if it is connected by a sample line (not shown).

During the inhalation portion of the breathing cycle, pressurized gases (i.e. Oxygen ($O_2$), air anesthetic agents etc.) are provided by a source (wall $O_2$ supply, bottled $O_2$ supply, ventilation machine, anesthesia machine continuous positive airway pressure (CPAP) machine, bilevel positive airway pressure (BiPAP) or another device). It enters the nasal respiratory apparatus via the gas connection port 401, travels through the gas supply tube 402 and the air chamber 403 finally flowing out the nares port(s) 404. gas leaves the nares port(s) 404, traveling through the patient's nasal pharynx and eventually reaches the patient's lungs, where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares port(s) 404, traveling through the air chamber 403, the gas supply tube 402 and out the gas connection port 401. A small amount of ventilated gas (i.e., carbon dioxide ($CO_2$), oxygen, anesthetic gases, etc.) can be sampled out of the nasal end tidal sample port 405/406 by a monitoring device. If the patient exhales orally, gas from the mouth enters the oral ventilation scoop 409 and enters the oral end tidal sample port 406. Both the nasal and oral end tidal sample ports 405/406 are connected either separately, or through a Y connector (not shown) to a common sample line attached to a gas monitoring device.

Figure 5:
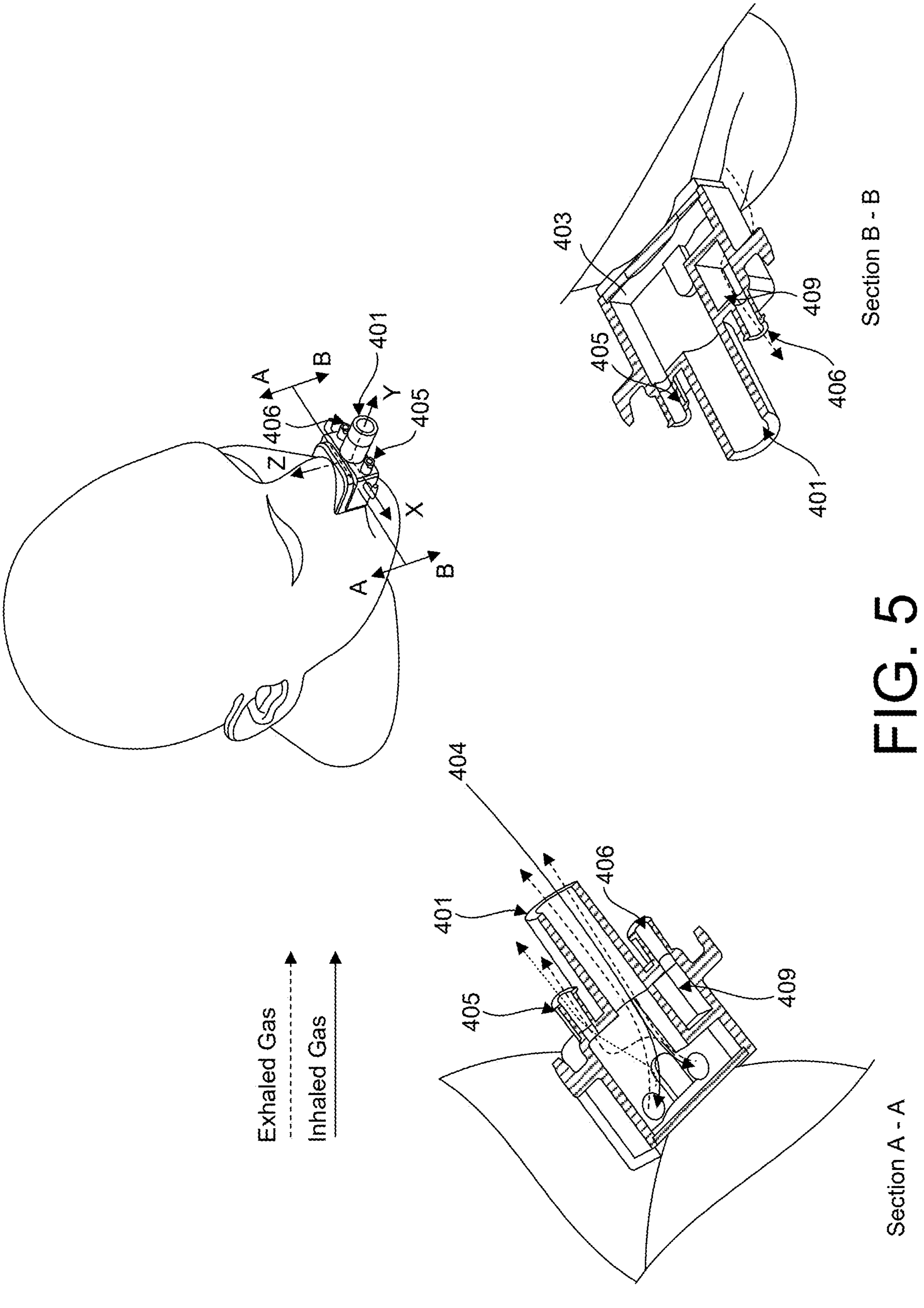
FIG. 5 illustrates cross-sectional views of illustrates a nasal respiratory apparatus according to principles described herein with nasal and oral end tidal sampling ports.

The present embodiment allows for sampling of $CO_2$ or other gases that are exhaled nasally and or orally. FIG. 5 shows cross-sections A-A and B-B of the nasal respiratory apparatus device. As illustrated, the gas connection port 401, nares port(s) 404 and nasal end tidal sample port 405 are all common to the air chamber 403. The oral ventilation scoop 409 provides an opening below the air chamber 403, near the mouth opening, and the flow path is substantially isolated from the air chamber 403, but is common to the oral end tidal sampling port 406. During the inspiratory portion of a breathing cycle, external gas enters the gas connection port 401 into the air chamber 403, where it then leaves the air chamber 403 through the nares port(s) 404, entering the nasal pharynx and ultimately into the lungs. This phase is illustrated by FIG. 5, Section A-A. During the expiratory phase of the breathing cycle, exhaled gasses can leave the lungs nasally, orally or both. If the gas leaves nasally, as illustrated in FIG. 5, Section A-A, gas flows out the gas connection port 401 and a portion also flows out the nasal end tidal sample port 405, which may be attached to a gas monitoring device (not shown). Alternatively, the nasal end tidal sample port 405 may be plugged or capped (not shown). If the gas leaves orally as illustrated in FIG. 5, Section B-B, gas flows out the mouth and a portion also flows into the oral ventilation scoop 409 and into the oral end tidal sample port 406, which may be attached to a gas monitoring device (not shown). Alternatively, the oral end tidal sample port may be plugged or capped (not shown). It is possible that gases are exhaled from both the nose and the mouth, in which case they could be sampled via the associated nasal and oral end tidal sample ports 405/406.

Figure 6:
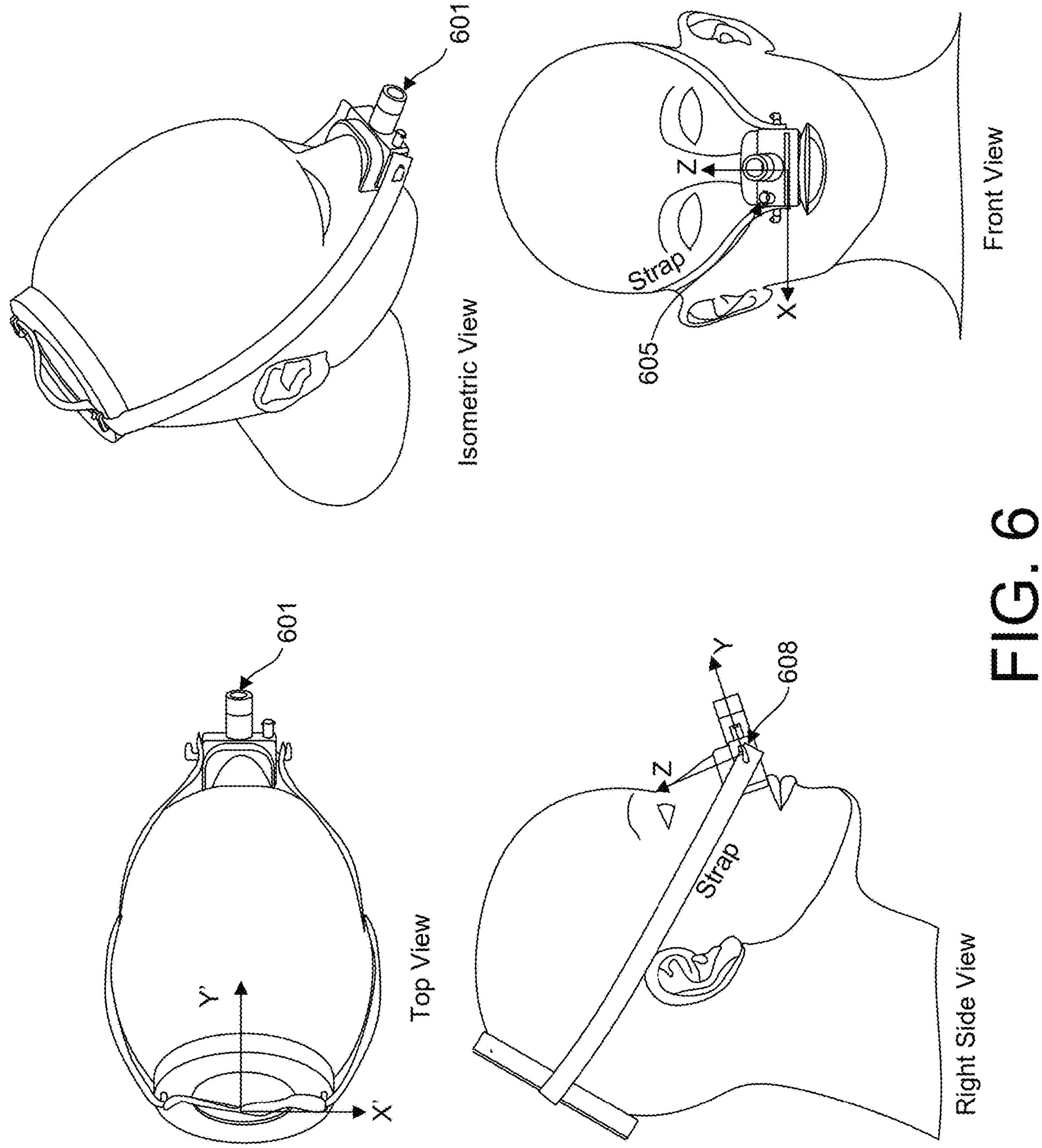
FIG. 6 illustrates a nasal respiratory apparatus with head strap according to principles described herein.
Figure 7:
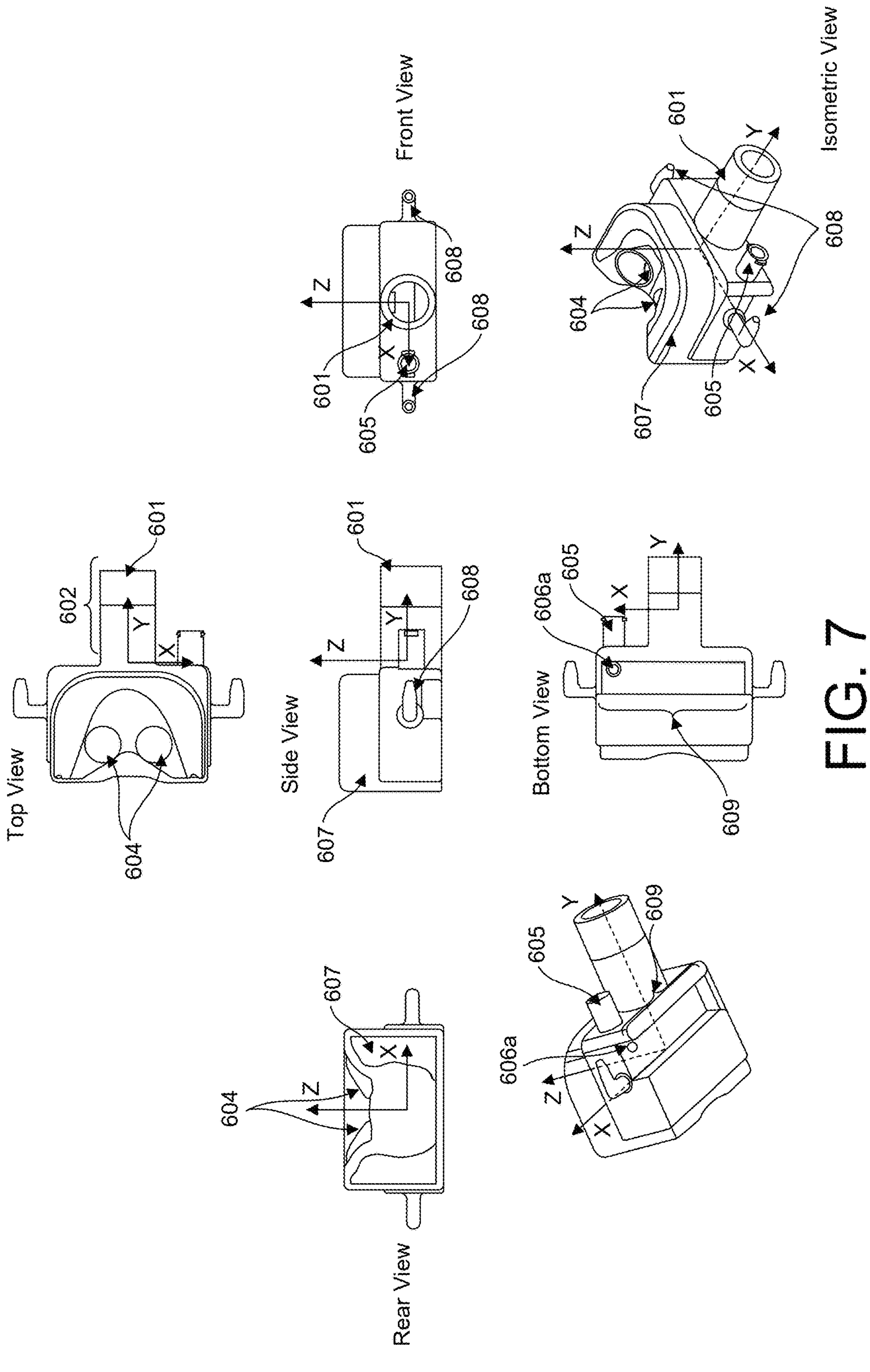
FIG. 7 illustrates a nasal respiratory apparatus according to principles described herein with nasal and oral end tidal sampling ports
Figure 8:
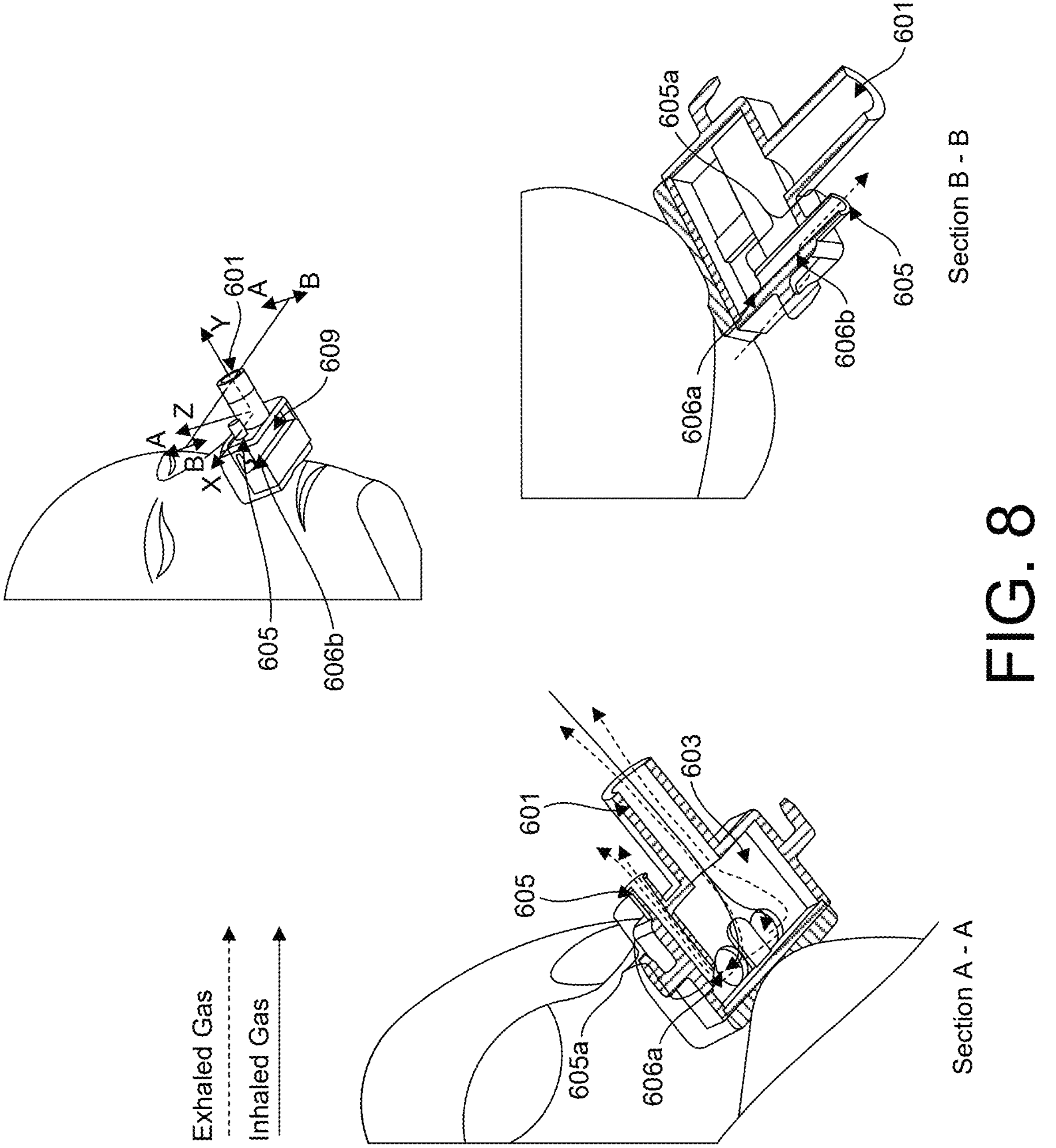
FIG. 8 illustrates cross-sectional view of a nasal respiratory apparatus according to principles described herein with nasal and oral end tidal sampling ports with combined nasal/oral end tidal sample port.

A right-handed X, Y, Z-axis Cartesian Coordinate system is illustrated in and referred to with respect to the features illustrated in FIGS. 6, 7 and 8. An embodiment of the nasal respiratory apparatus to be described are configured to have a gas connection port parallel to the Y-axis, FIG. 6, although the port could be parallel to the X or Z-axis, FIG. 7. This configuration may be advantageous over the Z-axis configuration for patient access for different types of procedures in that it can be used with the patient in a supine position (laying on the back) or lateral position with the patient lying on the left or right side.

Elements of the nasal respiratory apparatus configuration with the gas connection port 601 parallel to the Z-axis are illustrated in FIG. 7. During the inhalation portion of the breathing cycle, pressurized gases (i.e., Oxygen ($O_2$), air anesthetic agents etc. are provided by a source (wall $O_2$ supply, bottled $O_2$ supply, ventilation machine, anesthesia machine continuous positive airway pressure (CPAP) machine, bilevel positive airway pressure (BiPAP) machine or another device)). Administered gas enters the nasal respiratory apparatus via the gas connection port 601, travels through the gas supply tube 602 and the air chamber 603, finally flowing out at least one nares port 604. gas leaves the nares port(s) 604, traveling through the patient's nasal pharynx and eventually reaches the patient's lungs, where it is absorbed into the blood stream. During the exhalation portion of the breathing cycle, waste $CO_2$ and unabsorbed gases are expelled from the lungs by pressure created by the diaphragm and ventilated in the opposite direction out of the lungs, through the nares port(s), traveling through the air chamber 603, the gas supply tube 602 and out the gas connection port 601. A small amount of ventilated gas (i.e., carbon dioxide ($CO_2$), oxygen, anesthetic gases, etc.) can be sampled out of the single nasal/oral end tidal sample port 605 by a monitoring device (not shown). If the patient exhales orally, gas from the mouth enters the oral ventilation scoop 609 and enters the nasal/oral end tidal sample port 605. The combined nasal and oral end tidal sample port 605 is connected to a sample line (not shown) attached to a gas monitoring device (not shown). Alternatively, if exhaled gas is not to be sample, one or both of the end tidal sample ports may be plugged or capped.

gas connection port 601 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. gas connection port 601 can be located in either the plus or minus direction in an orientation with its axis parallel to the X, Y or Z-axis. gas supply tube 602 is a conduit containing and allowing for the flow of gas between the gas connection port 601 and the air chamber 603. The gas supply tube 602 can either be rigid or expandable. Being expandable will accommodate for different size heads and allow the tubing to expand and retract as patients move head up and down, side to side, or rotate. Air chamber 603 provides a structural and gas flow interface between the gas supply tube 602, the nares port(s) 604 and the end tidal sampling port 605. One or two nares ports 604 provide the mechanical and gas flow interface between the patient's nares and the nasal respiratory apparatus.

The nasal/oral end tidal sample port 605 parallel to the Y-axis is an optional interface allowing for sampling of the end tidal $CO_2$, end tidal $O_2$, etc. level from nasal exhalation by a sampling device such as a Capnography Sensor, an oxygen sensor, or gas analyzer. The port exterior is a standard luer lock connector that interfaces with a sampling line per ISO 80396-7: 2016(E) or current equivalent. A male or female connector can be implemented, a female interface is shown in the illustration. Alternate interfaces can also exist. Note the end tidal sample port 605 can be on the plus or minus X-axis side of the air chamber. The end tidal sample port 605 can be on the plus or minus X or Z-axis side of the air chamber.

An end tidal sample channel 605*a* has an opening into the air chamber 603 via a nasal opening 606*a* to the end tidal sample channel 605*a* and an oral ventilation scoop 609 via an oral opening 606*b* to the end tidal sample channel 605*a* where it then terminates at the port opening. $CO_2$ exhaled nasally into the air chamber 603 enters the end tidal sample channel 605*a* via the nasal opening 606*a* to the end tidal sample channel 605*a*. $CO_2$ exhaled orally into the oral ventilation scoop 609 enters the end tidal sample channel 605*a* via the oral ventilation opening 606*b* to the end tidal sample channel 605*a*. A nasal dam 607 may surrounds the nares ports 604 and interfaces with the soft tissue of the patient's nasal base, providing a pressure seal in order to contain airflow between the patient's nasal pharynx and the nasal respiratory apparatus. Head strap connectors 608 provide mechanical tie points between the nasal respiratory apparatus and a head strap that secures the nasal respiratory apparatus to the patient's head.

An oral ventilation scoop 609 is located below the air chamber 603, near the mouth. When gas is expelled from the mouth, a portion flows into the oral ventilation scoop 609 to the oral opening 606*b* to the end tidal sample channel 605*a*, out the gas connection port 601 and onto a gas monitoring device (not shown) if it is connected by a sample line (sample line).

The present configuration allows for sampling of $CO_2$ or other gases that are exhaled nasally and or orally. FIG. 8 shows cross-sections A-A and B-B of the nasal respiratory apparatus device. The gas connection port 601, nares ports 604 and nasal opening 606*a* to the nasal/oral end tidal sample port 605 are all common to the air chamber 603. The oral ventilation scoop 609 provides an opening below the air chamber 603, near the mouth opening, and the flow path is common to the nasal/oral end tidal sampling port 605 by an oral opening 606*b* to the end tidal sample port 605 closer to an interface with the end tidal sample channel 605*a* with a Luer connector. During the inspiratory portion of a breathing cycle, external gas enters the gas connection port 601 into the air chamber 603, where it then leaves the air chamber 603 through the nares port(s), entering the patient's nasal pharynx and ultimately into the lungs. This phase is illustrated by FIG. 8, Section A-A. During the expiratory phase of the breathing cycle, exhaled gasses can leave the lungs nasally, orally or both. If the gas leaves nasally as illustrated in FIG. 8, Section A-A, gas flows out the gas connection port 601 and a portion also flows out the nasal opening 606*a* to the end tidal sample channel 605*a* then out the gas connection port 601 if it is attached to a gas monitoring device (not shown). If the gas leaves orally as illustrated in FIG. 8, Section B-B, gas flows out the mouth and a portion also flows into the oral ventilation scoop 609 and into the oral opening 606*b* to the end tidal sample channel 605*a* and out the nasal/oral end tidal sample port 605 if it is attached to a gas monitoring device (not shown).

Figure 9:
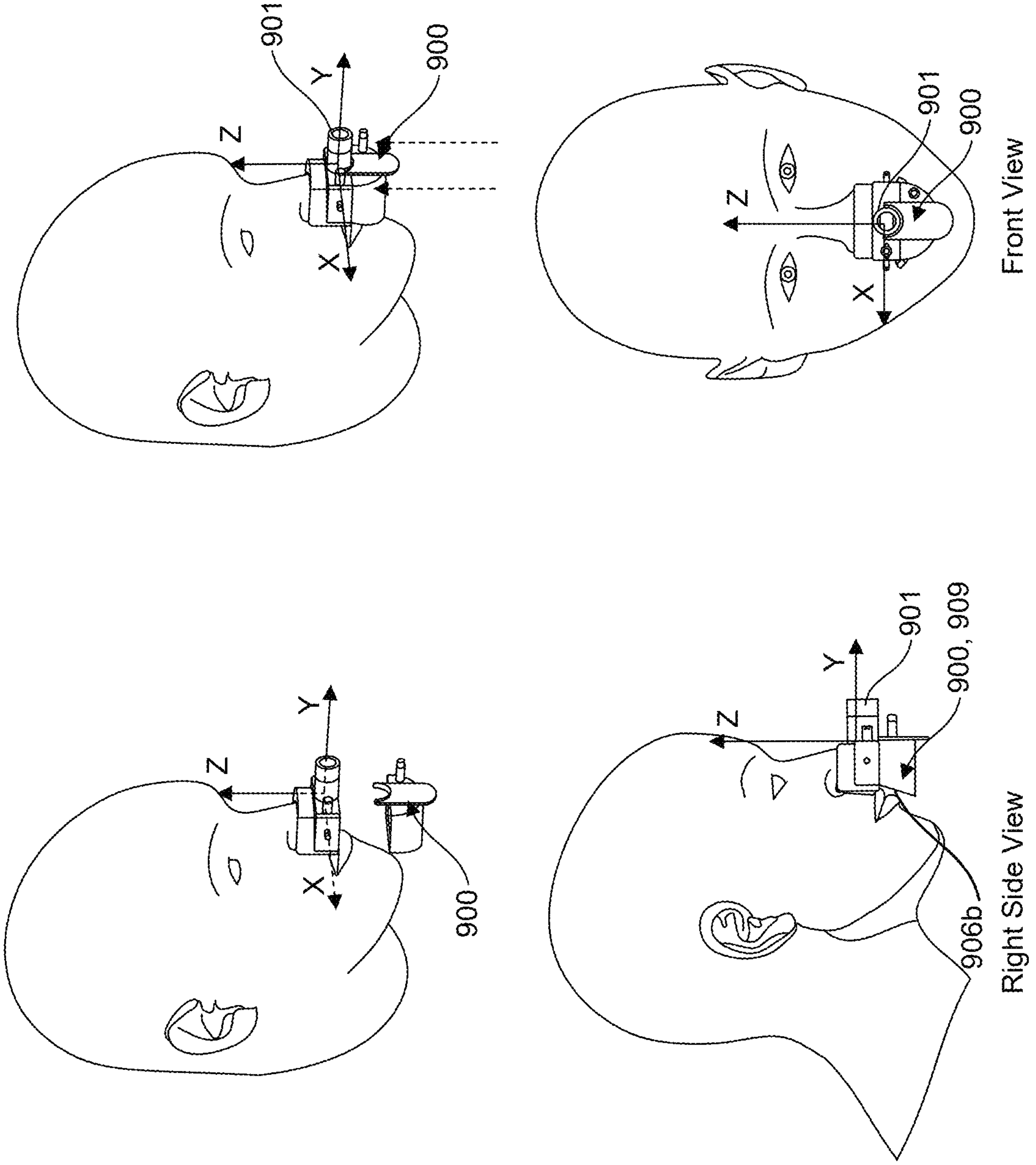
FIG. 9 illustrates a nasal respiratory apparatus according to principles described herein with nasal and oral end tidal sampling ports and end tidal ventilation scoop (gas connection port Parallel to Y-axis with Combined nasal and oral end tidal sample port).
Figure 10:
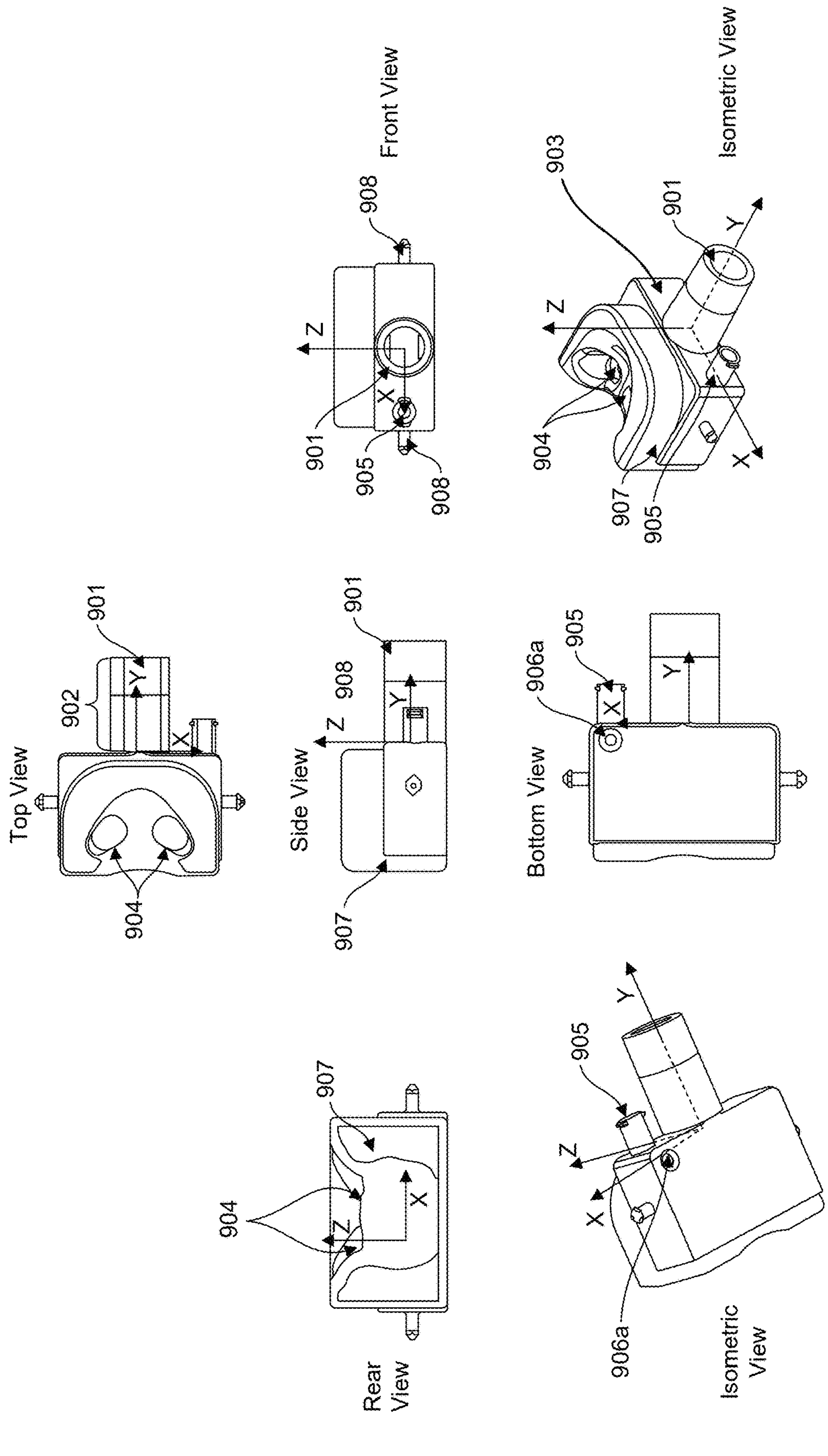
FIG. 10 illustrates a nasal respiratory apparatus according to principles described herein with nasal and oral end tidal sampling ports (gas connection port Parallel to Z-axis).

Referring to FIGS. 9 and 10, a system incorporating nasal respiratory apparatus according to principles described herein includes a gas connection port parallel to the Y-axis, FIG. 9, although the port could be parallel to the X or Z-axis.

The illustrated configuration may be advantageous over the Z-axis configuration for patient access for different types of procedures in that it can be used with the patient in a supine position (laying on the back) or lateral position with the patient lying on the left or right side. A ventilation scoop may be separate from the nasal respiratory apparatus in the system shown. The ventilation scoop may clip onto the gas connection port, as illustrated in FIG. 9. As described herein, such a clipping or modular style connection between an accessory, such as the ventilation scoop, and the gas connection port, can be used for accessories other than or in addition to a ventilation scoop.

Elements of the nasal respiratory apparatus) configuration with a gas connection port 901 parallel to the Y-axis are illustrated in FIG. 10.

Gas connection port 901 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible as well as other gas supplies, including continuous positive airway pressure (CPAP) machine and/or bilevel positive airway pressure (BiPAP) machine or another device. The gas connection port 901 is designed to fit male or female connectors. A male connection interface is shown on this illustration. The gas connection port 901 can be located in either the plus or minus direction in an orientation with its axis parallel to the X, Y or Z-axis.

A gas supply tube 902 is a conduit containing and allowing for the flow of gas between the gas connection port 901 and an air chamber 903. The gas supply tube can either be rigid or expandable. Being expandable will accommodate for different size heads and allow the tubing to expand and retract as patients move head up and down, side to side, or rotate. Air chamber 903 provides a structural and gas flow interface between the gas supply tube 902, at least one nares port 904 and an end tidal sample port 905. One or two nares ports 904 provide the mechanical and gas flow interface between a patient's nares and the nasal respiratory apparatus. A nasal/oral end tidal sample port 905 parallel to the Y-axis is an optional interface allowing for sampling of the end tidal $CO_2$, end tidal $O_2$, or other oral exhaled gas the level or composition of which is of interest, by a sampling device (not shown) such as a Capnography Sensor, an oxygen sensor, or gas analyzer. The nasal/oral end tidal sample port may be a described in relation to other embodiments of the nasal respiratory apparatus describe herein. A port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port 905 can be on the plus or minus X-axis side of the air chamber. The end tidal sample port can be on the plus or minus X or Z-axis side of the air chamber 903.

The end tidal sample channel 905*a* has an opening into the air chamber 903 via a nasal opening 906*a* to the end tidal sample channel 905*a* and an oral ventilation scoop 909 via an oral opening 906*b* to the end tidal sample channel 905*a* where it then terminates at the opening of the gas connection port 901. $CO_2$ exhaled nasally into the air chamber 903 enters the end tidal sample channel 905*a* via the nasal opening 906*a* to the end tidal sample channel 905*a*. $CO_2$ exhaled orally into the oral ventilation scoop and supplemental $O_2$ port ventilation chamber 909 enters the end tidal sample channel 905*a* via the oral ventilation chamber 909 to oral opening of the ventilation scoop 906*b*.

A nasal dam 907 may surround the nares ports and interfaces with the soft tissue of the patient's nasal base, providing a pressure seal in order to contain airflow between the patient's nasal pharynx and the nasal respiratory apparatus. Head strap connectors 908 provide mechanical tie points between the nasal respiratory apparatus and a head strap (not shown) that secures the nasal respiratory apparatus to the patient's head.

During the inhalation portion of the breathing cycle, pressurized gases (i.e., Oxygen ($O_2$)), air anesthetic agents etc.) are provided by a source (wall $O_2$ supply, bottled $O_2$ supply, ventilation machine, anesthesia machine continuous positive airway pressure (CPAP) machine, bilevel positive airway pressure (BiPAP) machine or another device). It enters the nasal respiratory apparatus via the gas connection port 901, travels through the gas supply tube 902 and the air chamber 903 finally flowing out the nares port(s). gas leaves the nares port(s), traveling through the patient's nasal pharynx and eventually reaches the patient's lungs, where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares port(s), traveling through the air chamber 903, the gas supply tube 902 and out the gas connection port 901. A small amount of ventilated gas (i.e., carbon dioxide $CO_2$, oxygen, anesthetic gases, etc.) can be sampled out of the single nasal/oral end tidal sample port 905 by a monitoring device (not shown). If the patient exhales orally, gas from the mouth enters the oral ventilation scoop 909 and enters the nasal/oral end tidal sample port 905. The combined nasal and oral end tidal sample port 905 may be connected to a sample line (not shown) attached to a gas monitoring device (not shown). Additionally, a supplemental $O_2$ port may be provided as part of the ventilation scoop 909 where the supply line from an $O_2$ source can be plugged into the $O_2$ port, providing gases orally.

Figure 11:
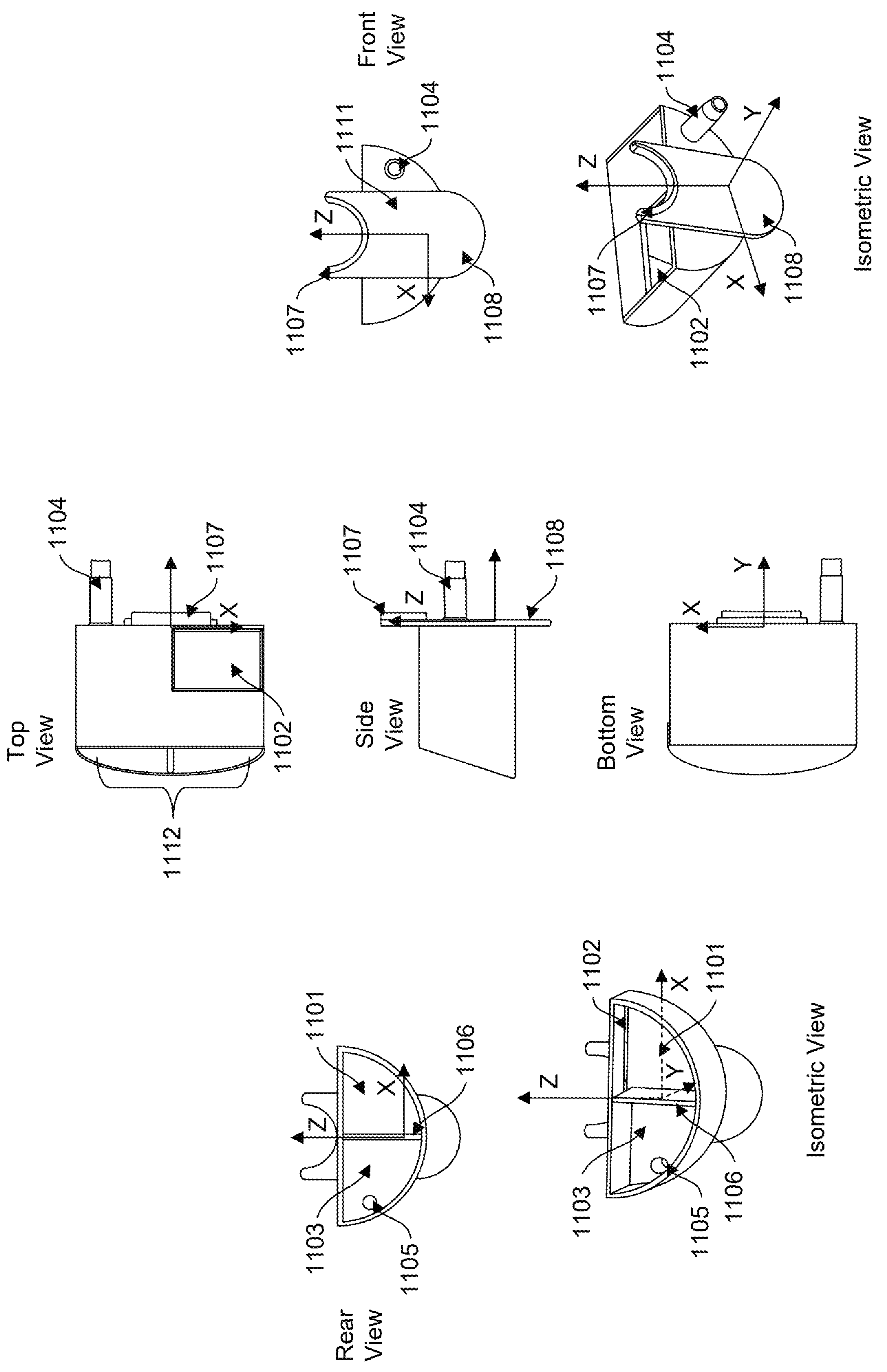
FIG. 11 illustrates a ventilation scoop and supplemental $O_2$ port according to principles described herein.

Another embodiment of the ventilation scoop and supplemental $O_2$ port 900 are illustrated in FIG. 11. ventilation scoop and supplemental $O_2$ port ventilation scoop supplemental port 900 snaps onto a gas connection port 1101 of the nasal respiratory apparatus. The ventilation scoop and supplemental $O_2$ port illustrated in FIG. 11 has two chambers separated by a wall 1106 in order to minimize flow from the supplemental $O_2$ chamber 1103 to dilute exhaled gases flowing into the ventilation chamber 1150. The ventilation chamber 1150 opening is located near the patient's mouth and channels exhaled gases towards the oral opening 1113*b* to the end tidal sample channel 1105*a* of the nasal respiratory apparatus. The ventilation chamber to oral opening of the ventilation scoop 1151 and the oral opening of the nasal respiratory apparatus may be coincident. If the patient is breathing orally, fresh gas is provided via the supplemental $O_2$ chamber with the opening located near the patient's mouth.

The ventilation chamber 1150 has an opening near the patient's mouth and provides a channel to the oral opening 1113*b* to end tidal sample channel 1105*a* of the nasal respiratory device. The ventilation chamber to nasal respiratory apparatus 1100 oral opening 1102 is located on the chamber top wall 1110 of the ventilation chamber 1150. It is coincident with the oral opening 1113*b* of the nasal respiratory device 1100 and allows exhaled gas to enter the oral opening 1113*b* of the nasal respiratory device. The supplemental $O_2$ chamber 1103 has an opening near the patient's mouth and allows for flow from a supplemental $O_2$ port 1104 to the patient who is breathing orally. The supplemental $O_2$ port 1104 is located on the chamber front wall 1111 of the supplemental $O_2$ chamber 1103 and connects to the supply line (not shown) of an $O_2$ or air source.

The $O_2$ port opening to $O_2$ chamber 1115 allows for gas flow between the supplemental $O_2$ port 1104 and the supplemental $O_2$ chamber 1103. A chamber separation wall 1106 separates supplemental $O_2$ flow in the supplemental $O_2$ chamber and ventilation flow in the ventilation chamber 1150. This is intended to minimize dilution of the exhaled gases that are sampled via the nasal/oral end tidal port 1105 of the nasal respiratory device.

A nasal respiratory gas port clip 1107 secures the ventilation scoop and supplemental $O_2$ port 900 to the nasal respiratory apparatus 1100. This occurs when the gas port clip 1107 is forced onto the gas connection port 1101 of the nasal respiratory apparatus in the Z direction and opening of the clip separates in the X-Z plane. As the clip 1107 continues to move in the Z direction, the clip 1107 wraps around the gas connection port 1101 and is clipped to the port 1107, securing it. The chamber top wall 1110 is then coincident with the bottom surface of the nasal respiratory device, preventing rotation about the Y-axis.

A push-pull Tab 1108 allows the clinician to attach or detach the ventilation scoop and supplemental $O_2$ port 900 to/from the nasal respiratory apparatus 1100. This is accomplished by pushing with a force in the Z direction to attach and pulling with a force in the −Z direction to detach. The chamber outer wall 1109 separates the supplemental $O_2$ chamber 1103 and the ventilation chamber 1150 from the outside environment radially about the Y-axis in the −Z direction. The chamber top wall 1110 separates the supplemental $O_2$ chamber 1103 and ventilation chamber 1150 from the outside environment radially about the Y-axis in the Z direction. The exception is the ventilation chamber to nasal respiratory apparatus oral opening **1113*b* in the ventilation chamber 1150. The chamber front wall 1111 separates the supplemental $O_2$ chamber 1103 and ventilation chamber 1150 from the outside environment axially in the Y direction. Both the supplemental $O_2$ chamber 1103 and ventilation chamber 1150 are open to the outside environment axially in the Y direction, near the patient's mouth via chamber openings 1112**.

Figure 12:
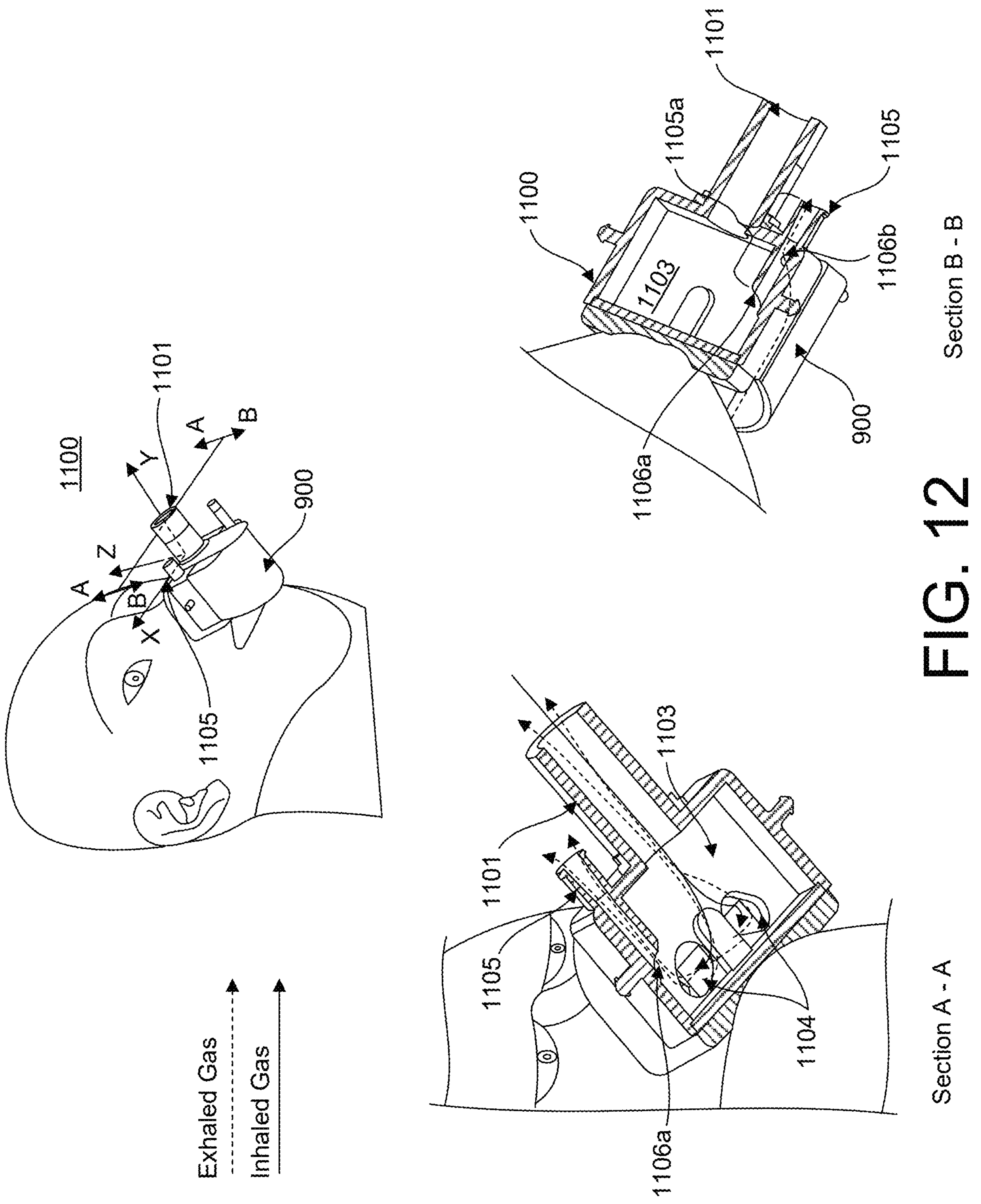
FIG. 12 are cross-sectional views illustrating a nasal respiratory apparatus with combined nasal/oral portend tidal sample port.

The present embodiment allows for sampling of $CO_2$ or other gases that are exhaled nasally and or orally. FIG. 12 shows cross-sections A-A and B-B of the nasal respiratory apparatus 1100. The gas connection port 1101, nares ports 1114 and nasal opening **1106*a* to the nasal/oral end tidal sample port 1105 are all common to the air chamber 1116. The ventilation scoop and supplemental $O_2$ port 900 routes exhalation to an opening below the air chamber 1116, near the mouth opening, and the flow path is common to the nasal/oral end tidal port 1105 by an oral opening 1113*b* to the end tidal sample port closer to an interface with a sample channel with a Luer connector. During the inspiratory portion of a breathing cycle, external gas enters the gas connection port 1101 into the air chamber 1116 where it then leaves the air chamber 1116 through the nares port 1114, entering the patient's nasal pharynx and ultimately into the lungs. This phase is illustrated by FIG. 12, Section A-A. During the expiratory phase of the breathing cycle, exhaled gasses can leave the lungs nasally, orally or both. If the gas leaves nasally as illustrated in FIG. 12, Section A-A, gas flows out the gas connection port 1101 and a portion also flows out the nasal opening 1104 to the end tidal sample channel then out the gas connection port 1101 if it is attached to a gas monitoring device. If the gas leaves orally as illustrated in FIG. 12, Section B-B, gas flows out the mouth and a portion also flows into the ventilation chamber 1150 of the ventilation scoop and supplemental $O_2$ port 900, out the ventilation chamber 1150 to nasal respiratory apparatus oral opening 1106*b* and into the oral opening 1113*b*** of the end tidal sample channel. It then leaves the channel and out the nasal/oral end tidal port if it is attached to a gas monitoring device (not shown). If end tidal gasses are not to be monitored, the nasal and/or oral end tidal ports may be plugged or capped.

Figure 13:
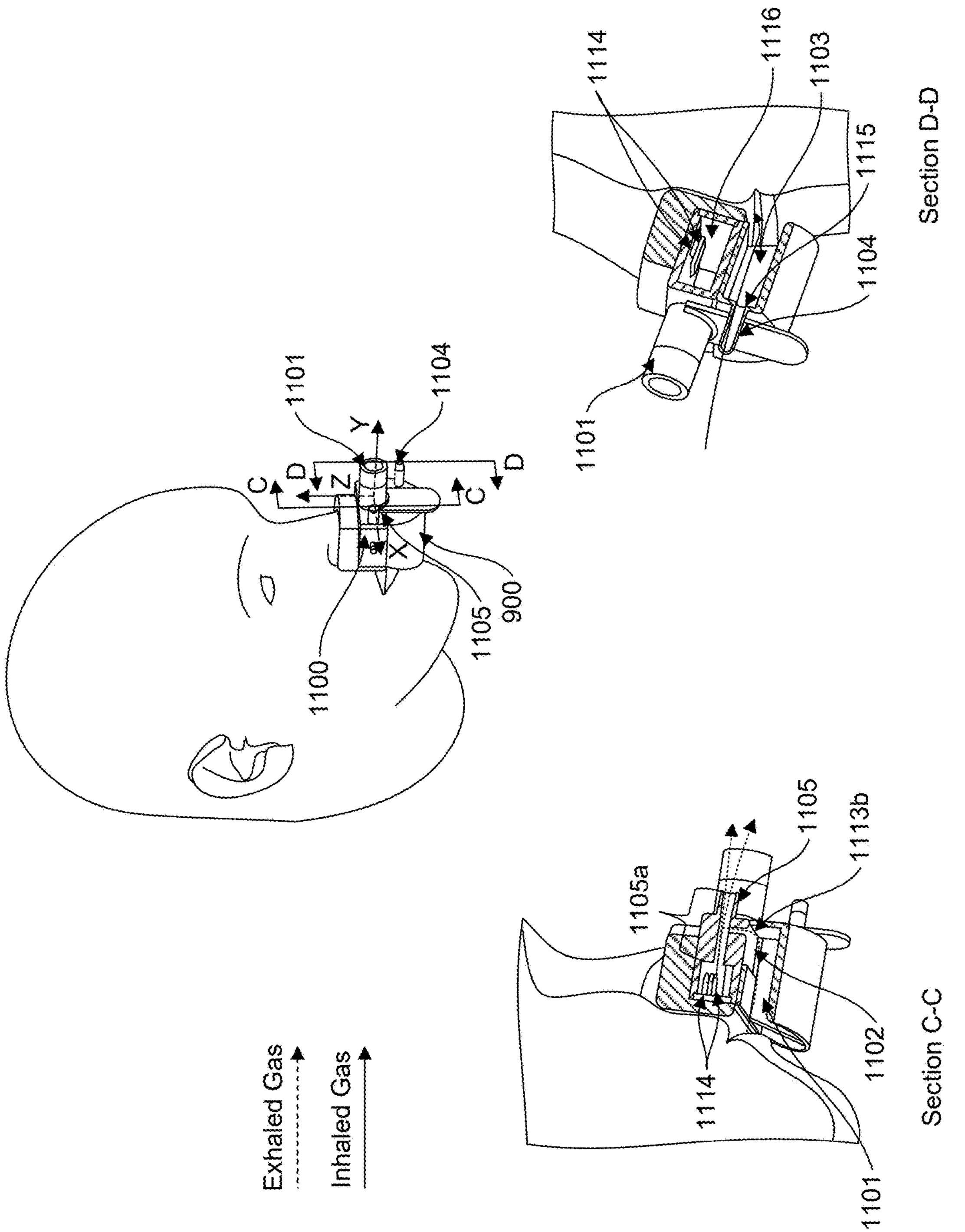
FIG. 13 are cross-sectional views illustrating a nasal respiratory apparatus with combined nasal/oral end tidal sample port and ventilation scoop with supplemental $O_2$ port.

FIG. 13 shows a cross-sectional view in the Y-Z plane along the end tidal sample port centerline, Section C-C, and along the supplemental $O_2$ port centerline, Section D-D. nasal and orally exhaled gases flowing to the end tidal sample channel and out the end tidal sample port are illustrated in Section C-C. orally exhaled gas flows into the ventilation chamber 1150, on to the ventilation chamber to nasal respiratory oral opening **1106*b*, into the oral opening 1113*b* to the end tidal sample channel and ultimately out the end tidal sample port to a Capnography sensor (not shown). nasally exhaled gas flows from the air chamber 1103 to the nasal opening 1113*a* to the end tidal sample channel, down the channel to the end tidal sample port 1105** and on to the capnography sensor (not shown).

Section D-D shows supplemental oxygen flowing through the supplemental $O_2$ port 1104, through the $O_2$ port opening to the $O_2$ chamber 1115, through the supplemental $O_2$ chamber to the patient's mouth, where it is inhaled. Primary gas flows to the patient through the gas connection port 1101 to the air chamber 1116 where it then flows through the nares port 1114 into the nasal pharynx of the patient. The patient can breathe nasally, orally or both simultaneously.

Figure 14:
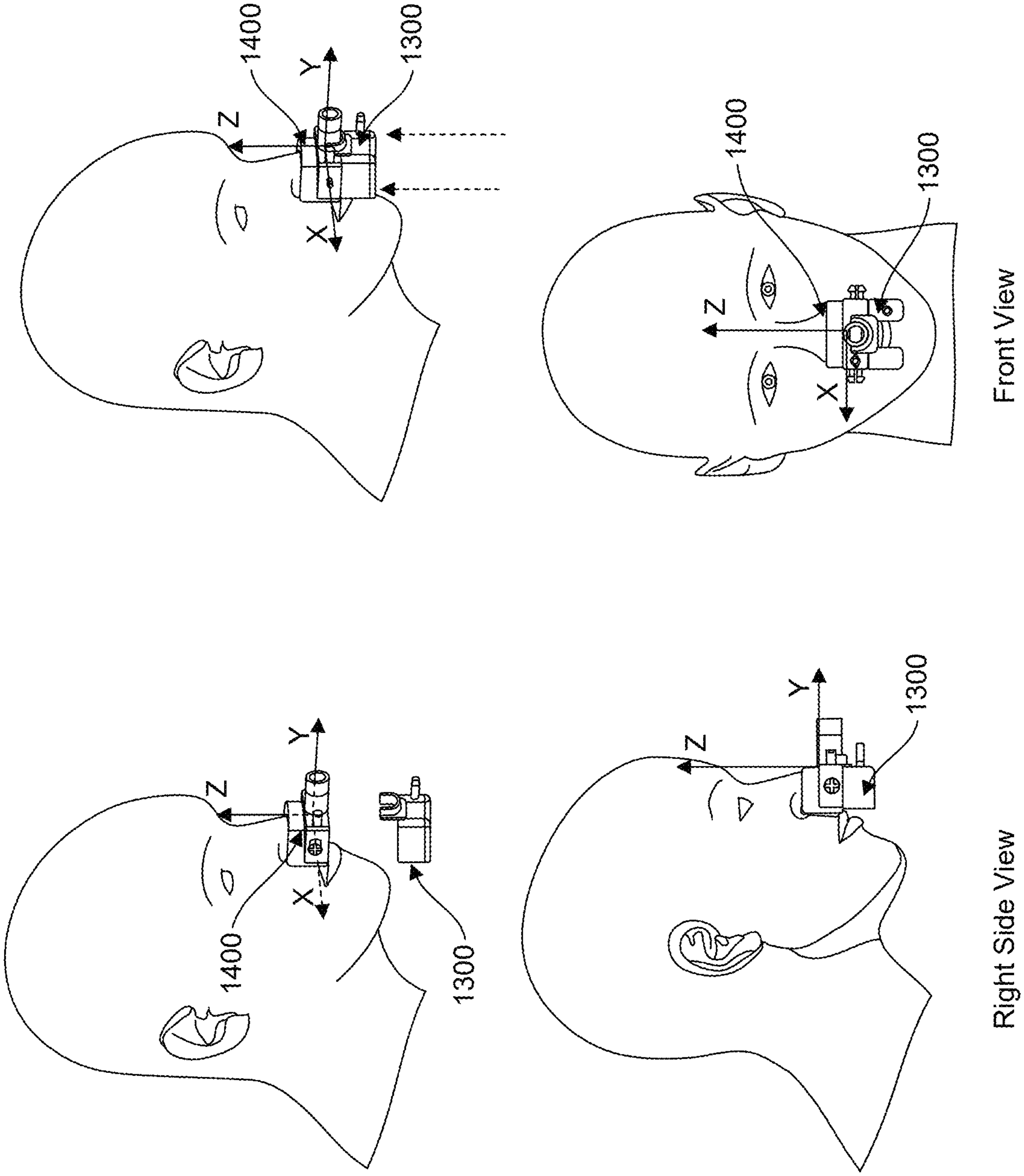
FIG. 14 illustrate a nasal respiratory apparatus with ventilation scoop and endoscope gap (gas connection port Parallel to Y-axis with Combined nasal and oral end tidal sample port).

Another embodiment of a system with nasal respiratory apparatus and ventilation scoop with a gas port parallel to the Y-axis is shown in FIG. 14, although the port could be parallel to the X or Z-axis. This configuration may be advantageous over the Z-axis configuration for patient access for different types of procedures in that it can be used with the patient in a supine position (laying on the back) or lateral position with the patient lying on the left or right side. As illustrated, a ventilation scoop 1300 may be separate from the nasal respiratory device 1400 and clip onto the gas connection port 1401 of the device 1400, one embodiment of which is illustrated in FIG. 14.

Figure 15:
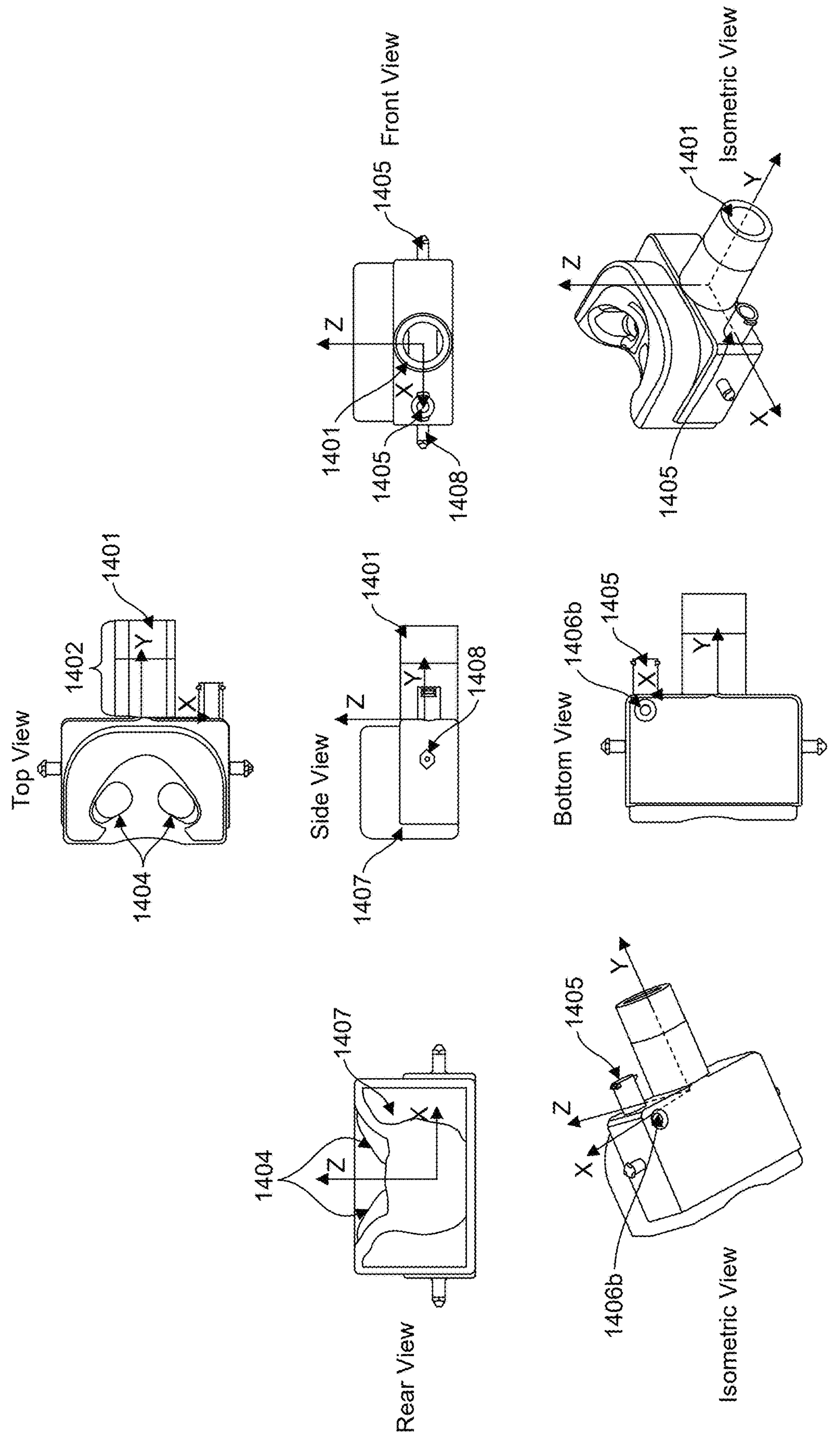
FIG. 15 illustrate a nasal respiratory apparatus (gas connection port Parallel to Y-axis).

Elements of the nasal respiratory apparatus configuration with the gas connection port 1401 parallel to the Y-axis are illustrated in FIG. 15, wherein the ventilation scoop 1300 includes a gap therein for passing an endoscope. An embodiment of the ventilation scoop with endoscopic gap is shown in more detail in FIG. 16. During the inhalation portion of the breathing cycle, pressurized gases (i.e., Oxygen ($O_2$), air anesthetic agents, etc.) are provided by a source (wall $O_2$ supply, bottled $O_2$ supply, ventilation machine, anesthesia machine, continuous positive airway pressure (CPAP) machine, bilevel positive airway pressure (BiPAP) machine, or another device). The pressurized gas enters the nasal respiratory apparatus via the gas connection port 1401, travels through the gas supply tube 1402 and the air chamber 1403 finally flowing out the nares ports 1404. gas leaves the nares ports 1404, traveling through the patient's nasal pharynx and eventually reaches the patient's lungs where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares ports 1404, traveling through the air chamber 1403, the gas supply tube 1402 and out the gas connection port 1401. A small amount of ventilated gas (i.e., carbon dioxide ($CO_2$), oxygen, anesthetic gases, etc.) can be sampled out of the single nasal/oral end tidal sample port 1405 by a monitoring device (not shown). If the patient exhales orally, gas from the mouth enters the oral ventilation scoop and enters the nasal/oral end tidal sample port 1405. The combined nasal and oral end tidal sample port 1405 is connected to a sample line (not shown) attached to a gas monitoring device (not shown). Additionally, a supplemental $O_2$ port is provided as part of the ventilation scoop where the supply line from an $O_2$ source can be plugged into a supplemental $O_2$ port, providing gases orally. An exemplary supplemental $O_2$ port is illustrated in FIG. 16 in combination with a ventilation scoop having an endoscope gap.

Figure 16:
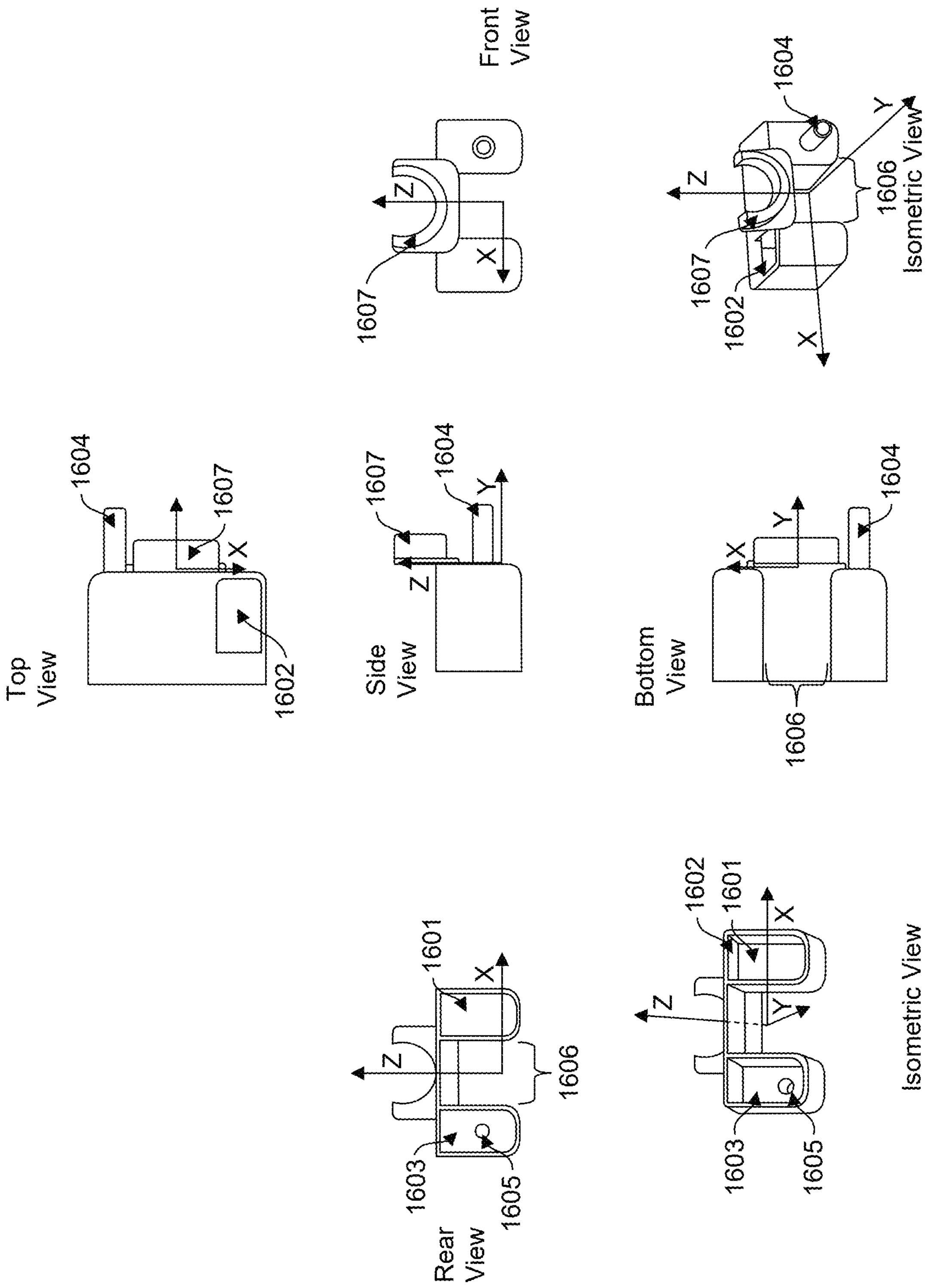
FIG. 16 illustrates a ventilation scoop, supplemental $O_2$ port and endoscope gap.

The ventilation scoop, supplemental $O_2$ port and endoscope gap 1600 are illustrated in FIG. 16. The ventilation scoop, supplemental $O_2$ port and endoscope gap fits onto the gas connection port (not shown) of the nasal respiratory device perhaps by snapping on, with a clasp or via interference fit or the like. The ventilation scoop, supplemental $O_2$ port and endoscope gap shown has two chambers separated by a gap 1606 that allows for the passage of an endoscope to the mouth of a patient. The ventilation chamber opening 1602 is located near the patient's mouth and channels exhaled gases towards the oral opening to the end tidal sample channel of the nasal respiratory apparatus (not shown). The ventilation chamber to nasal respiratory device oral opening 1602 of the ventilation scoop 1650 and the oral opening (not shown) of the nasal respiratory device may be coincident. If the patient is breathing orally, fresh gas is provided via the supplemental $O_2$ chamber 1603 with the opening located near the patient's mouth.

Figure 17:
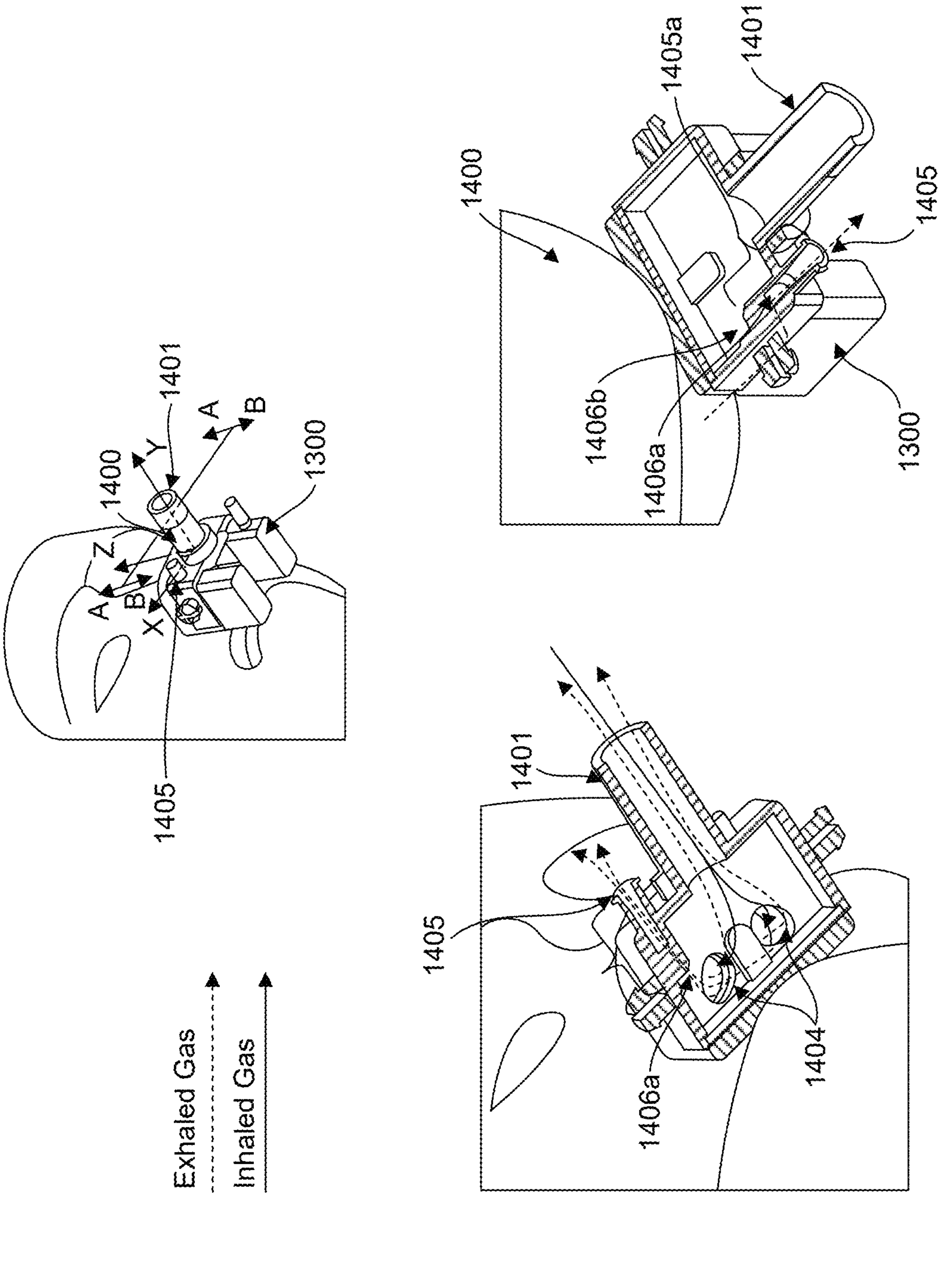
FIG. 17 are cross-sectional Views illustrating a nasal respiratory apparatus with combined nasal/oral end tidal sample port.

Referring to FIG. 17, gas port connection 1401 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. Note the gas port connection 1401 can be located in either the plus or minus direction in an orientation with its axis parallel to the X, Y or Z-axis.

The gas supply tube 1402 is a conduit containing and allowing for the flow of gas between the gas connection port 1401 and the air chamber 1403. The gas supply tube 1402 can either be rigid or expandable. Being expandable will accommodate for different size heads and allow the tubing to expand and retract as patients move head up and down, side to side, or rotate. Air chamber 1403 provides the structural and gas flow interface between the gas supply tube 1402, the nares ports 1404 and the end tidal sampling port 1405. One or two nares ports 1404 provide the mechanical and gas flow interface between the nares and the nasal respiratory apparatus.

The nasal/oral end tidal sample port 1405 parallel to the Y-axis is an optional interface allowing for sampling of the end tidal $CO_2$, end tidal $O_2$, etc. level from nasal exhalation by a sampling device (not shown) such as a Capnography Sensor, an oxygen sensor, or gas analyzer. The port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port 1405 can be on the plus or minus X-axis side of the air chamber. The end tidal sample port 1405 can be on the plus or minus X or Z-axis side of the air chamber.

Referring to FIG. 17, the end tidal sample channel 1405*a* has an opening into the air chamber 1403 via the nasal opening to the end tidal sample channel 1406*a* and the oral scoop via an oral opening to the end tidal sample channel 1406*b*, where it then terminates at the port opening 1405. $CO_2$ exhaled nasally into the air chamber 1403 enters the end tidal sample channel 1405 via the nasal opening to the end tidal sample channel 1406*a*. $CO_2$ exhaled orally into the ventilation scoop and supplemental $O_2$ port ventilation chamber 1450 enters the end tidal sample channel 1405*a* via the ventilation chamber to nasal respiratory device oral opening of the ventilation scoop 1406*b*. A nasal dam 1407 surrounds the nares ports 1404 and interfaces with the soft tissue of the patient's nasal base, providing a pressure seal in order to contain airflow between the nasal pharynx and the nasal respiratory apparatus. Head strap connectors 1408 provide mechanical tie points between the nasal respiratory apparatus and a head strap that secures nasal respiratory apparatus to the patient's head.

This embodiment allows for sampling of $CO_2$ or other gases that are exhaled nasally and or orally. FIG. 17 shows cross-sections A-A and B-B of the nasal respiratory apparatus. The gas port 1401, nares ports 1404 and nasal opening to the nasal/oral end tidal sample port 1405 are all common to the air chamber 1403. The ventilation scoop and supplemental $O_2$ port 1300 routes exhalation to an opening below the air chamber, near the mouth opening, and the flow path is common to the basal/oral end tidal port 1405 by an oral opening 1406*b* to the end tidal sample port 1405 closer to an interface with the sample channel with a Luer connector. During the inspiratory portion of a breathing cycle, external gas enters the gas connection port 1401 into the air chamber 1403, where it then leaves the air chamber 1403 through the nares port 1404, entering the patient's nasal pharynx and ultimately into the lungs. This phase is illustrated by FIG. 17, Section A-A. During the expiratory phase of the breathing cycle, exhaled gasses can leave the lungs nasally, orally or both. If the gas leaves nasally as illustrated in FIG. 17, Section A-A, gas flows out the gas connection port 1401 and a portion also flows out the nasal opening to the end tidal sample channel 1406*a* then out the gas connection port 1401 if it is attached to a gas monitoring device (not shown). If the gas leaves orally as illustrated in FIG. 17, Section B-B, gas flows out the mouth and a portion also flows into the ventilation chamber 1450 of the ventilation scoop and supplemental $O_2$ port 1300, out the ventilation chamber to nasal respiratory apparatus oral opening and into the oral opening of the end tidal sample channel 1406*b*. It then leaves the channel and out the nasal/oral end tidal port 1405 if it is attached to a gas monitoring device (not shown).

Figure 18:
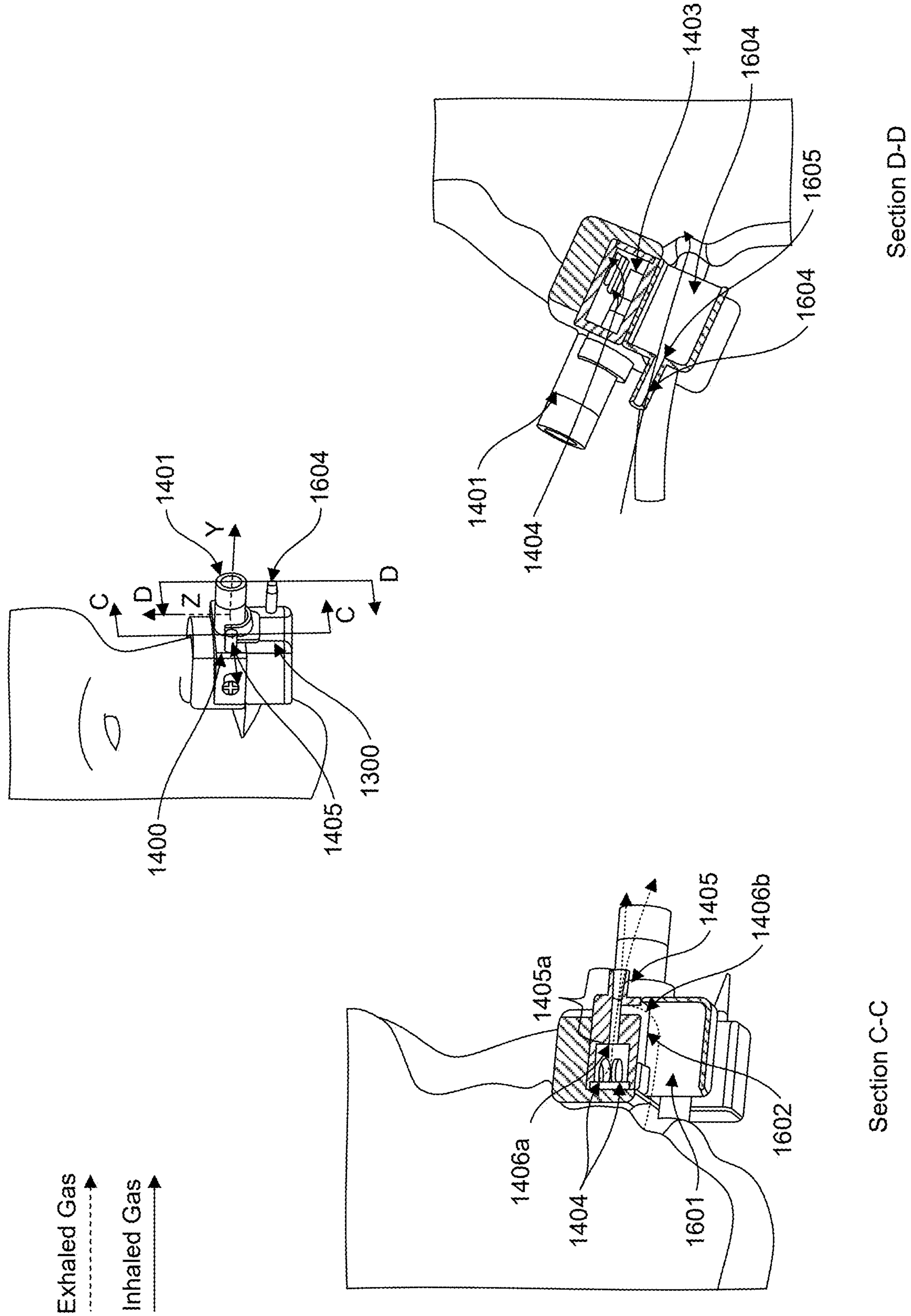
FIG. 18 are cross-sectional views illustrating a nasal respiratory apparatus with combined nasal/oral end tidal sample port and ventilation scoop with supplemental $O_2$ port.

FIG. 18 shows a cross-sectional view in the Y-Z plane along the portend tidal sample port 1405 centerline, Section C-C, and along the supplemental $O_2$ port 1604 Centerline, Section D-D. nasal and orally exhaled gases flowing to the end tidal Sample channel and out the portend tidal sample port are illustrated in Section C-C. orally exhaled gas flows into the ventilation chamber 1601, on to the ventilation chamber to nasal respiratory device oral opening 1602, into the oral opening to the end tidal sample channel 1406*b* and ultimately out the end tidal sample port 1405 to the Capnography sensor (not shown). nasally exhaled gas flows from the air chamber to the nasal opening to the end tidal sample channel 1406*a*, down the channel to the end tidal Sample port 1405 and on to the capnography sensor (not shown).

Section D-D shows supplemental oxygen flowing through the supplemental $O_2$ port 1604, through the $O_2$ port opening to the supplemental $O_2$ chamber 1605, through the supplemental $O_2$ chamber to the patient's mouth, where it is inhaled. Primary gas flows to the patient through the gas connection port 1401 to the air chamber 1403, where it then flows through the nares port 1404 into the nasal pharynx of the patient. The patient can breathe nasally, orally or both simultaneously.

Figure 19:
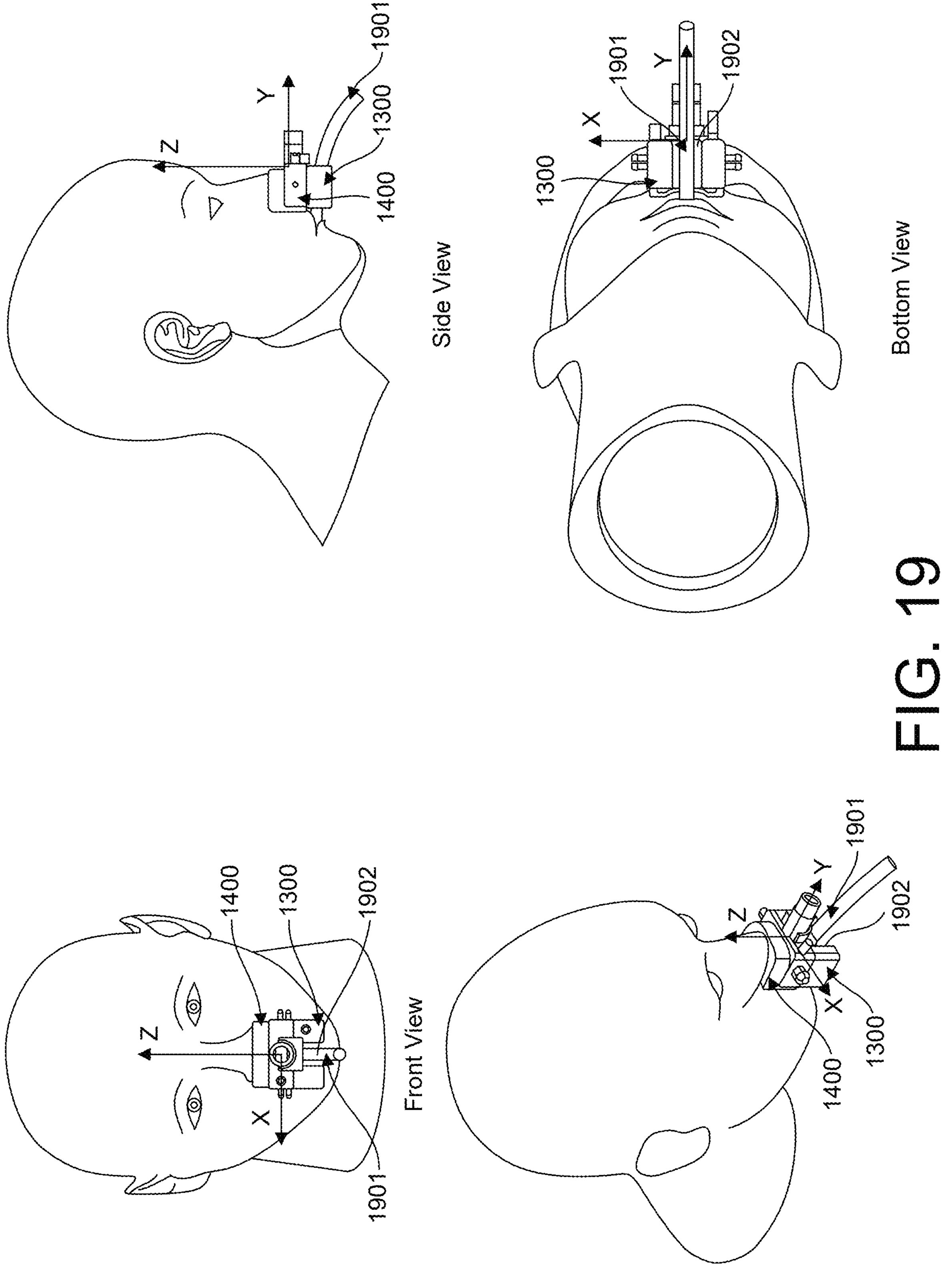
FIG. 19 illustrates an appliance with oral ventilation scoop, supplemental $O_2$ port and endoscope gap.

FIG. 19 provides multiple views of an endoscope 1901 being placed into the patient's mouth via the endoscope gap 1902. This allows for oral simultaneous oral $CO_2$ sampling, supplemental oral oxygen and endoscope use.

Referring to FIG. 16, The ventilation chamber 1601 has an opening near the patient's mouth and provides a channel to the oral opening to end tidal sample channel 1406*s* of the nasal respiratory device. The ventilation chamber to nasal respiratory apparatus oral opening 1602 is located on the chamber Top Wall 1610 of the ventilation chamber is designed to be coincident with the oral opening of the nasal respiratory device (not shown in FIG. 16) and allows exhaled gas to enter the oral opening of the nasal respiratory device. The supplemental $O_2$ chamber 1603 has an opening near the patient's mouth and allows for flow from the supplemental $O_2$ port to the patient who is breathing orally. The supplemental $O_2$ port 1604 is located on the chamber Front Wall of the supplemental $O_2$ chamber and connects to the supply line of an $O_2$ or air source. The $O_2$ port opening 1605 to $O_2$ chamber allows for gas flow between the supplemental $O_2$ port 1604 and the supplemental $O_2$ chamber 1603. The endoscope gap 1606 allows for passage of an endoscope to a patient's mouth while simultaneously sampling orally exhaled end tidal $CO_2$ and also providing supplemental $O_2$ orally. The nasal respiratory apparatus gas port clip 1607 secures the ventilation scoop and supplemental $O_2$ port 1600 to the nasal respiratory device. This occurs when the nasal respiratory apparatus gas port clip 1607 is forced onto the gas connection port 1401 of the device in the Z direction and the opening of the clip separates in the X-Z plane. As it continues to move in the Z direction, it wraps around the gas connection port 1401 and is clipped to the port 1401, securing it. The chamber Top Wall is then coincident with the bottom surface of the nasal respiratory device, preventing rotation about the Y-axis.

Figure 20:
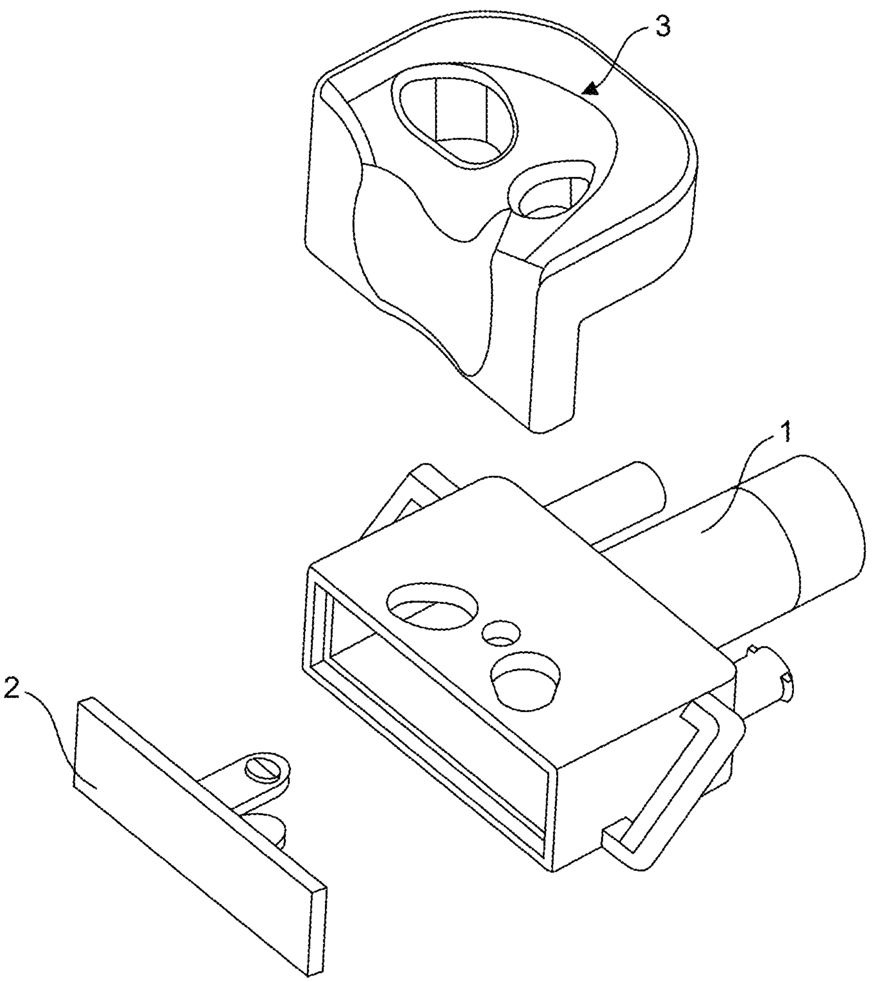
FIG. 20 illustrates three piece configuration a nasal respiratory apparatus according to principles described herein.

In an embodiment, an assembly/system according to principles described herein may nonexclusively include three parts, as illustrated in FIG. 20. The air chamber has an open end that is enclosed by snapping in the air chamber end cap into the opening. It is then covered by a soft nasal overmold or may include a separately removal nasal dam that overlies the nasal respiratory device and plugs into ports/openings that allow access to each gas through the upper wall of the air chamber. As shown in FIG. 20, the device may have two such ports/opening that correspond to nares ports in the nasal dam (3, in FIG. 20).

Figure 21A:
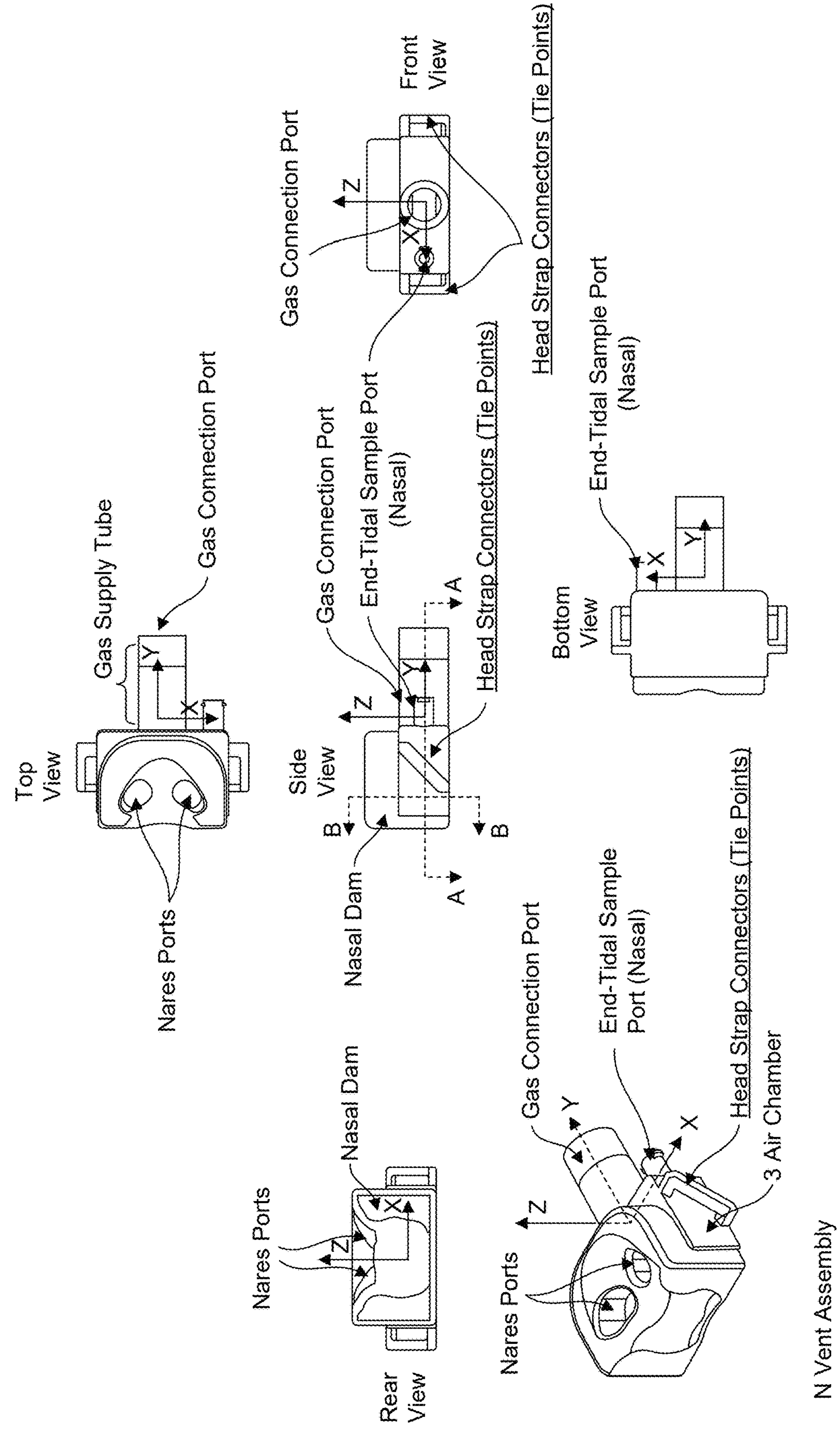
FIG. 21A illustrates an embodiment of the nasal respiratory apparatus according to principles described herein.
Figure 21B:
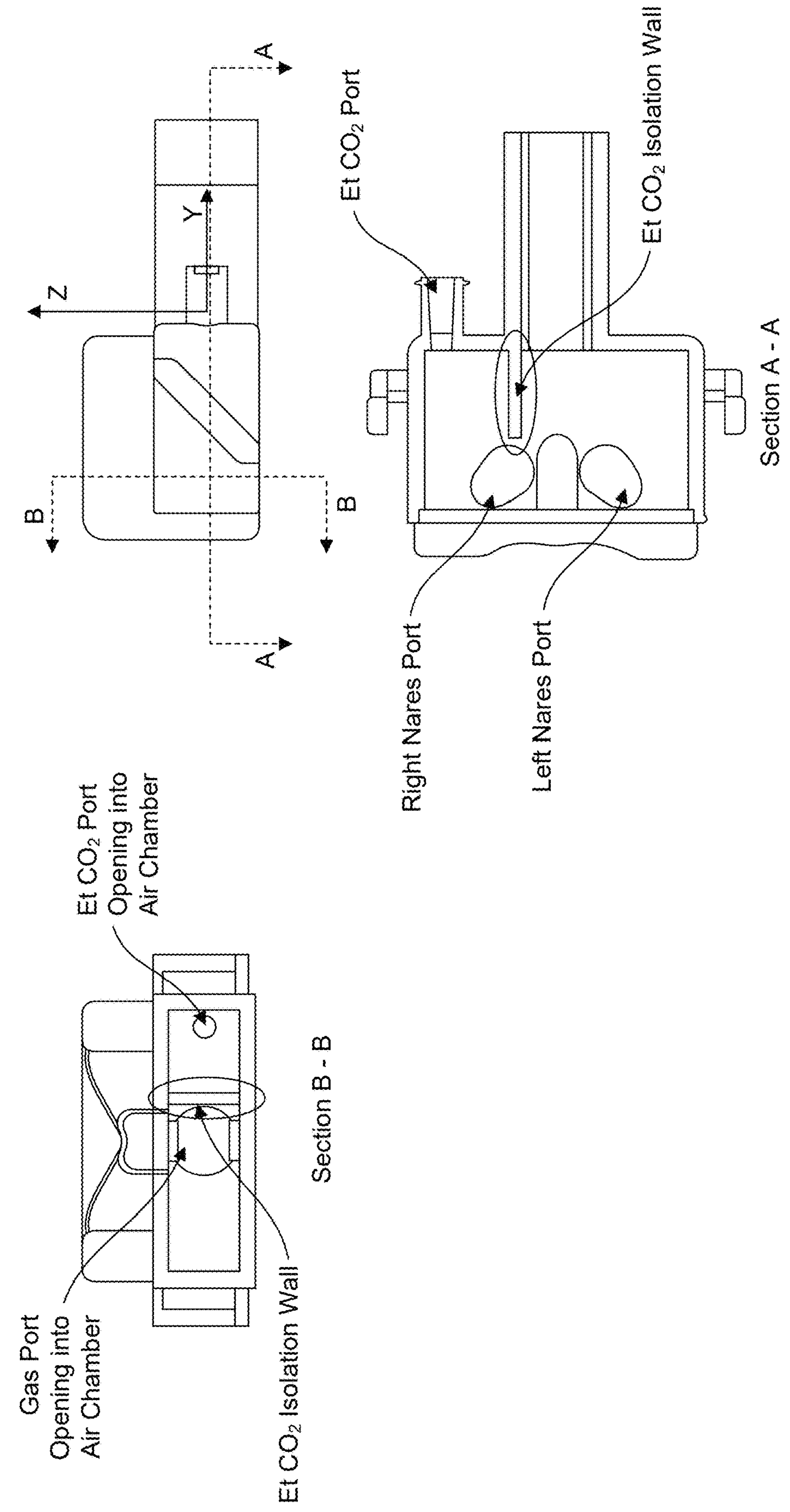
FIG. 21B illustrates an embodiment of the nasal respiratory apparatus with an isolation wall in an air chamber thereof.

Further detail of an assembly having three parts is illustrated in FIG. 21A. As illustrated, the air chamber has an open end that is enclosed by snapping in the air chamber end cap into the opening. It is then covered by a soft nasal cushion, which may be overmolded onto the exterior of the air chamber upper surface or may be a separate removable nasal dam. Elements of the present embodiment of the nasal respiratory apparatus are illustrated in FIG. 21B and include an air chamber, air chamber end cap, and nasal cushion. The material utilized to produce the assembly may be polypropylene, polystyrene, high impact polystyrene or equivalent for the air chamber structure and air chamber end cap. The nasal overmold may be made of any suitable material with a Shore A of 5-50. Such suitable material may include thermoplastic elastomers, silicone or any other material of appropriate Shore A.

The assembly includes has an $EtCO_2$ (end tidal $CO_2$) isolation wall to reduce the mixing of fresh gas from the gas port with exhaled gas from the right (or left) nares. The objective is to reduce mixing of fresh and inhaled gas in order to obtain a purer exhalation sample via the end tidal port as shown in the section views of FIG. 21B and FIG. 21C. FIG. 21B shows the $EtCO_2$ isolation wall, located in the Y-Z plane, extends between the top and bottom air chamber surfaces parallel to the X-Y plane. The wall thus creates a barrier between the gas port opening in the "left" half of the air chamber, section B-B where fresh gas enters the air chamber and the end tidal sample port opening in the "right" half of the chamber. The $EtCO_2$ isolation wall extends along the Y-axis from the right air chamber wall, ending at the right nares port opening as shown in section C-C.

Figure 21C:
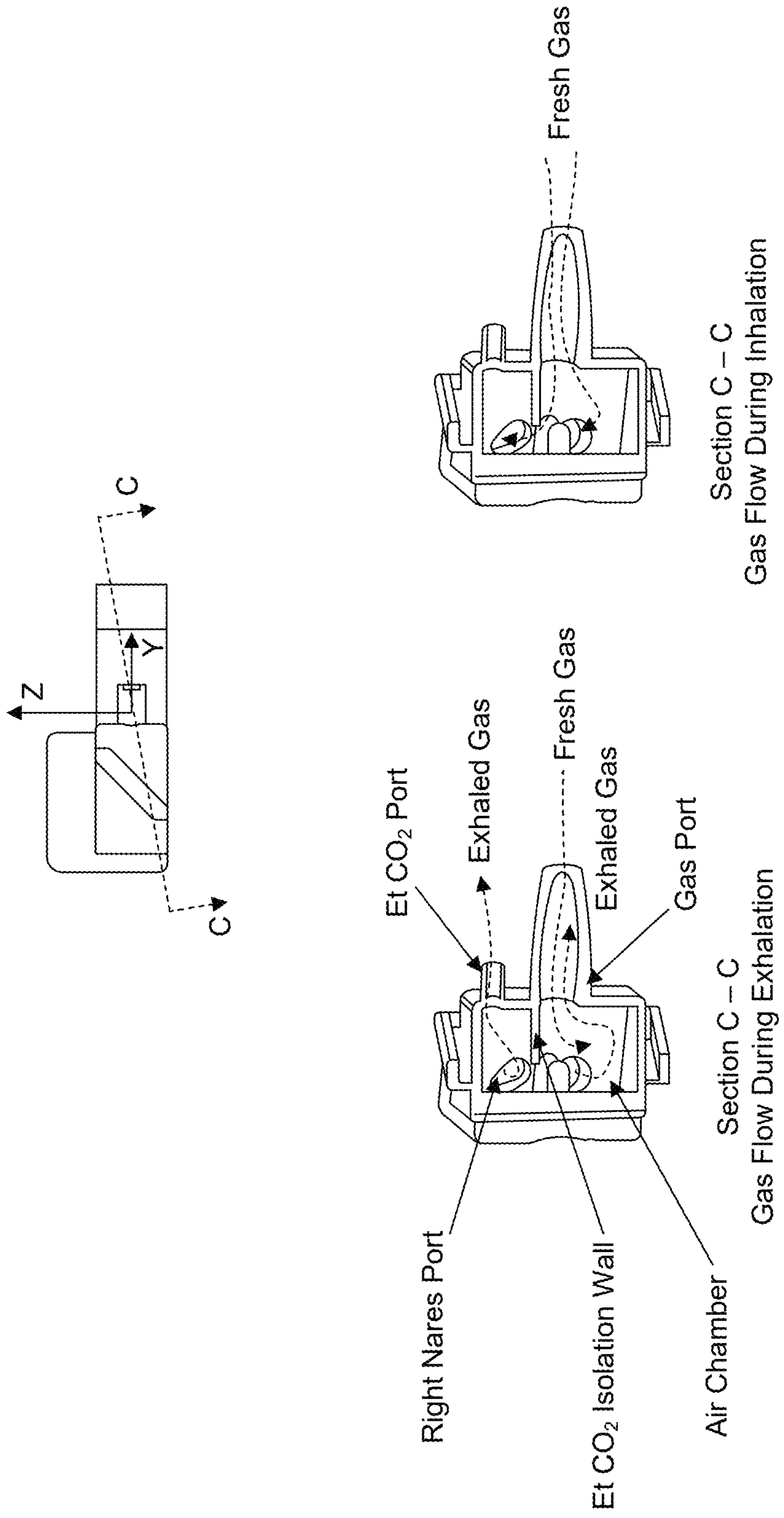
FIG. 21C illustrates a cross-sectional view and flow of expiratory gases that occurs during exhalation and inspiratory gases occurring during inspiration.

FIG. 21C shows a cross-sectional view, C-C, with a diagram of expiratory gas flow that occurs during exhalation and inspiratory gas flow occurring during inspiration. Fresh gas is always being provided to the patient via the gas port. During expiration, pressure derived from the patient's diaphragm expels consumed gas containing $CO_2$ through the right and left nares ports into the air chamber. If an $EtCO_2$ end tidal sample port is attached to a capnography machine sample vacuum line, gas expelled from the right nares port will flow through the $EtCO_2$ sample port and the $EtCO_2$ isolation wall will minimize any fresh gas that could be present, diluting the measurement. When the patient inhales fresh gas as shown in FIG. 21C, fresh gas can travel to both the right and left nares ports.

Any of the embodiments of the nasal respiratory device described herein may include $EtCO_2$ isolation wall that substantially isolates exhaled gas from fresh gas, as described with respect to FIGS. 21A-C and/or an $EtCO_2$ isolation wall that allows fresh gas to enter both the left and right nares of the patient during inhalation.

The isolation wall described with respect to FIGS. 21A, 21B and 21C may be included in any of the air chambers in any of the configurations described throughout this document. Exemplary descriptions of an end tidal sample port is provided herein such as the end tidal sample port 5, or any other configuration of end tidal sample port described herein. Exemplary description of a gas connection port is provided herein such as the gas connection port 1, or any other configuration of the gas connection port described herein may be used in connection with the isolation wall described with reference to FIGS. 21A-C. Moreover, the gas connection port could also interface with a standard oxygen line. The apparatus described below and shown in FIG. 22 may incorporate the air chamber of FIGS. 21A-C, for example, without limitation to the air chamber isolation wall's inclusion with other apparatuses described herein. For example, the isolation wall could be used in conjunction with the air chamber 2203 shown in FIG. 22, or any other appropriate air chamber described at various point throughout this document, for example, in FIGS. 23 and 24 Any disclosed $CO_2$ port, gas connection port, strap connectors, nasal dams, nasal interfaces, nares ports, forehead standoffs or the like may be used in conjunction with the air chamber configuration of FIGS. 21A-C.

In combination with the air chamber of FIG. 21, a gas port connection provides interface with standard $O_2$ source, anesthesia machine, hyper-inflation bag, high-flow source or ventilator, which may be via a standard 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. The gas port connection can be located in either the plus or minus direction in an orientation with its axis parallel to the X, Y or Z-axis. The gas connection port may connect to a CPAP or BiPAP.

The gas supply tube is a conduit containing and allowing for the flow of gas between the gas connection port and the air chamber, which includes an isolation wall therein such that there is a barrier between the gas port opening in the "left" half of the air chamber, section B-B where fresh gas enters the air chamber, and the end tidal sample port opening in the "right" half of the chamber. The $EtCO_2$ isolation wall extends along the Y-axis from the right air chamber wall, ending at the right nares port opening as shown in section C-C. The gas supply tube can either be rigid or expandable. Being expandable will accommodate for different size heads and allow the tubing to expand and retract as patients move head up and down, side to side, or rotate. Air chamber provides the structural and gas flow interface between the gas supply tube, at least one nares ports and the end tidal sample port. One or two nares ports provide the mechanical and gas flow interface between the nares and the nasal respiratory apparatus. The portend tidal sample port is an optional interface allowing for sampling of the end tidal $CO_2$, etc. level from nasal exhalation by a sampling device such as a Capnography Sensor, an oxygen sensor, or gas analyzer (not shown). The port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port can be on the plus or minus X-axis side of the air chamber.

The nasal dam surrounds the nares ports and interfaces with the soft tissue of the patient's nasal base, providing a pressure seal in order to contain airflow between the nasal pharynx and the nasal respiratory apparatus. Connection pins allow for interface with either an orally exhaled end tidal $CO_2$ sampling connection, or a bite block or other desired modular component. Head strap connectors provide mechanical tie points between the device and a head strap (not shown) that secures the nasal respiratory apparatus to the patient's head.

Figure 22:
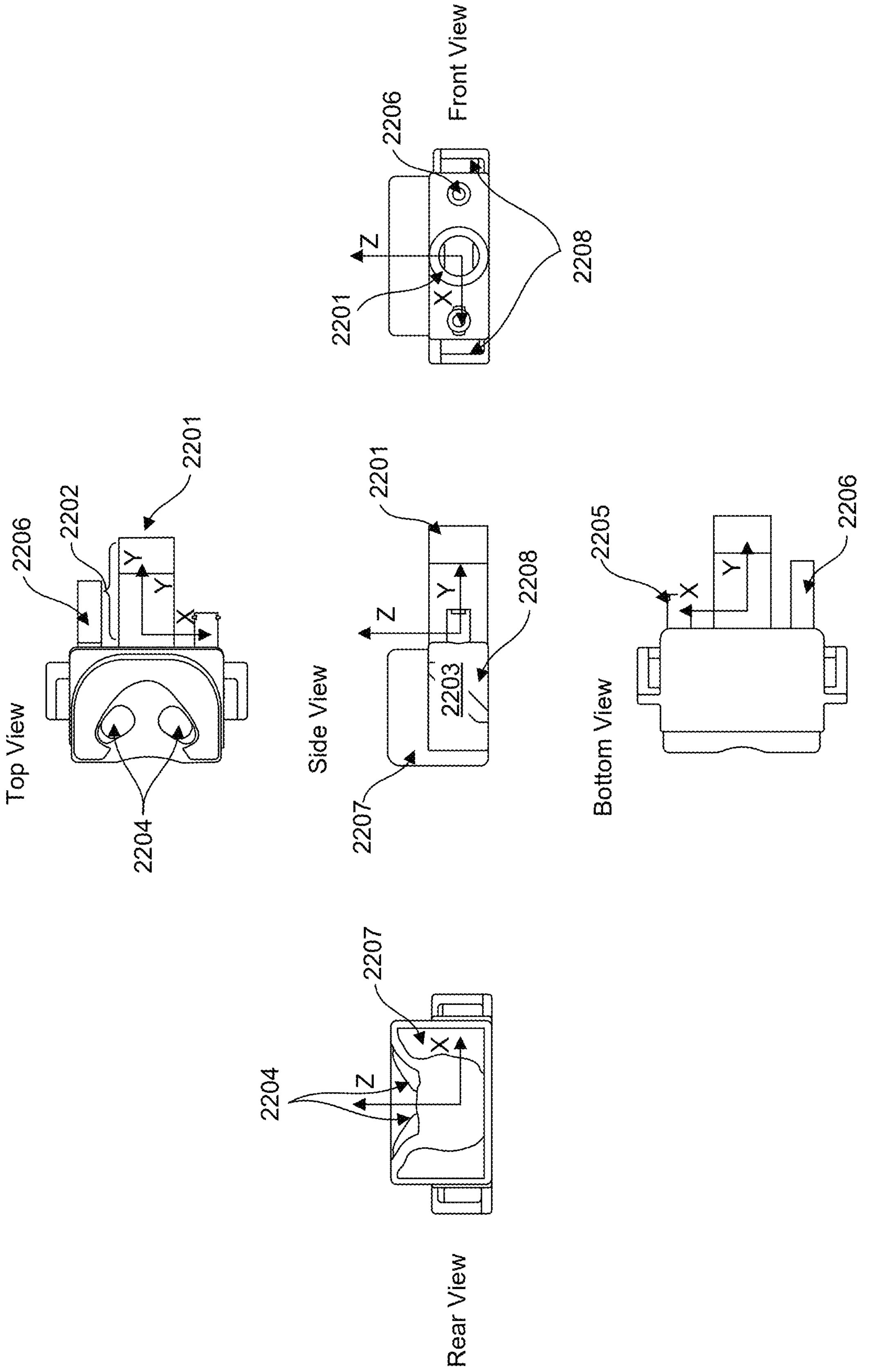
FIG. 22 illustrates a nasal respiratory apparatus with a nasal dam.

Additional description of an assembly according to principles described herein are made with reference to FIG. 22. A gas port connection 2201 provides an exemplary interface, which may include a 15 mm conical connector as defined by ISO 5356-1:2015(E). A gas supply tube 2202 is a conduit containing and allowing for the flow of gas between the gas connection port 2201 and an air chamber 2203. Air chamber 2203 provides the structural and gas flow interface between the gas supply tube 2202, at least one nares ports 2204 and an end tidal sample port 2205.

One or two nares ports 2204 provide the mechanical and gas flow interface between the nares and the nasal respiratory chamber. The nasal end tidal sample port 2205 being parallel to the X or Y-axis supports sampling of the end tidal $CO_2$. In the case of the extension of the X axis, the end tidal sample port could extend from either face of the air chamber parallel to the X-Z plane. It could also be parallel to the Z-axis, extending from either face of the air chamber parallel to the X_Y plane. The port exterior may be a female luer slip connector is per ISO 80396-7: 2016(E). supplemental $O_2$ port 2206 allows for the supply of supplemental $O_2$ via an $O_2$ line (not shown).

A nasal dam 2207 may surround the nares ports 2204 and interface with the soft tissue of a patient's nasal base, providing a pressure seal in order to contain airflow between the patient's nasal pharynx and the nasal respiratory device. Head strap connectors (tie points) 2208 provide mechanical tie points between the device and the head strap that secures the device to the patient's head.

Figure 23:
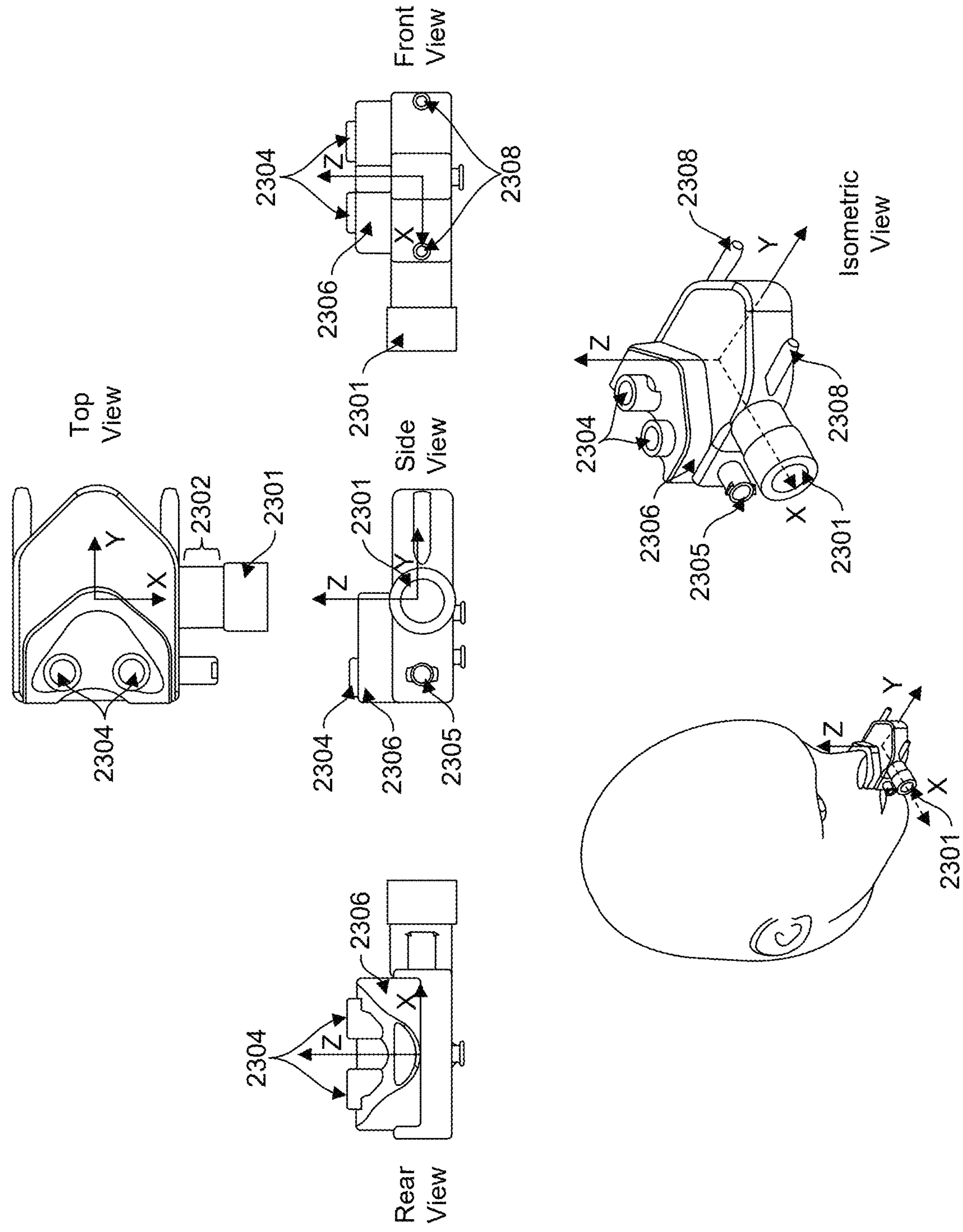
FIG. 23 illustrates a nasal respiratory apparatus with a nasal dam and with gas port parallel to the X-axis.
Figure 24:
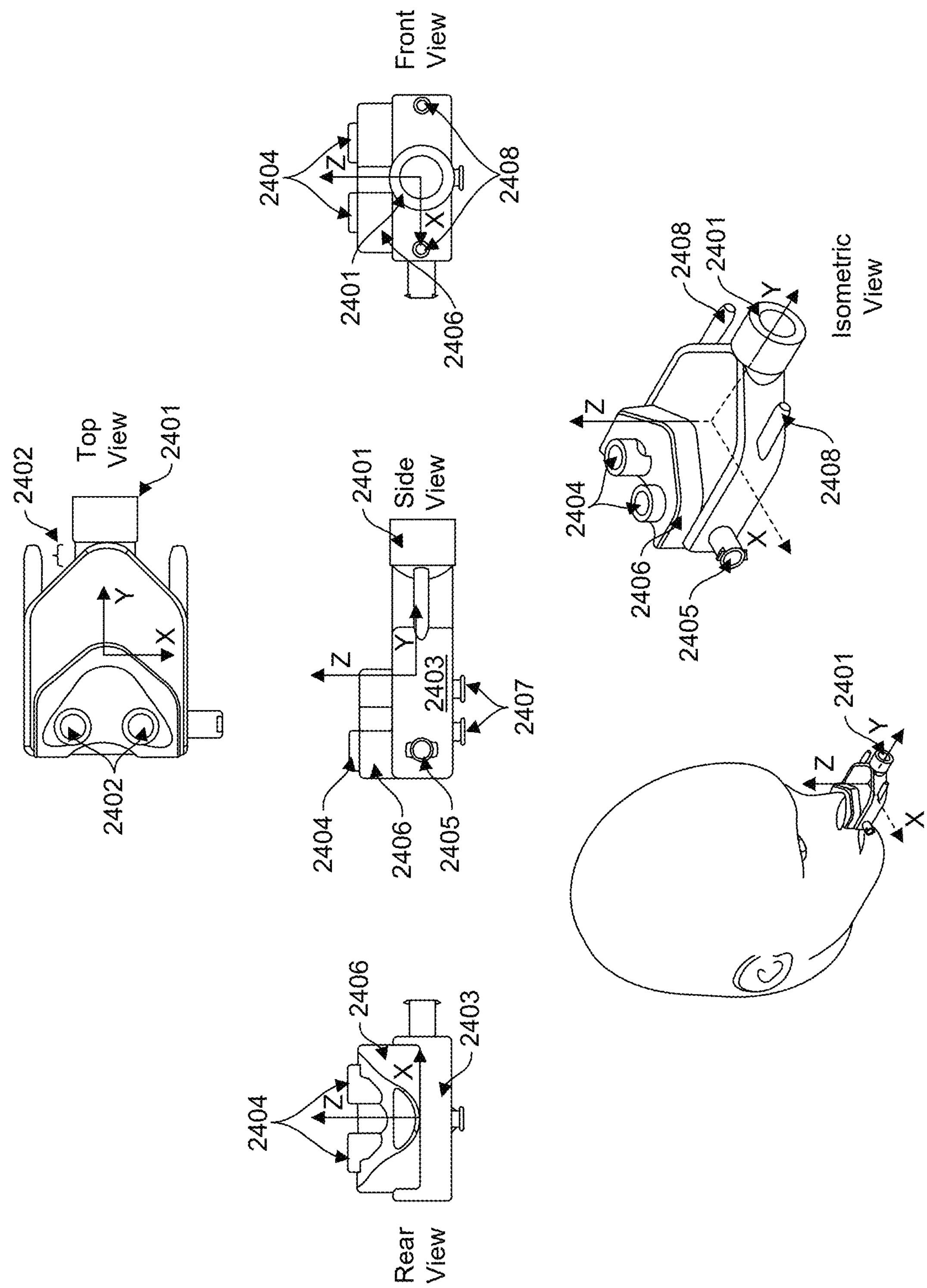
FIG. 24 illustrates a nasal respiratory apparatus with a nasal dam and with gas port parallel to the Y-axis.

The device configuration shown in FIG. 1 and FIG. 2 has a gas connection port parallel to the Z-axis, allowing for connection with a gas source above the forehead. Other embodiments of the device to be described with respect to FIG. 23 and FIG. 24 are configured to have a gas connection port with an axis parallel to the X-axis, FIG. 23, or the Y-axis, FIG. 24. These configurations may be advantageous over the Z-axis configuration for patient access for different types of procedures.

Elements of the nasal respiratory apparatus for configurations with the gas connection port parallel to the X-axis and parallel to the Y-axis are illustrated in FIG. 23 and FIG. 24 respectively. Except for the gas port connection axes orientation, both configurations have the same elements, as described herein. During the inhalation portion of the breathing cycle, pressurized gases (i.e., Oxygen ($O_2$), air anesthetic agents etc.) are provided by a source (wall $O_2$ supply, bottled $O_2$ supply, ventilation machine, anesthesia machine continuous positive airway pressure (CPAP) machine, or another device). The pressurized gas enters the nasal respiratory apparatus via the gas connection port 2301/2401, travels through the gas supply tube 2302/2402 and the air chamber 2303/23403 finally flowing out the nares ports 2304/2404. gas leaves the nares ports 2304/2404, traveling through the patient's nasal pharynx and eventually reaches the patient's lungs where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares ports 2304/2404, traveling through the air chamber 2303/2403, the gas supply tube 2302/2402 and out the gas connection port 2301/2401. A small amount of ventilated gas (i.e. carbon dioxide $CO_2$), oxygen, anesthetic gases, etc.) can be sampled out of the portend tidal sample port 23052/2405 by a monitoring device (not shown).

Gas port connection 2301/2401 provides interface with standard $O_2$ source, anesthesia machine, hyper-inflation bag, high-flow source or ventilator, which may be via a standard 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. The gas port connection 2301/2401 can be located in either the plus or minus direction in an orientation with its axis parallel to the X, Y or Z-axis.

The gas supply tube 2302/2402 is a conduit containing and allowing for the flow of gas between the gas connection port 2301/2401 and the air chamber 2303/2403. The gas supply tube 2302/2402 can either be rigid or expandable. Being expandable will accommodate for different size heads and allow the tubing to expand and retract as patients move head up and down, side to side, or rotate. Air chamber 2303/2403 provides the structural and gas flow interface between the gas supply tube, at least one nares ports 2304/2404 and the end tidal sample port 2305/2405. One or two nares ports 2304/2403 provide the mechanical and gas flow interface between the nares and the nasal respiratory apparatus. The portend tidal sample port 2305/2405 is an optional interface allowing for sampling of the end tidal $CO_2$, etc. level from nasal exhalation by a sampling device such as a Capnography Sensor, an oxygen sensor, or gas analyzer (not shown). The port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port 2305/2405 can be on the plus or minus X-axis side of the air chamber 2303/2403.

The nasal dam 2306/2406 surrounds the nares ports 2304/2404 and interfaces with the soft tissue of the patient's nasal base, providing a pressure seal in order to contain airflow between the nasal pharynx and the nasal respiratory apparatus. connection pins 2307/2407 allow for interface with either an orally exhaled end tidal $CO_2$ sampling connection, or a bite block or other desired modular component. Head strap connectors 2308/2408 provide mechanical tie points between the device and a head strap (not shown) that secures the nasal respiratory apparatus to the patient's head.

Figure 25:
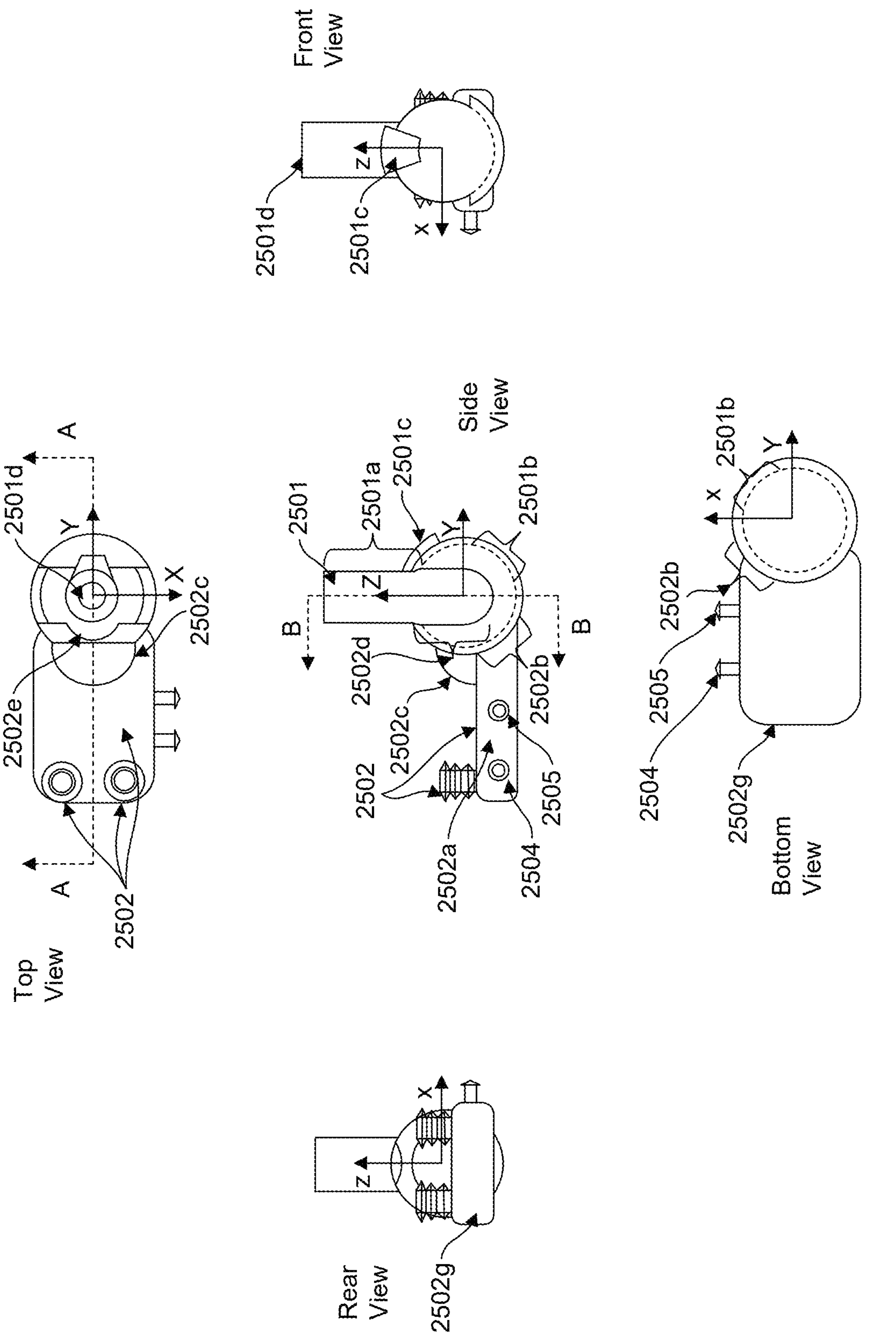
FIG. 25 illustrates an articulated nasal respiratory apparatus.

An articulated nasal respiratory apparatus is illustrated in FIG. 25 and includes an air chamber assembly 2502 and a gas connection port assembly 2501. Detail for the cross-section A-A noted in the Top View of FIG. 25 is provided in FIG. 26. The cross-section A-A looking down the X-axis gas connection port assembly 2501 and the air chamber assembly 2502. The cross-section A-A looks down the X-axis gas connection port assembly 2501 and the air chamber assembly 2502. Detail for the cross-section B-B noted in the Side View of FIG. 25 is provided in FIG. 27. The cross-section B-B looks down the Y-axis gas connection port assembly 2501 and the air chamber assembly 2502.

The gas connection port assembly 2501 can rotate from 0° to approximately 20° about the X-axis and +/−90° about the Y-axis. With the gas connection port assembly 2501 rotated 0° to 20° about the X-axis and 0° about the Y-axis, it supports oxygenation and ventilation of a patent, where the gas flows through a tube that is nominally in line with the nose and forehead of the patient. With the gas connection port assembly 2501 rotated 0° the X-axis and +/−90° about the Y-axis, oxygenation and ventilation can be provided with gas flow occurring from the right or left side of the patient.

The articulated nasal respiratory apparatus as described herein could interface with an oral end tidal attachment as described herein, supporting one or both nasal and oral end tidal $CO_2$ sampling. Gas port connection 2501 provides the interface with external gas supply and ventilation systems (not shown). The gas supply channel 2501*a* is a conduit containing and allowing for the flow of gas between the gas connection port assembly 2501 and the air chamber assembly 2502. gas connectors attach to this portion of the assembly. With the entrance port 2501*d* at the top of the channel it may be designed to interface with a standard $O_2$ source, anesthesia machine, hyper-inflation bag, high-flow source or ventilator via a standard 8.5 mm, 11.5 mm, 15 mm or 22 mm conical connectors as defined by ISO 5356 or current equivalent standard. Other connector interfaces are possible. This assembly is composed of several sub-elements. The entrance port 2501*d* may be designed to interface with male or female connectors. A male connection interface is shown on this illustration.

The gas supply channel 2501*b* terminates into the ball. Internal to the ball is a channel for gas flow with a cross section of an L or elbow. gas flows out the exit port 2501*e* nominally at a 90° angle to the entrance flow direction. A ball 2501*b* interfaces with the socket 2502*b* of the air chamber assembly 2502, creating a substantially leak-free seal due to mechanical force conforming the ball surface to the socket surface. Air flows between the gas port connection assembly 2501 and the air chamber assembly 2502 through the socket-chamber opening 2502*f*, part of the socket 2502*b*.

In order to keep the ball exit port 2501*e* within the boundary of the socket-chamber opening 2502*f*, required for gas flow, the Z-axis rotation retainer 2501*c* prevents the gas port connection assembly 2501 from rotating about the Z-axis of the gas supply channel 2501*a*. The entrance port 2501*d* is at the top of the gas supply channel that interfaces with external gas supply and ventilation devices.

Figure 27:
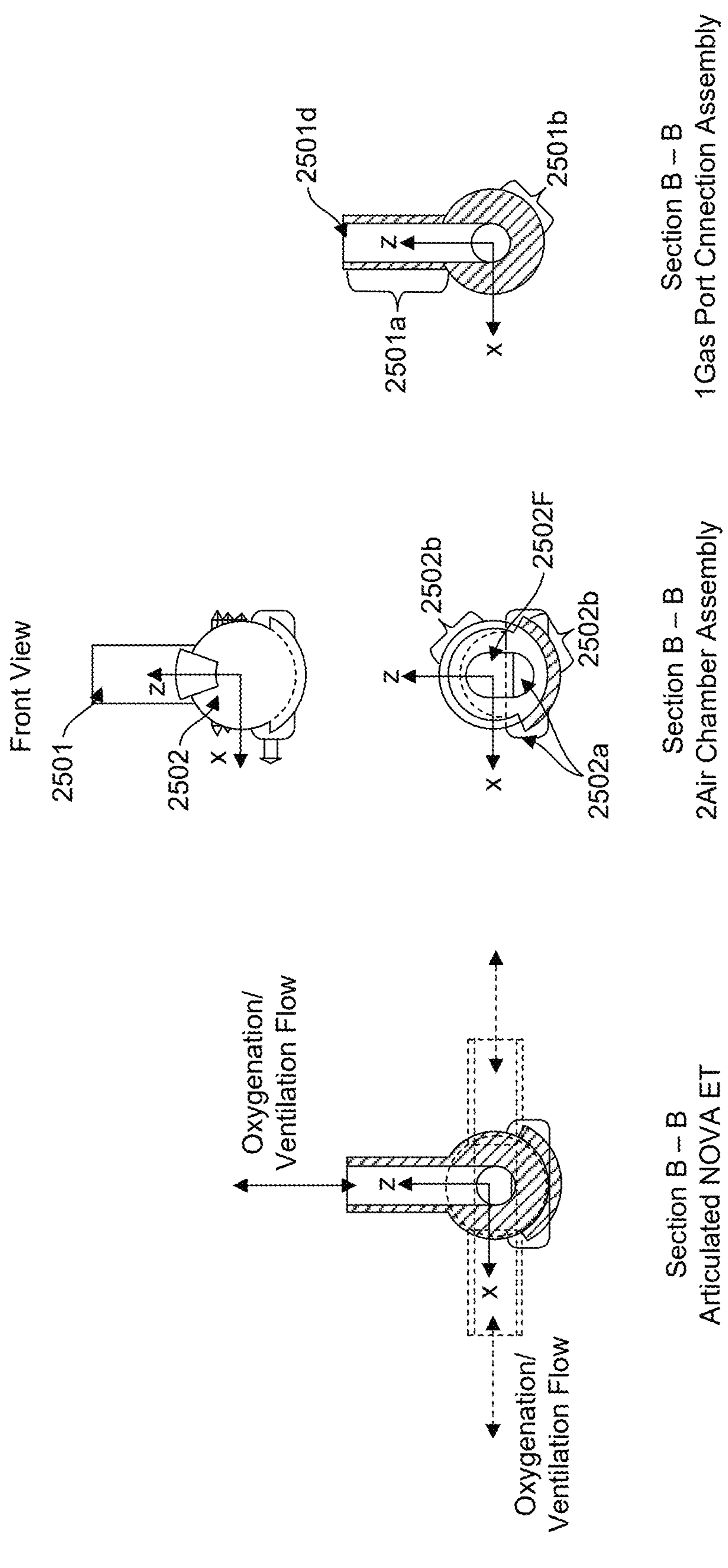
FIG. 27 illustrates section B-B of the articulated appliance of FIG. 25.
Figure 28:
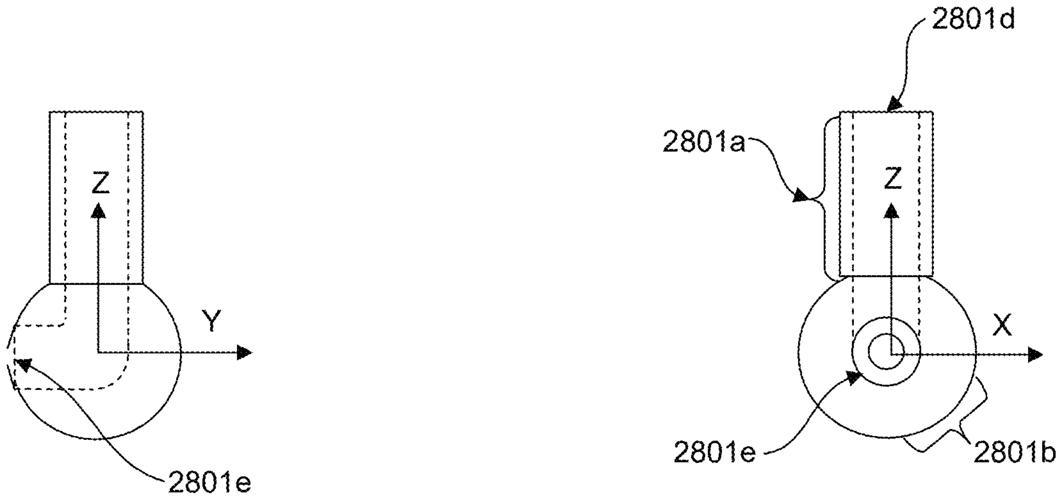
FIG. 28 illustrates a gas port connection assembly of an articulated appliance.

Referring to FIG. 27, exit port 2501*e* is where gas flows from the gas port connection assembly 2501 to the air chamber assembly 2502, or visa-versa. The perimeter of the exit can be a circular or nominally oval cross section and could be slightly raised radially outward from the ball 2501*b*, have a rubber coating or a seal illustrated as an option in order to improve the gas seal against an interface with the socket, where it rests. The air chamber assembly 2502 is one of two assemblies making up the articulated nasal respiratory apparatus. It provides the structural and gas flow interface between the gas port connection assembly 2501, at least one nares port 2503 and an end tidal Sampling port 2504. A chamber 2502*a* mechanically supports the nares ports 2503, the end tidal sample port 2504 and is the gas flow channel between the ball opening 2800*e* and the nares ports 2503. The socket 2502*b* provides the mechanical support and sealing interface with the ball 2501*b*. The air dome 2502*c* contains gas flow from the atmosphere and provides a volumetric space for unhindered gas flow from the ball exit port 2501*e*, through the socket-chamber opening 2502*f* to the chamber 2502*a*. The port slots 2502*d* and 2502*e* on either side of the socket run parallel to the Z-axis and allows the gas port connection assembly to be rotated about the Y-axis +/−90° or any other desired angle.

The X-axis port slot 2502*e* allows the gas port connection assembly 2501 to be rotated about the X-axis from 0° to approximately 20°. The articulated nasal respiratory apparatus can rotate approximately 20° about the X-axis for any Y-axis rotation from −90° to 90° or any other desired angle if the X-axis port slot 2502*e* is enlarged about the Y-axis to accommodate the additional range.

Figure 26:
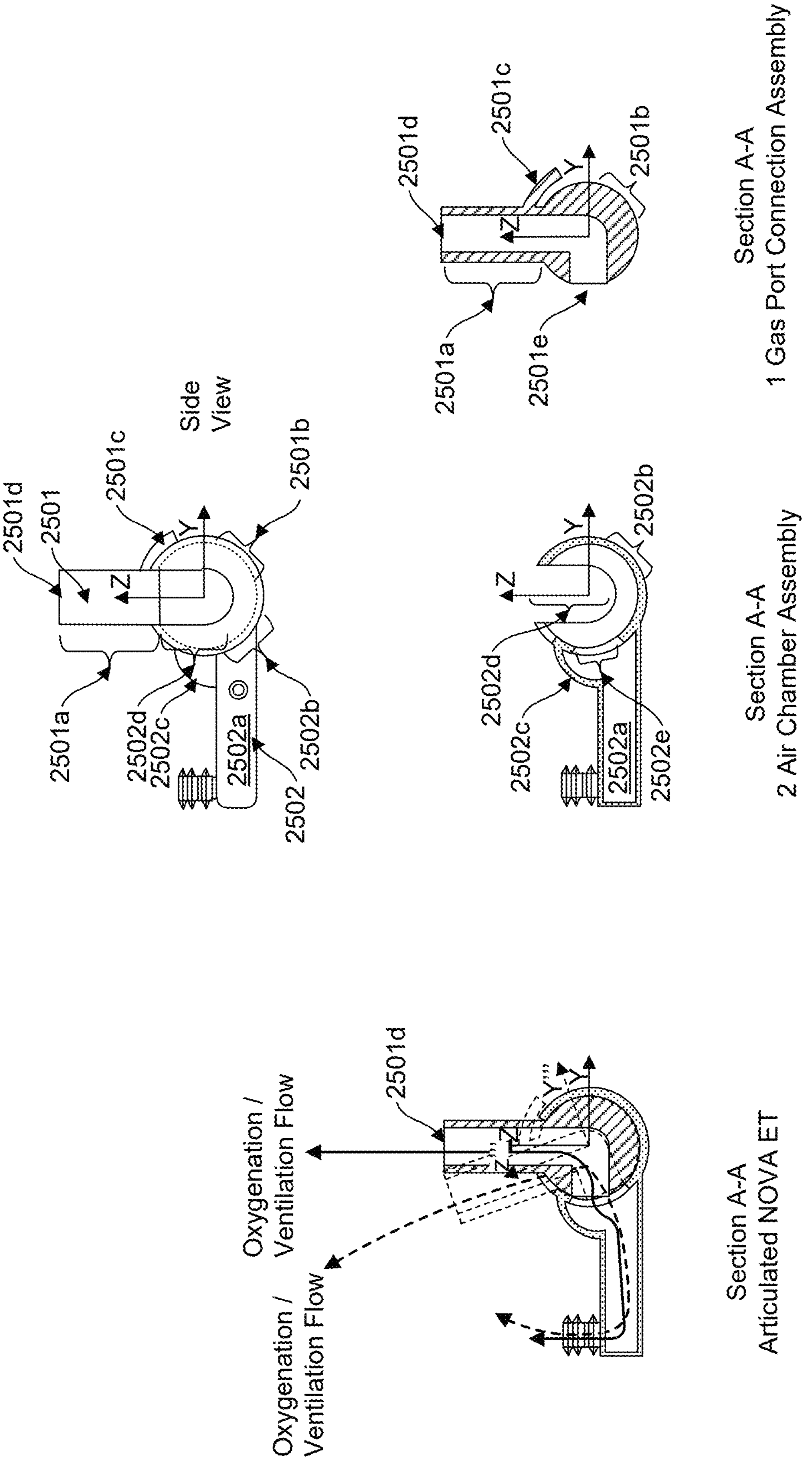
FIG. 26 illustrates section A-A of the articulated appliance of FIG. 25.

As shown in the section views of FIG. 26 and FIG. 27, the socket-chamber opening 2502*f* may be part of the socket 2502*b* and allows for gas to flow between the chamber 2502 and the ball 2501*b* through the air dome. 2502*c*. An oval-like perimeter of the opening 2502*f* can have the same radius as the socket 2502*b*, be slightly raised in order to accomplish a seal, or have a rubberized flexible consistency in order to support a seal between the socket 2502*b* and the ball 2501*b*.

A *Columella-Philtrum* to nasal respiratory apparatus interface 2502*g* is a cushioned mechanical interface between the nasal respiratory apparatus and the patient's forehead. One or two nares ports 2503 provide the mechanical and gas flow interface between the patient's nares and the articulated nasal respiratory apparatus. The outer portion of the nares port 2503 provides a pressure seal in order to contain airflow between the patient's nasal pharynx and the articulated nasal respiratory apparatus.

The portend tidal sample port 2504 is an optional interface allowing for sampling of the end tidal $CO_2$ level from nasal exhalation by a sampling device such as a Capnography Sensor (not shown). The port exterior is a standard luer lock connector that interfaces with a sampling line per ISO 80396-7: 2016(E) or current equivalent. A male or female connector can be implemented, a female interface is shown in the illustration. Alternate interfaces can also exist. The end tidal port can be on the plus or minus X-axis side of the air chamber.

A supplementary $O_2$ port 2505 may extend from the air chamber assembly 2502. The supplementary $O_2$ port 2505 interfaces with an oxygen supply line (not shown) and allows for additional oxygen to be provided to the patient via a wall or other oxygen supply source (not shown). the supplementary $O_2$ port can be on the plus or minus X-axis side of the air chamber assemble 2502.

Figure 29:
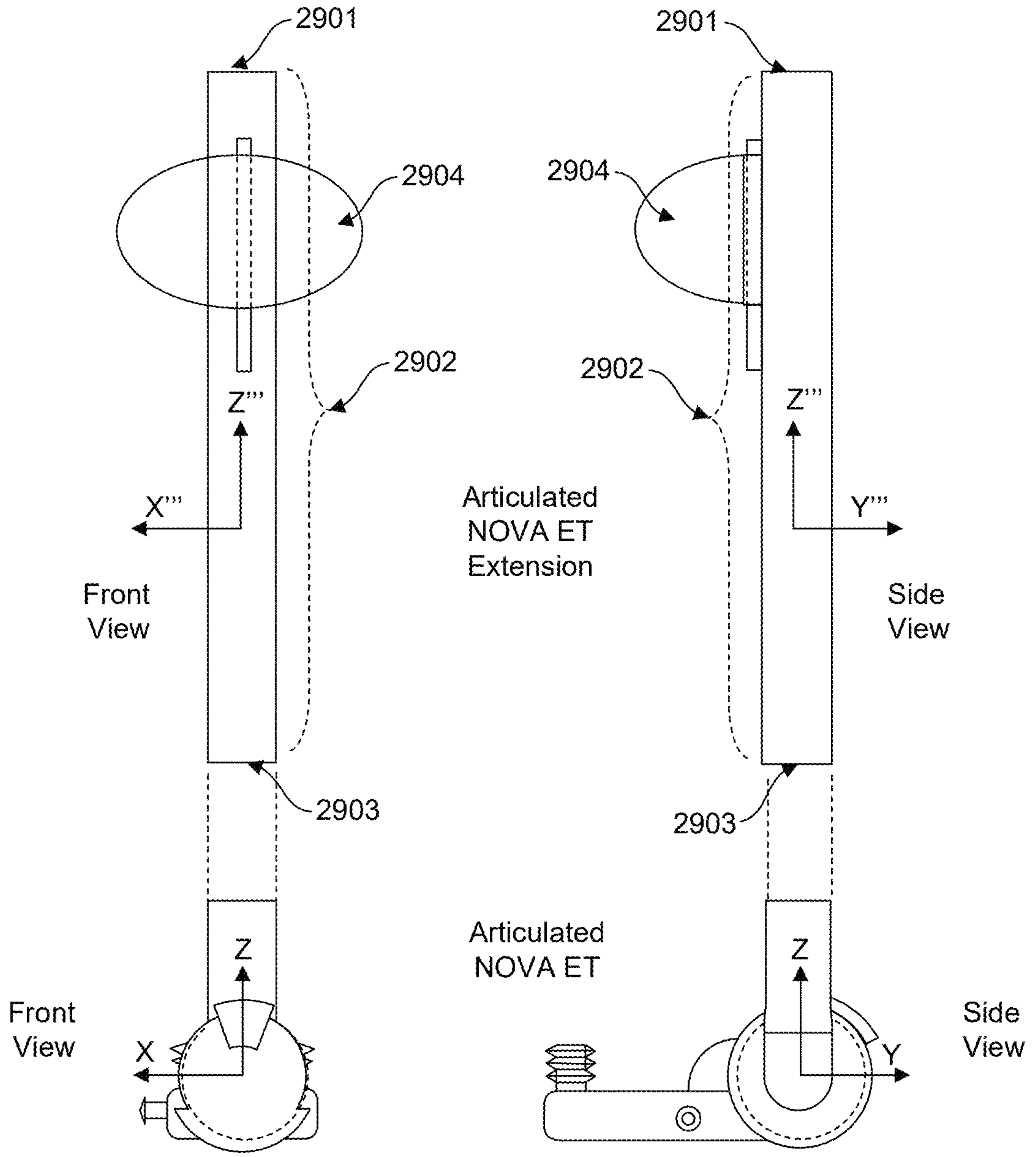
FIG. 29 illustrates an articulated extension of a nasal respiratory apparatus.

An articulated nasal respiratory apparatus extension 2900, as illustrated in FIG. 29, may be used to avoid contact with a patient's eyes when the articulated nasal respiratory apparatus is utilized with the gas port connection assembly 2501 nominally aligned with the Z-axis. The articulated nasal respiratory apparatus Extension illustrated in FIG. 29 provides virtually all of the same functions as the nasal respiratory apparatus described herein.

Gas connection port entrance 2901 provides an interface with standard $O_2$ source, anesthesia machine, hyper-inflation bag, high-flow source or ventilator, which may be via an 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. The gas supply tube 2902 is a conduit containing and allowing for the flow of gas between the gas connection port and the air chamber. Gas connection port exit 2903 provides an interface with the gas supply channel of the articulated nasal respiratory apparatus. This port is designed to fit male or female connectors. A female connection interface is shown on this illustration. The forehead standoff 2904 is a cushioned mechanical interface between the nasal respiratory apparatus and the patient's forehead. Additionally, the forehead standoff provides space between the gas supply tube and forehead allowing various connectors to connect to the tube without interference from the forehead. The rail 2904*a* is an optional configuration in which the rail is part of the gas supply tube. In this configuration, the forehead standoff 2904 may be separate from the gas supply tube, constrained by the rail in the X and Y directions, but can slide along the Z-axis, allowing the forehead standoff 2904 to be centered on the patient's forehead. This allows the apparatus to accommodate a wide range of patient head sizes. The rail can be either rigid or extendable. Being able to expand or contract the rail accommodates head movement from side to side, up and down, and rotation.

Figure 30:
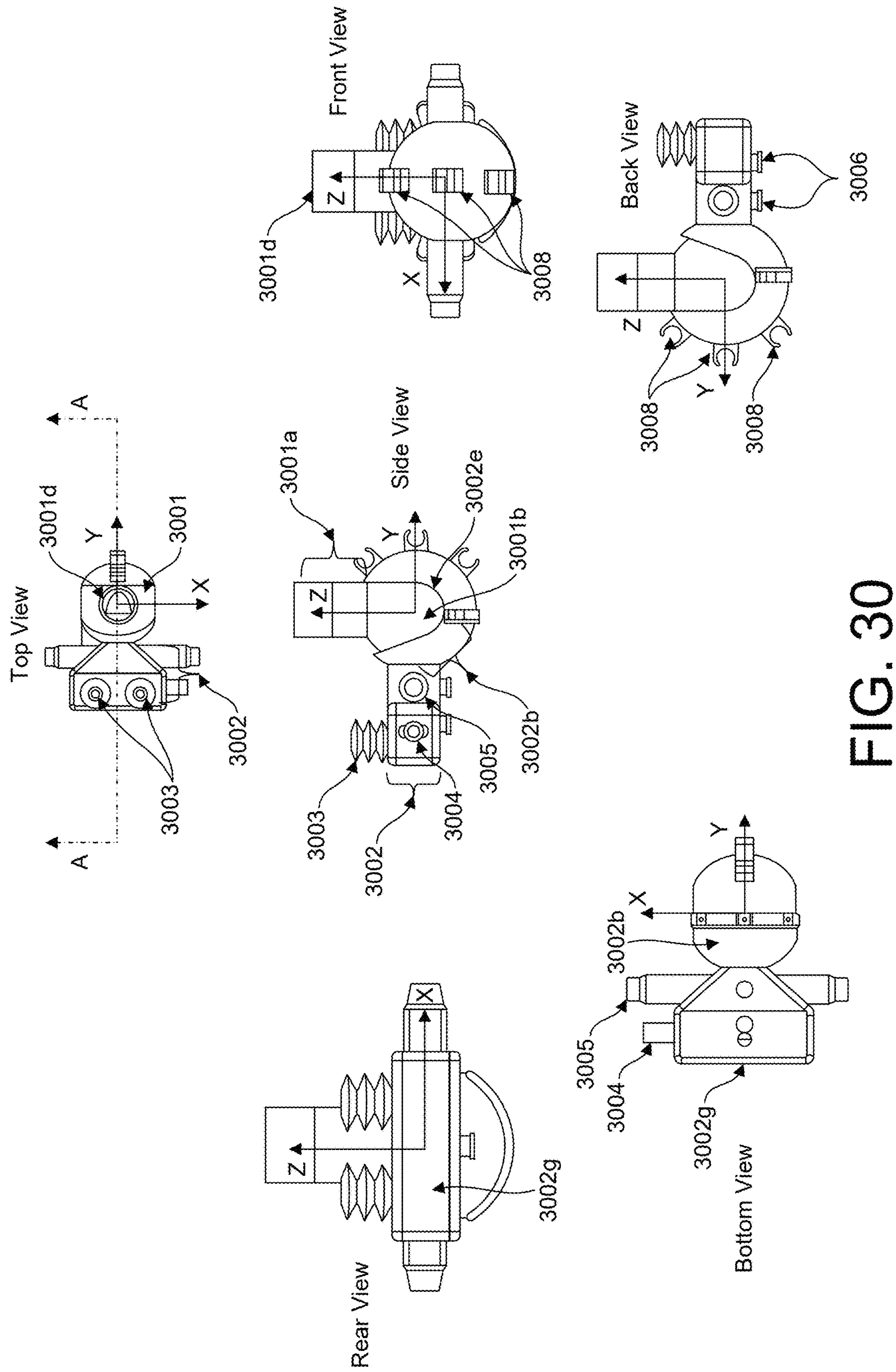
FIG. 30 illustrates an articulated nasal respiratory apparatus

An embodiment of the articulated nasal respiratory apparatus illustrated in FIG. 30 includes an air chamber assembly 3002 and a gas connection port assembly 3001. Detail for the cross-section A-A noted in the Top View of FIG. 30 is provided in FIG. 32. The cross-section A-A looks down the X-axis of gas connection port assembly 3001 and the air chamber assembly 3002. An exploded view of the articulated nasal respiratory apparatus is provided in FIG. 31. In this embodiment, the gas connection port assembly 3001 can rotate from 0° to approximately 20° about the X-axis and +/−90° about the Y-axis. With the gas connection port assembly 3001 rotated 0° to 20° about the X-axis and 0° about the Y-axis, as illustrated in FIG. 33, With the gas connection port assembly 3001 supports oxygenation and ventilation of a patient in the same manner as the nasal respiratory apparatus, FIG. 2, where the gas flows through a tube that is nominally in line with the nose and forehead of the patient. With the gas connection port assembly 3001 rotated 0° the X-axis and +/−90° about the Y-axis, oxygenation and ventilation can be provided with gas flow occurring from the right or left side of the patient. The articulated nasal respiratory apparatus could interface with the oral end tidal (ET) Attachment described herein, supporting either or both nasal and oral end tidal $CO_2$ sampling.

gas port connection 3001 is one of two assemblies making up the articulated nasal respiratory apparatus that provides the interface with external gas supply and ventilation systems (not shown). gas supply channel 3001*a* is a conduit containing and allowing for the flow of gas between the gas connection port assembly 3001 and the air chamber assembly 3002. gas connectors (not shown) attach to this portion of the assembly. With the entrance port 3001*d* at the top of the channel, it will interface with a standard $O_2$ source, anesthesia machine, hyper-inflation bag, high-flow source or ventilator (not shown) via 8.5 mm, 11.5 mm, 15 mm or 22 mm conical connectors as defined by ISO 5356 or current equivalent standard. Other connector interfaces are possible. This port is designed to interface with male or female connectors. A male connection interface is shown on this illustration.

The gas supply channel 3001*a* terminates into the ball 3001*b*. Internal to the ball is a channel for gas flow with a cross section of an L or elbow. gas flows out the exit port 3001*e* nominally at a 90° angle to the entrance flow direction. The ball 3001*b* interfaces with the socket 3002*b* of the air chamber assembly 3002, creating a substantially leak-free seal due to mechanical force conforming the ball surface to the socket surface. air flows between the gas port connection assembly 3001 and the air chamber assembly 3002 through the socket-chamber opening 3002*f*, which may be part of the socket 3002*b*. In order to keep the ball exit port 3001*e* within the boundary of the socket-chamber opening 3002*f*, required for gas flow, a Z-axis rotation retainer 3001*c* prevents the gas port connection assembly 3001 from rotating about the Z-axis of the gas supply channel 3001*a*. The retainer includes a Z-axis rotation retainer opening located on the ball 3001*b* and a Z-axis rotation retainer pin located in the shell. The ball rotation is limited by the pin running into the edges of the opening. It is possible to have the opening in the shell and the pin in the ball.

The entrance port 3001*d* is at the top of the gas supply channel that interfaces with external gas supply and ventilation devices. The exit port 3001*e*, illustrated in FIG. 31, is where gas flows from the gas port connection assembly 3001 to the air chamber assembly 3002, or vice versa. The perimeter of the exit can be a circular or nominally oval cross section and could be slightly raised radially outward from the ball 3001*b*, have a rubber coating or a seal illustrated as an option in order to improve the gas seal against an interface with the socket 3002*b*, where it rests.

The air chamber assembly 3002 is one of the assemblies making up the articulated nasal respiratory apparatus and provides the structural and gas flow interface between the gas port connection assembly 3001, at least one nares ports 3003 and an end tidal sampling port 3004. A chamber 3002*a* mechanically supports the nares ports, the end tidal sample port 3004 and is the gas flow channel between an opening of the ball 3001*b* and the nares ports 3003.

The socket 3002*b* provides the mechanical support and sealing interface with the ball. Note that there is a front and rear half as indicated in FIG. 31. The halves can be bonded or in this illustration, snapped together by male connectors, 3002*j*, that protrude through the female connector holes,

3002*k*. The air dome (not shown) is not required for the present embodiment, but may be used.

The port slot 3002*d*/3002*e* on either side of the socket runs parallel to the Z-axis and allows the gas port connection assembly to be rotated about the Y-axis +/−90° or any other desired angle. The X-axis port slot 3002 allows the gas port connection assembly to be rotated about the X-axis from 0° to approximately 20°. Note the articulated nasal respiratory apparatus Et can rotate approximately 20° about the X-axis for any Y-axis rotation from −90° to 90° or any other desired angle if the X-axis port slot is enlarged about the Y-axis to accommodate the additional range.

Figure 32:
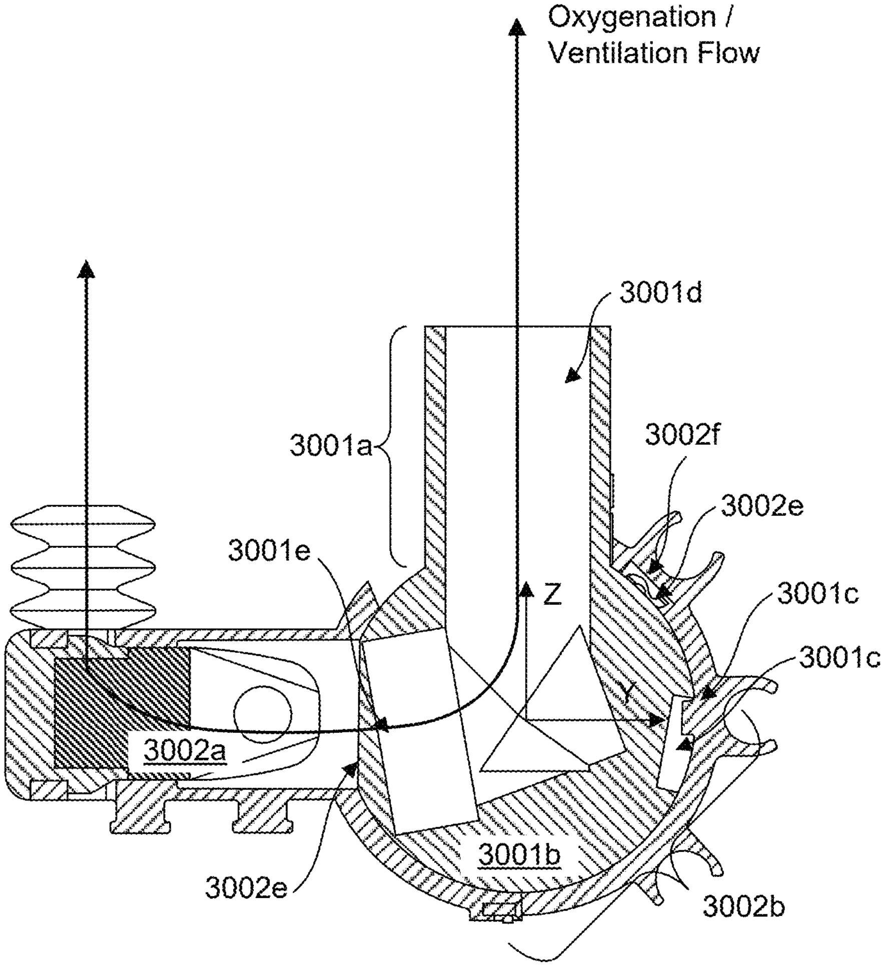
FIG. 32 illustrates section A-A of FIG. 30
Figure 33:
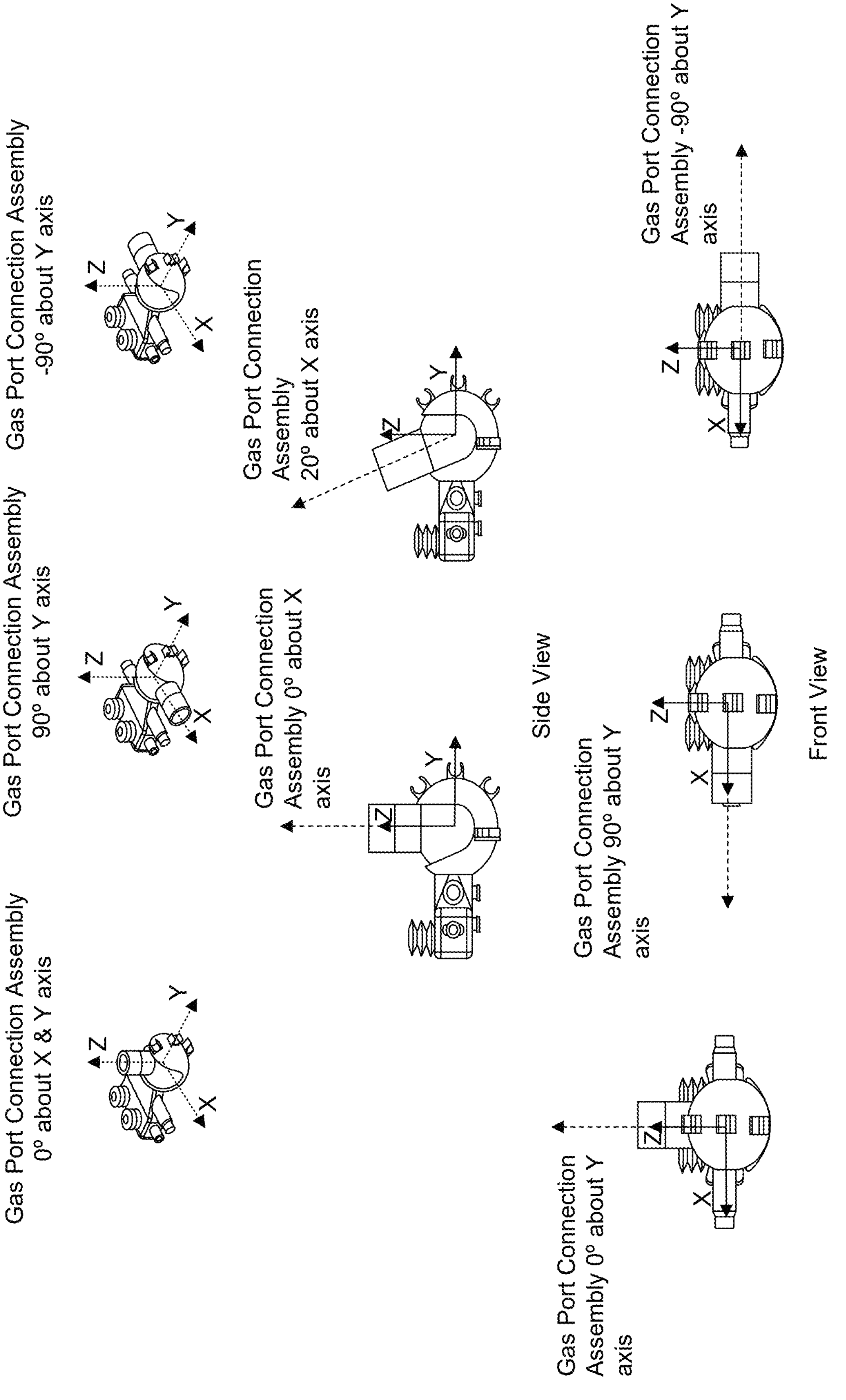
FIG. 33 illustrates rotation of an articulated gas port connection assembly.

Shown in the section views of FIG. 32 and in FIG. 31, The socket-chamber opening 3002*f* is part of the socket and allows for gas to flow between the chamber and the ball through the air dome. The darkened oval-like perimeter of the opening can have the same radius as the socket, be slightly raised in order to accomplish a seal, or have a rubberized flexible consistency in order to support a seal between the socket and the ball.

The *Columella-Philtrum* to nasal respiratory apparatus interface 3002*g* is a cushioned mechanical interface between the nasal respiratory apparatus and the patient's forehead.

A ball compression spring shell recess 3002*h* is placed in the shell 3002*b*, that accepts a compression spring. When the two halves of the shell are assembled, the spring, 2*i*, is compressed, pushing against the ball, 1B, and sealing the ball against the shell to prevent gas leakage.

The ball compression spring 3002*i* provides the sealing force for the ball against the socket when compressed in the recess, 3002*h*. The male connector mates 3002*j* with the female connector on the opposite half of the shell when the two halves are assembled. One or two nares ports 3003 provide the mechanical and gas flow interface between the nares and the articulated nasal respiratory apparatus. The outer portion of the nares port provides a pressure seal in order to contain airflow between the nasal pharynx and the articulated nasal respiratory apparatus. Note the nares port can point in the Z direction as shown or can be tilted slightly about the X or Y-axis to result in better nasal flow and or to secure better to the nose.

The portend tidal sample port 3004 is an optional interface allowing for sampling of the end tidal $CO_2$ level from nasal exhalation by a sampling device such as a Capnography Sensor. The port exterior is a standard luer lock connector that interfaces with a sampling line per ISO 80396-7: 2016(E) or current equivalent. A male or female connector can be implemented, a female interface is shown in the illustration. Alternate interfaces can also exist. Note the end tidal port can be on the plus or minus X-axis side of the air chamber.

A supplementary $O_2$ port 3004 extends from the air chamber. It interfaces with an oxygen supply line (not shown) and allows for additional oxygen to be provided to the patient via a wall or other oxygen supply source. The supplementary $O_2$ port 3004 can be on the plus or minus X-axis side of the air chamber assembly 3002.

Figure 36:
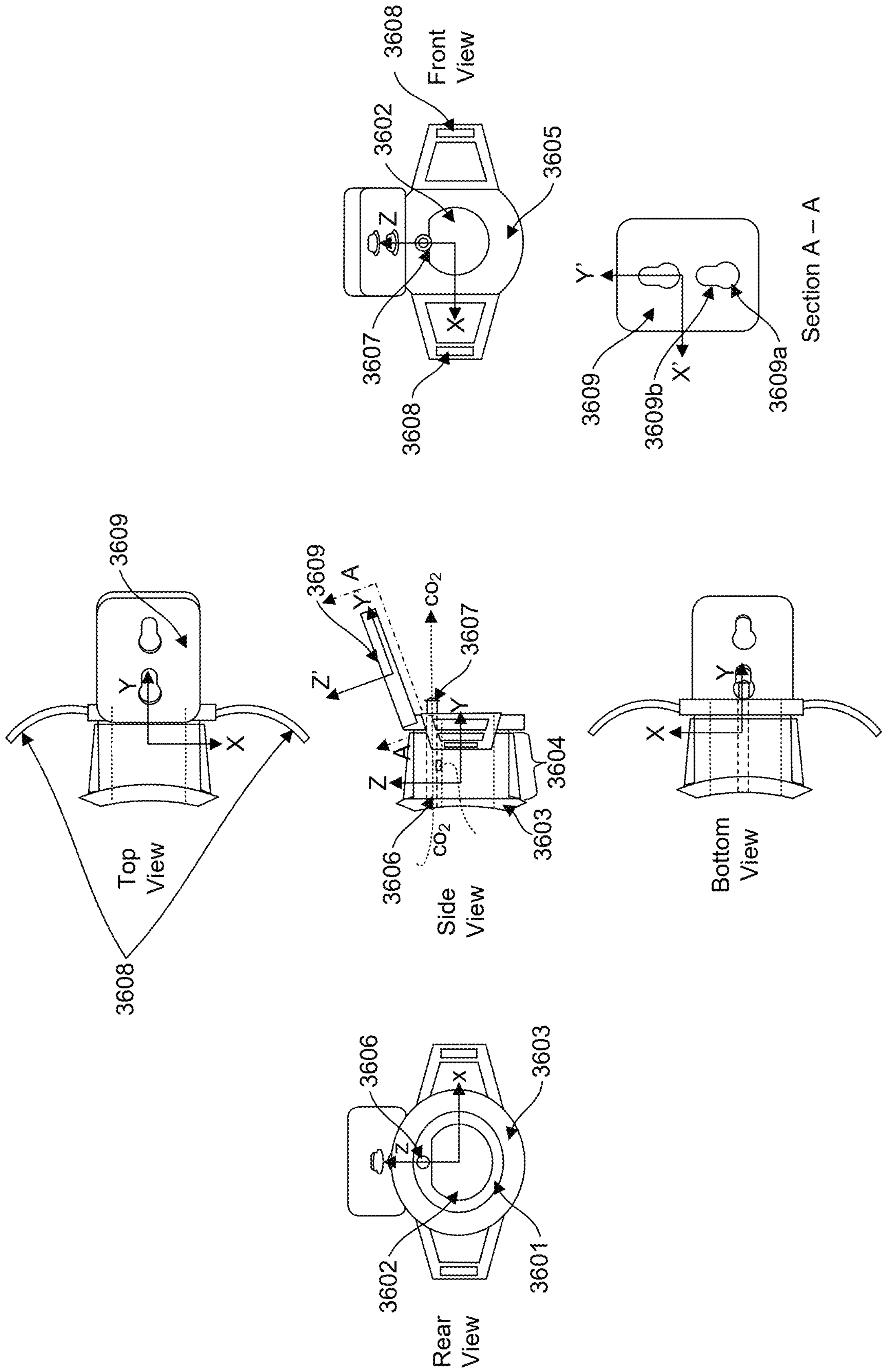
FIG. 36 illustrates a bite block.
Figure 37:
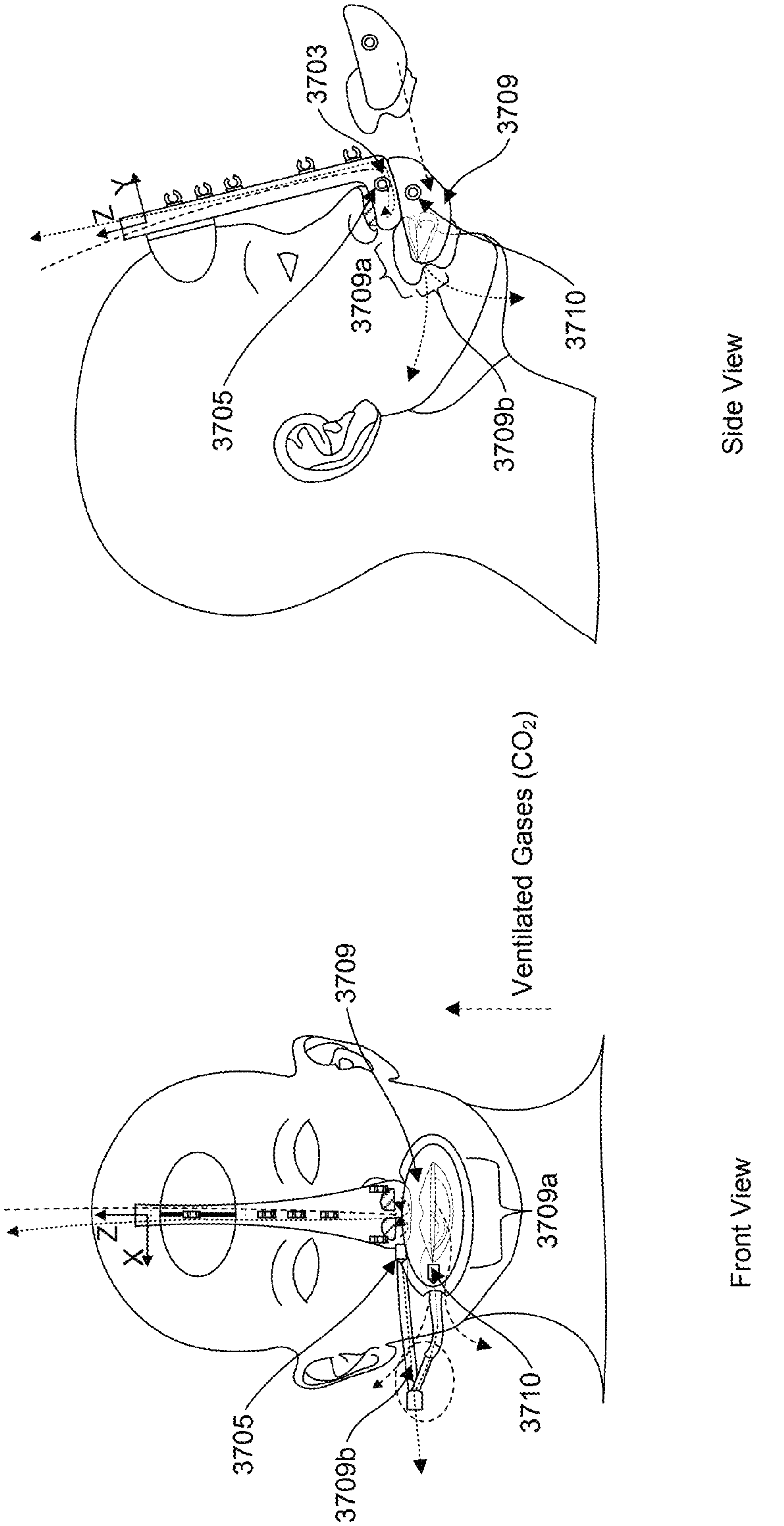
FIG. 37 illustrates an oral end tidal attachment.
Figure 38:
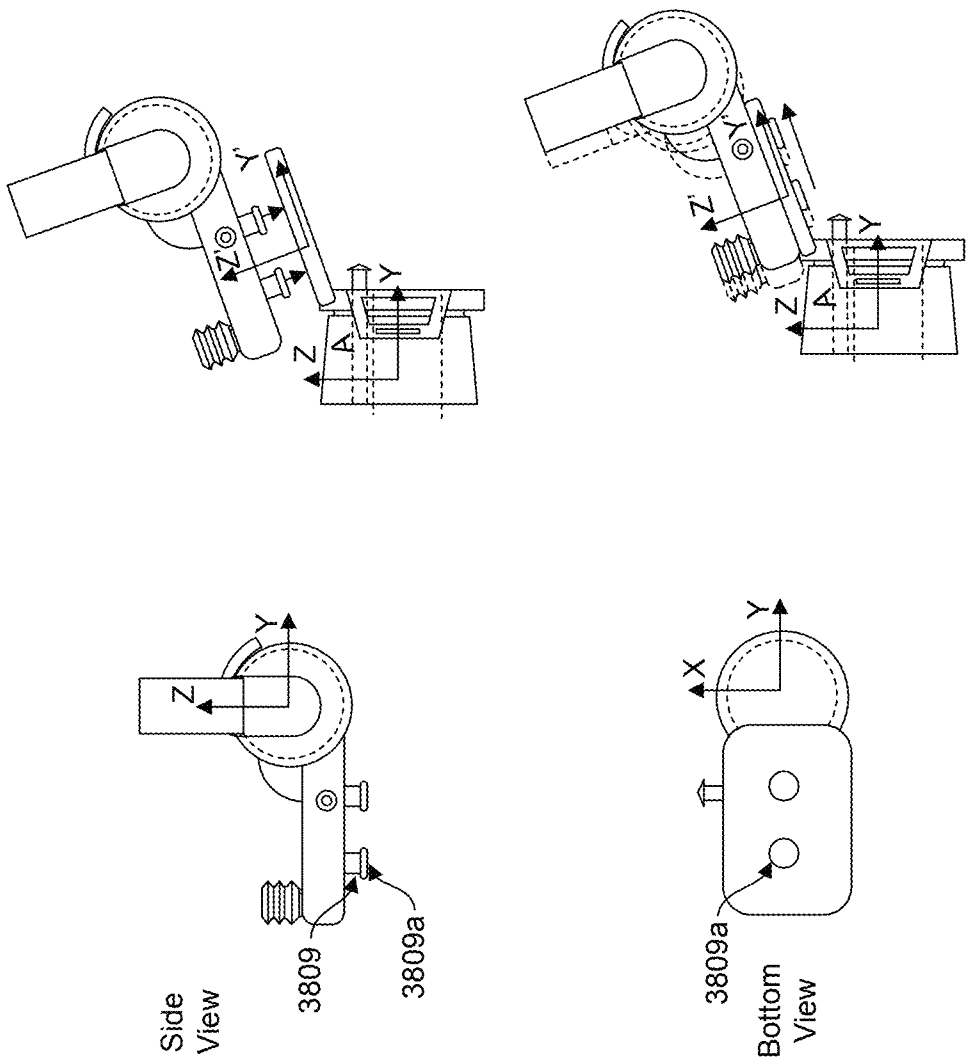
FIG. 38 illustrates integration of the bite block of FIG. 36.

Nasal respiratory apparatus connection pins 3006 shown in FIG. 30 allow for the connection of ancillary items to the nasal respiratory apparatus such as an oral ET shown in FIG. 37 or the bite block shown in FIG. 36 and FIG. 38.

The head strap connectors 3008 shown in FIG. 30 allow for connecting head straps such as those shown in FIG. 60, FIG. 61, FIG. 62, and FIG. 63 to the articulated nasal respiratory apparatus. Any of the head strap configurations shown in FIGS. 60-74 may be used with any of the nasal apparatuses disclosed herein, without limitation. The head strap connectors shown herein may be used with any of the nasal respiratory apparatuses described herein, with particular reference to FIGS. 21 and 22.

Figure 34:
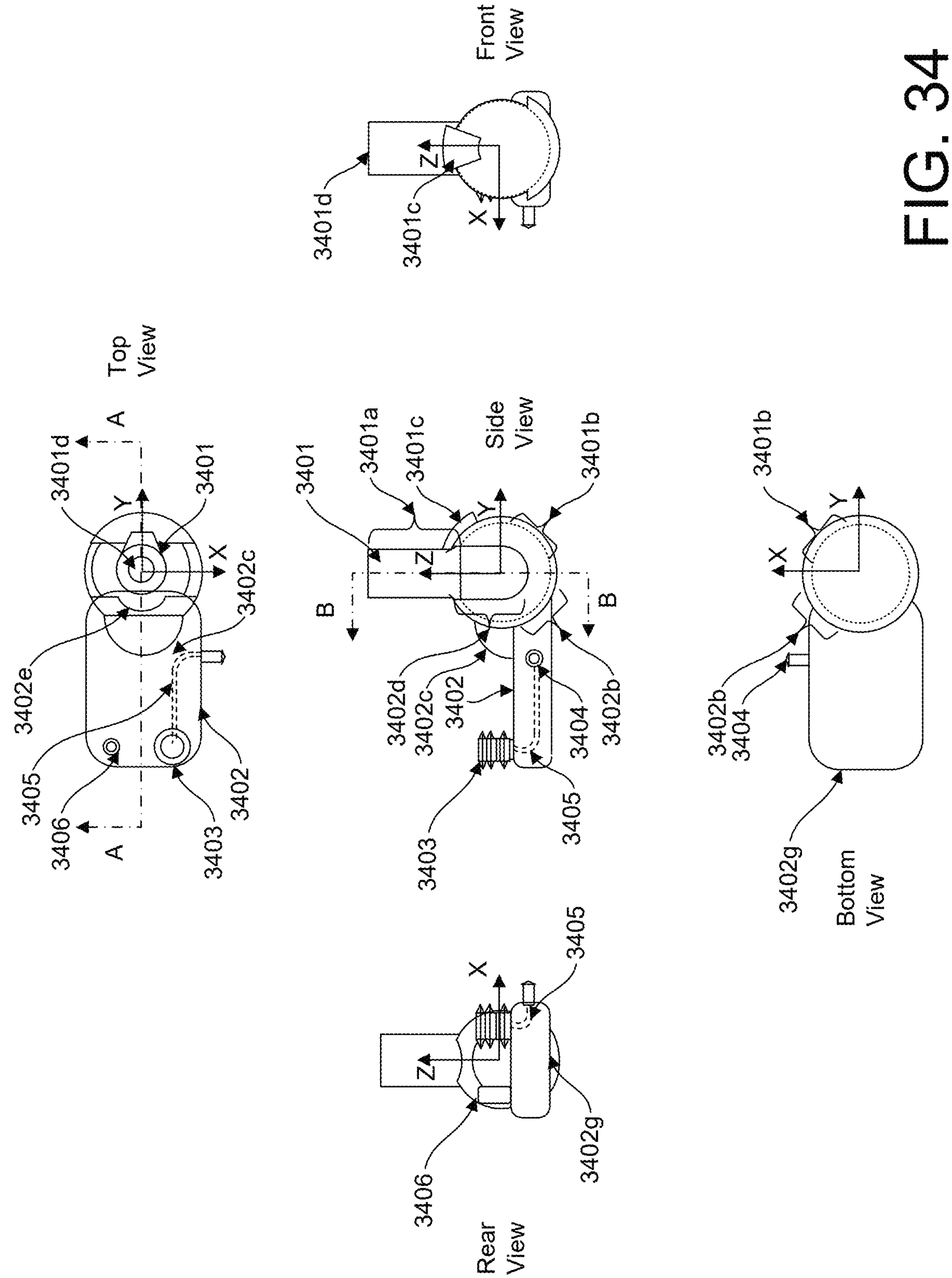
FIG. 34 an embodiment a nasal respiratory apparatus with high flow nasal cannula configuration.
Figure 35:
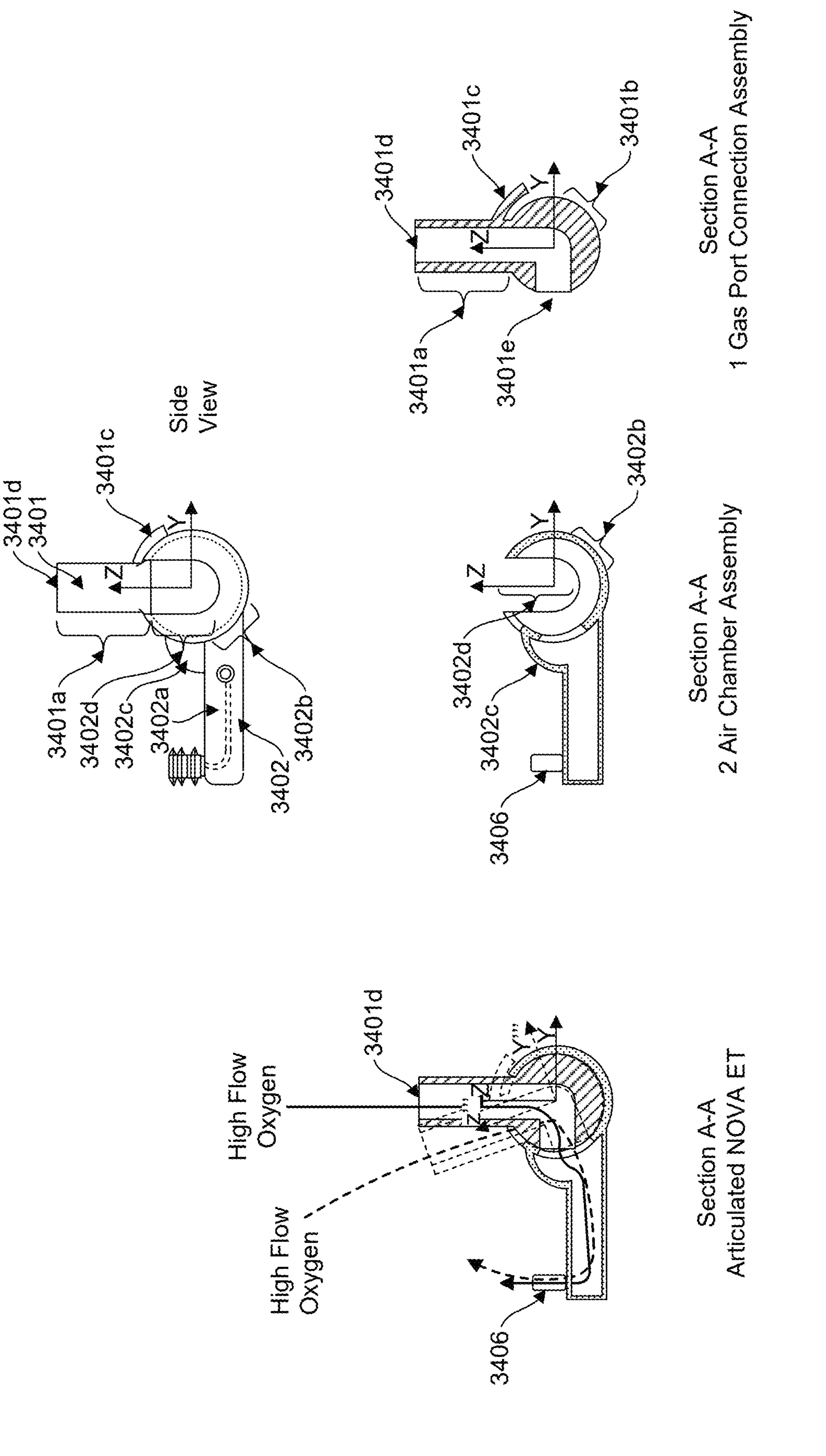
FIG. 35 illustrates section A-A of the embodiment of FIG. 34.

An embodiment of a high-flow articulated nasal respiratory apparatus is illustrated in FIG. 34, with the section A-A cross-section shown in FIG. 35. A difference in this configuration with both the nasal respiratory apparatus and articulated nasal respiratory apparatus configurations is that one of the nares ports 3403 has been replaced with a high-flow nasal cannula 3406. The remaining nares port 3403 still seals the patient's nares and is connected by a tube to the portend tidal sample port 3404, allowing for end tidal $CO_2$ sampling while providing high-flow oxygenation. Sampling for end tidal $CO_2$ is not possible with known high-flow systems such as the Optiflow™ system manufactured by Fisher Paykel, or the Precision Flow system from Vapotherm. This is due to $CO_2$ present in exhalation from both nares being washed out by the continuous oxygen flow. The high-flow articulated nasal respiratory apparatus configuration isolates one of the nares from the oxygen flow, preventing the signal from being washed out. High flow is typically defined as an oxygen flow rate of up to 40 l/min. The nasal canula configuration/single nares port configuration may be applied to a non-articulated nasal respiratory apparatus, as described herein, starting with FIG. 1 and FIG. 2 et seq.

The nasal cannula port 3406 in the high-flow articulated nasal respiratory apparatus configuration is not sealed, so air pressure adjacent to the port is nominally at the same pressure as the atmosphere. Any pressure internal to the nasal cavity cause by the high flow is the static head created by the flow. The nares port 3403 is sealed relative to the atmosphere, and pressure at this port in the nares is due to patient exhalation. Exhaled gas flows through a nares port-end tidal sampling port connector It is then collected by a sample line (not shown) connected to the portend tidal sample port 3404 and a capnography sensor (not shown).

This high-flow gas cannula and end-tidal sampling configuration could be utilized by the nasal respiratory apparatus configuration shown in FIG. 2.

oral exhalation could be collected by the high-articulated nasal respiratory apparatus configuration utilizing an oral end-Tidal Attachment shown in FIG. 37. Straps may secure the high-flow articulated nasal respiratory apparatus to the patient's head shown in FIG. 62 or FIG. 63 could be utilized.

gas port connection 3401 is one of two assemblies making up the High-Flow articulated nasal respiratory apparatus. It provides the interface with external gas supply and ventilation systems. The gas supply channel 3401*a* is a conduit containing and allowing for the flow of gas between the gas connection port assembly and the air chamber assembly. Gas connectors attach to this portion of the assembly. With the entrance port at the top of the channel. It will interface with a high-flow source connector or 8.5 mm, 11.5 mm, 15 mm or 22 mm conical connectors as defined by ISO 5356 or current equivalent standard. Other connector interfaces are possible. This assembly is composed of several sub-elements. This port is designed to interface with male or female connectors. A male connection interface is shown on this illustration.

The gas supply channel 3401*a* terminates into the ball 3401*b*. Internal to the ball 3401*b* is a channel for gas flow with a cross section of an L or elbow. gas flows out the exit port 3401*e* nominally at a 90° angle to the entrance flow direction. The ball 3401*b* interfaces with the socket 3402*b* of the air chamber assembly 3402, creating a substantially leak-free seal due to mechanical force conforming the ball surface to the socket surface. Air flows between the gas port connection assembly 3401 and the air chamber assembly 3402 through the socket-chamber opening 3402*f*, which may be part of the socket 3402*b*.

In order to keep the ball exit port within the boundary of the socket-chamber opening, required for gas flow, the Z-axis rotation retainer 3401*c* prevents the gas port connection assembly from rotating about the Z-axis of the gas supply channel.

The entrance port 3401*d* is at the top of the gas supply channel that interfaces with external gas supply and ventilation devices. The exit port 3401*e* is where gas flows from the gas port connection assembly to the air chamber assembly, or vice versa.

The air chamber assembly 3402 is one of the assemblies making up the articulated nasal respiratory apparatus. It provides the structural and gas flow interface between the gas port connection assembly 3401, at least one nares port 3403 and an end tidal sampling port 3404. The chamber 3402*a* may mechanically support the nares port 3403, the High Flow nasal Cannula 3406, the end tidal sample port 3404 and is the gas flow channel between an opening of the ball 3401*b* and the High Flow nasal Cannula 3406. The socket 3402*b* provides the mechanical support and sealing interface with the ball 3401*b*. The air dome 3402*c* contains gas flow from the atmosphere and provides a volumetric space for unhindered gas flow from the ball exit port 3401*e*, through the socket-chamber opening 3002*f* to the air chamber assembly 3002. The port slot 3402*d*/3402*e* on either side of the socket runs parallel to the Z-axis and allows the gas port connection assembly to be rotated about the Y-axis +/−90°.

The X-axis port 3402*e* slot allows the gas port connection assembly to be rotated about the X-axis from 0° to approximately 20°. Shown in the section views of FIG. 35, The socket-chamber opening 3402*f* is part of the socket and allows for gas to flow between the air chamber assembly 3402 and the ball 3401*b* through the air dome 3402*c*. An oval-like perimeter of the opening can have the same radius as the socket 3402*b*, be slightly raised in order to accomplish a seal, or have a rubberized flexible consistency in order to support a seal between the socket 3402*b* and the ball 3401*b*.

The *Columella-Philtrum* to nasal respiratory device interface 3402*g* is a cushioned mechanical interface between the nasal respiratory apparatus and the patient's forehead. One nares port 3403 provides the mechanical and gas flow interface between the nares and the portend tidal sample port 3404. The outer portion of the nares port 3403 provides a pressure seal in order to contain airflow between the nasal pharynx and the articulated nasal respiratory apparatus. The port can be placed to interface with the left or right nares. The portend tidal sample port 3404 is an optional interface allowing for sampling of the end tidal $CO_2$ level from nasal exhalation by a sampling device such as a Capnography Sensor (not shown). The port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port 3404 can be on the plus or minus X-axis side of the air chamber assembly 3402.

The nares port-portend tidal sample port connector 3405 provides a sealed gas flow path between the nares port 3403 and portend tidal sample port 3404 for gas entering the patient's nares due to exhalation. The end tidal sample port 3403 can be on the plus or minus X-axis side of the air chamber assembly 3402. The High Flow nasal Cannula port 3406 provides the mechanical and gas flow interface between the patient's nares and gas flowing from the air chamber assembly 3402. The cannula port 3406 is not sealed against the patient's nares wall and the pressure adjacent to the cannula is at atmospheric pressure. Any pressure due to the high gas flow is due to the static pressure associated with the gas flow rate. The nares port be placed to interface with the left or right nares.

Figure 39:
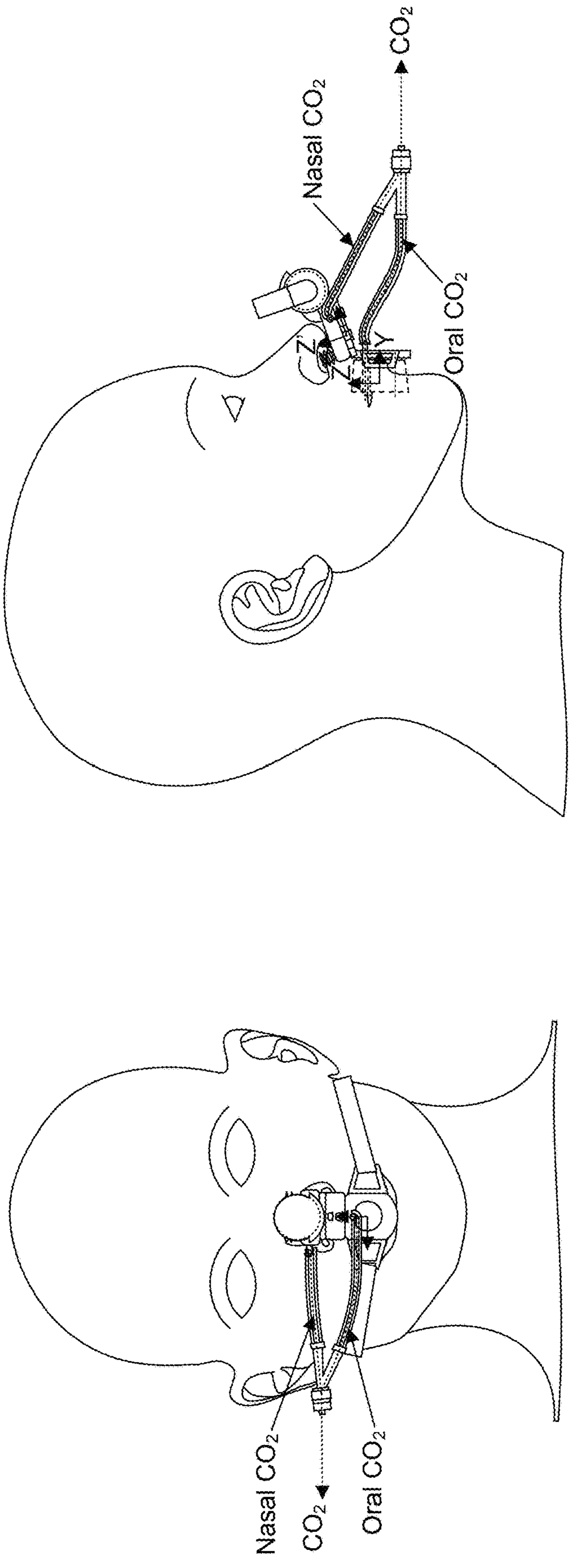
FIG. 39 illustrates a nasal respiratory apparatus with nasal-oral end tidal connection.

Bite Blocks providing oral access are currently used for patients undergoing anesthesia when the option of using an intubation tube is desired. FIG. 36 provides an illustration for the bite block that integrates with the nasal respiratory apparatus or articulated nasal respiratory apparatus when the addition of nasal oxygenation and ventilation is also desired. A method of integrating the bite block with the articulated nasal respiratory apparatus is illustrated in FIG. 38. The method of securing the bite block and articulated nasal respiratory apparatus strapped to a patient's head is illustrated in FIG. 39. The sampling of nasal and oral $CO_2$ may flow from the articulated nasal respiratory apparatus and bite block into a Y connector where a single line flows onto a capnograph sensor or another device, as shown in FIG. 39.

In this configuration, a bite block tube 3601 is inserted into the patient's mouth holding it open. A compliant tube cover 3604 surrounds the perimeter of the tube 3601 to cushion the patient's teeth. The center of the tube 3601 is hollow, allowing for oral access required for placing an intubation tube (not shown). The left and right side of the bite block 3600 along the X-axis has a head strap connector that interfaces with a head strap that loops through the opening. The nasal respiratory apparatus or articulated nasal respiratory apparatus interfaces with the bite block 3600 by connecting to the +Z' surface of a nasal respiratory apparatus interface shelf 3610. The $CO_2$ waveform from the end tidal exhalation can be accomplished with the bite block 3600 by attaching a capnograph sensor sample line (not shown) to the portend tidal sample port tube 3607 and drawing an oral gas sample from the mouth interior through the bite block tube 3601.

The bite block tube 3601 provides the oral access along the Y-axis of the device and allows for breathing through the mouth. Inserted into the patient's mouth, it provides the structural integrity for the device when clamped on by the patient's teeth. The oral Access opening 3602 is the open region inside the bite block tube 3601. It allows for gas flow during breathing as well as external access for placing an intubation tube or other device. A bite block internal rim 3603, located on the −Y face of the bite block tube 3601, provides a dental catch that prevents the bite block device 3600 from slipping along the Y-axis when the teeth are closed around it. A rear oral access opening is at its nominal center. The compliant tube cover 3604 may wrap around the external side of the bite block tube along the Y-axis. It cushions the teeth when clamping the bite block.

The bite block face 3605 is the structural element that interfaces to the +Y-axis of the bite block tube 3601 and left and right head strap connectors 3608. The front oral access opening 3602 is at its nominal center. A $CO_2$ Sampling channel 3606 is an opening that runs through the wall of the bite block tube 3601 along the Y-axis. The entrance of the bite block tube 3601 can exist either on the −Y face, and or the interior of the bite block tube 3601. The $CO_2$ Sampling channel 3606 terminates on the +Y face of the bite block tube 3601 where it interfaces with an portend tidal sample port 3607. The purpose of the channel is to allow for sampling of exhaled $CO_2$ gas from the oral cavity.

The portend tidal sample port 3607 is an optional interface allowing for sampling of the end tidal $CO_2$ level from oral exhalation travelling through the $CO_2$ Sampling channel 3606 by a sampling device such as a Capnography Sensor (not shown). The port exterior may be a standard luer lock connector that interfaces with a sampling line per ISO 80396-7: 2016(E) or current equivalent. A male or female connector can be implemented, a female interface is shown in the illustration. Alternate interfaces can also exist. The portend tidal sample port 3607 can be placed anywhere on the face of the X-Z plane.

Head strap connector 3809 and a head strap secures the bite block to the patient. An elastic strap that runs behind the patient's head as shown in FIG. 39 attaches to the right and left connector. A vertical slot parallel to the Z-axis is one location where the strap can loop through for attachment.

Articulated nasal respiratory apparatus connection pin 3809, as shown in FIG. 38 may be one or more (as shown two) nasal respiratory apparatus connection pins 3809 located on the Z face of the articulated nasal respiratory apparatus (or non-articulated device) to attach to the bite block nasal respiratory apparatus interface shelf 3609. The connection pin 3809 may include a pin cap 3809*a* on top of a narrower pin.

Both the nasal respiratory apparatus and articulated nasal respiratory apparatus can attach to the bite block via the nasal respiratory apparatus interface shelf 3610. One or more (as shown two) pin openings and pin lock slots through the X'-Y' surface accept pins attached to the nasal respiratory apparatus or articulated nasal respiratory apparatus. pins on the articulated nasal respiratory apparatus as well as the two steps required for integration are shown in FIG. 38.

The pin opening 3610*a* diameter is larger than the pin cap and allows the pins to be inserted into the openings. pin portion of the connection pin slides down the pin lock slot 3610*b* with until it locks into place on the interface shelf 3609. The pin portion of the device may be used to attach other modular components to the nasal respiratory apparatus or the articulated nasal respiratory apparatus. As illustrated in FIG. 37, an oral end tidal (ET) attachment 3709 may be fitted on the pins of the nasal respiratory device. As illustrated, the oral end tidal attachment 3709 connects to the lower outside surface of the air chamber. The oral ET attachment seals the mouth, except for a ventilation gap (3709*b*) in the flexible seal (3709*a*), where gases exhaust to the atmosphere. The oral end tidal attachment 3709 allows for capture of ventilated gas for $CO_2$, $O_2$, and other gas sampling orally. FIG. 37 shows an air chamber 3703 to provides the structural and gas flow interface between a gas supply tube, at least one nares ports and an end tidal sampling port 3710. The portend tidal sample port 3710 is an optional interface allowing for sampling of the end tidal $O_2$, and other gas levels from nasal exhalation by a sampling device such as a Capnography Sensor (not shown). The portend tidal sample port 3710 exterior may be a standard luer lock or other connector that interfaces with a sampling line per ISO 80396-7: 2016(E) or current equivalent. Alternate interfaces can also exist. It is envisioned that in this configuration, the sample line from the nasal respiratory apparatus may interface with one of two ports in a Y connector and then continues to the sensor through a single sample line.

The oral ET attachment 3709 may be relatively rigid and clip onto the lower outer surface of the nasal respiratory apparatus air chamber using the pins shown in, for example, FIG. 38. A flexible seal 3709*a* surrounds the perimeter of the oral ET attachment 3709 and conforms to the perimeter of the mouth, forming an air seal when the oral Attachment 3709 is secured to the air chamber. A ventilation gap 3709*b* in the flexible seal 3709*a* may be provided in order to allow flow from oral exhalation to exhaust to the atmosphere. It is located near the portend tidal sample port 3710, downstream, in order for gas to flow past the portend tidal sample port (10) in order to be sampled. The ventilation gap 3709*a* can be on the plus or minus X-axis side of the oral end tidal attachment 3709.

The nasal respiratory apparatus integrate with the oral end tidal Attachment in the same manner as the articulated nasal respiratory apparatus integrates with the bite block 3600 through the interface plate and illustrated FIG. 38. The top (+Z) surface of the oral ET attachment 3709 could have the same design as the nasal respiratory apparatus interface shelf, element 3609 shown in FIG. 36. The bottom (−Z) surface of the nasal respiratory apparatus could have the same nasal respiratory apparatus connection pins as shown for the articulated nasal respiratory apparatus in FIG. 38.

Figure 40:
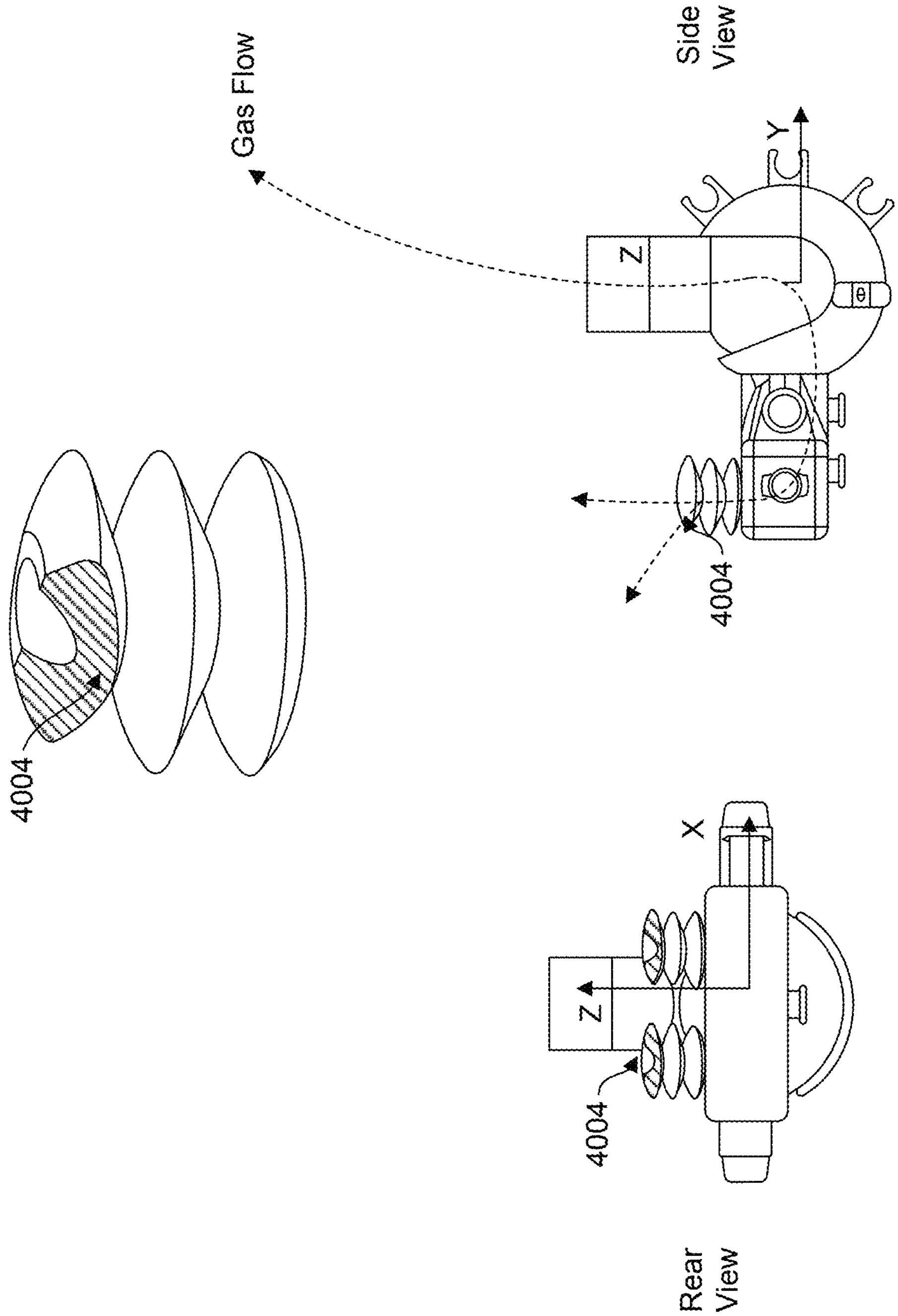
FIG. 40 illustrates truncated nares ports.

An optional nares port configuration for use with any of the embodiments disclosed herein includes a truncated nares port 4004 as shown in FIG. 40. The nares port shown in earlier configurations had a nominal flow direction about a single axis, the Z-axis had been shown. A tilt of the single axis of flow about the X or Y-axis may provide an improved alignment with the nasal cavity or to better secure against the patient's nostrils. The truncated configuration allows for flow in both the axial Z direction, as well as at an angle, in the −Y direction as shown in the figure. This configuration may allow for more optimal alignment with the nasal cavity while maintaining the structural support parallel with the Z-axis.

Figure 41:
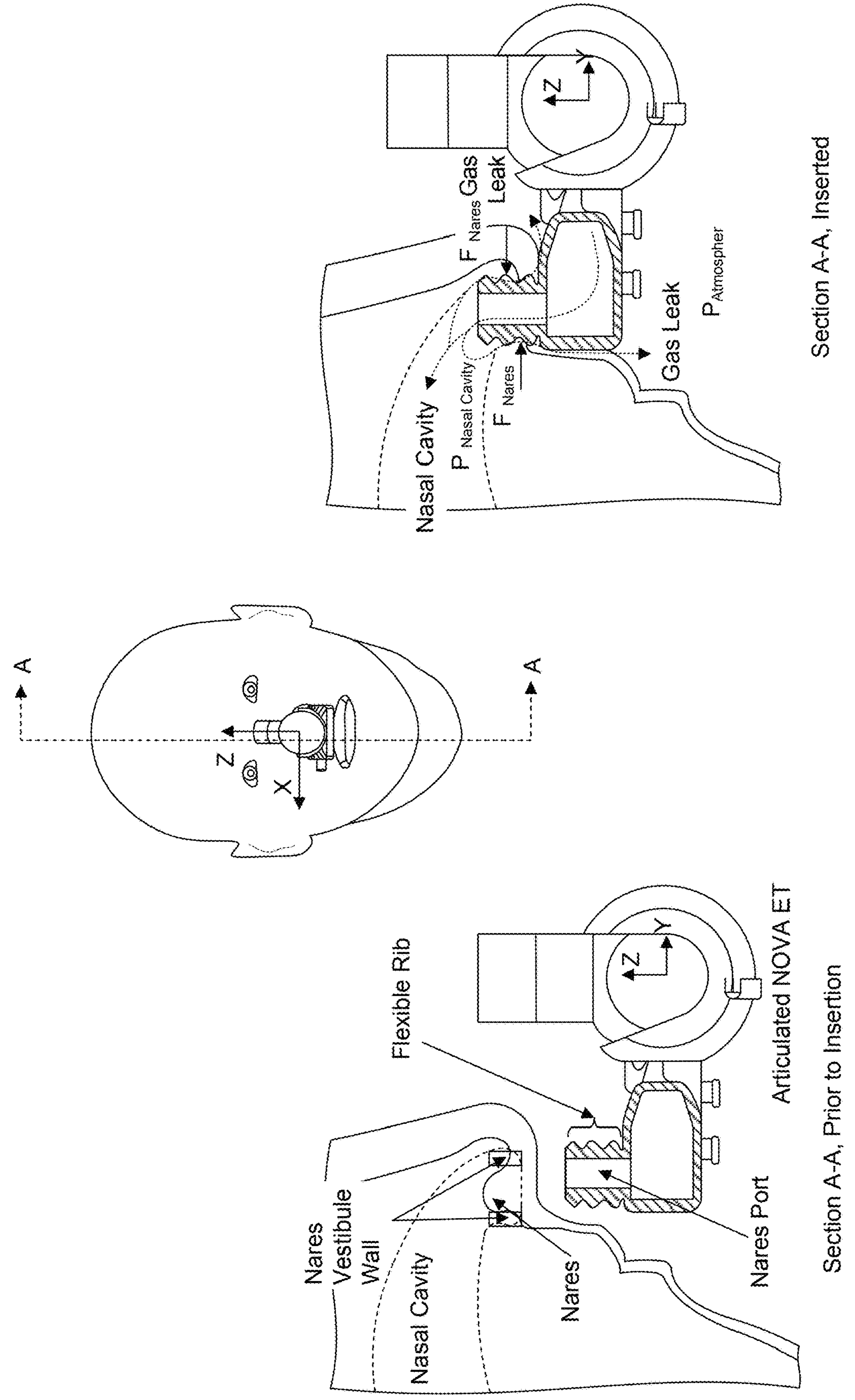
FIG. 41 illustrates a nares port sealing methodology.

A seal between the exterior surface of a nares port and a nasal Vestibule wall may cause stretching of the tissue in the wall (applying a circumferential tensile load about the Z-axis of the tissue wall) when the port is inserted, as shown in FIG. 41. A Cartesian X-Y-Z Coordinate system centered on the articulated nasal respiratory apparatus is referenced throughout all illustrations. This is effectively stretching the wall like a rubber band. The perimeter of the nasal port is greater than the corresponding interior perimeter of the nasal Vestibule Wall and the tissue in the wall has to elastically stretch in order to accommodate the nasal port. This stretching results in a radial force, $F_{Nares}$, pointed toward the Z-axis. Regardless of the outer cover of the nares port be it flexible ribs as shown in FIG. 41, a balloon seal or other geometry, the maximum pressure that can be applied to the nasal cavity by gas flowing form the nasal respiratory apparatus air chamber through the nares ports is approximately 15 CM H2O. This limit is due to the fact that a larger normal force between the nares wall and the nares port may result in patient discomfort, and tissue damage in the extreme, to the wearer due to the tensile force that has to be applied to the tissue in the nasal Vestibule Wall. Some respiratory therapies require nasal cavity pressure levels that could exceed 20-30 CM H2O, so a different sealing solution may be preferable.

Figure 42:
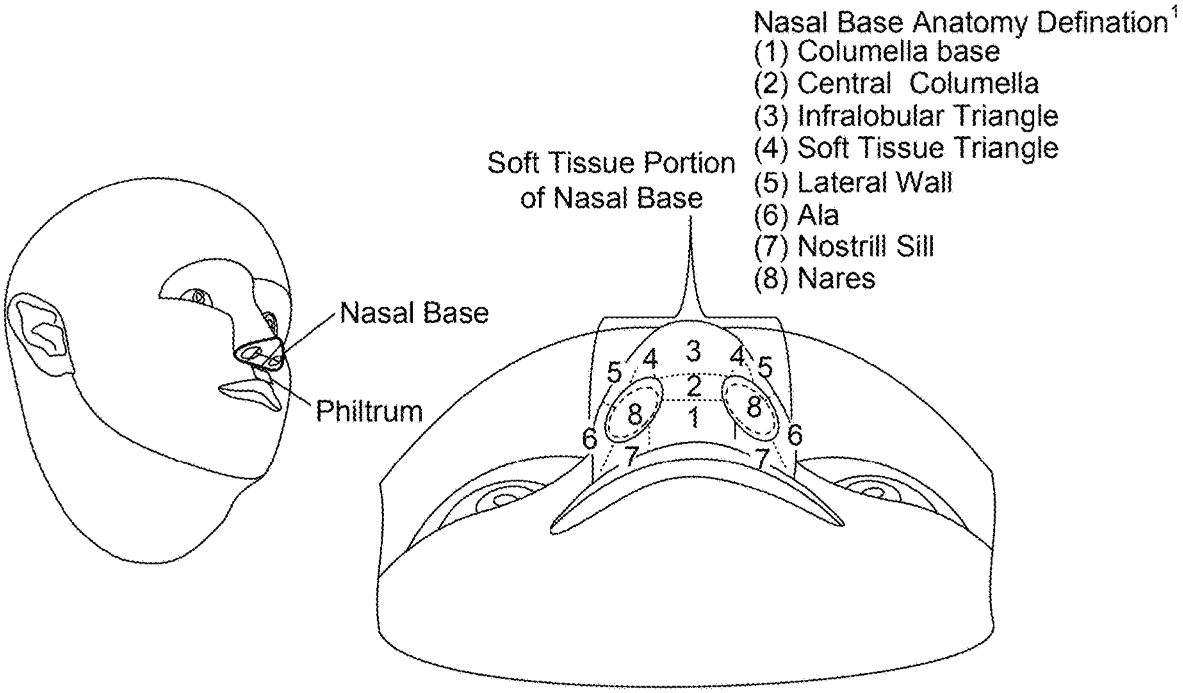
FIG. 42 shows nasal base anatomy.
Figure 43:
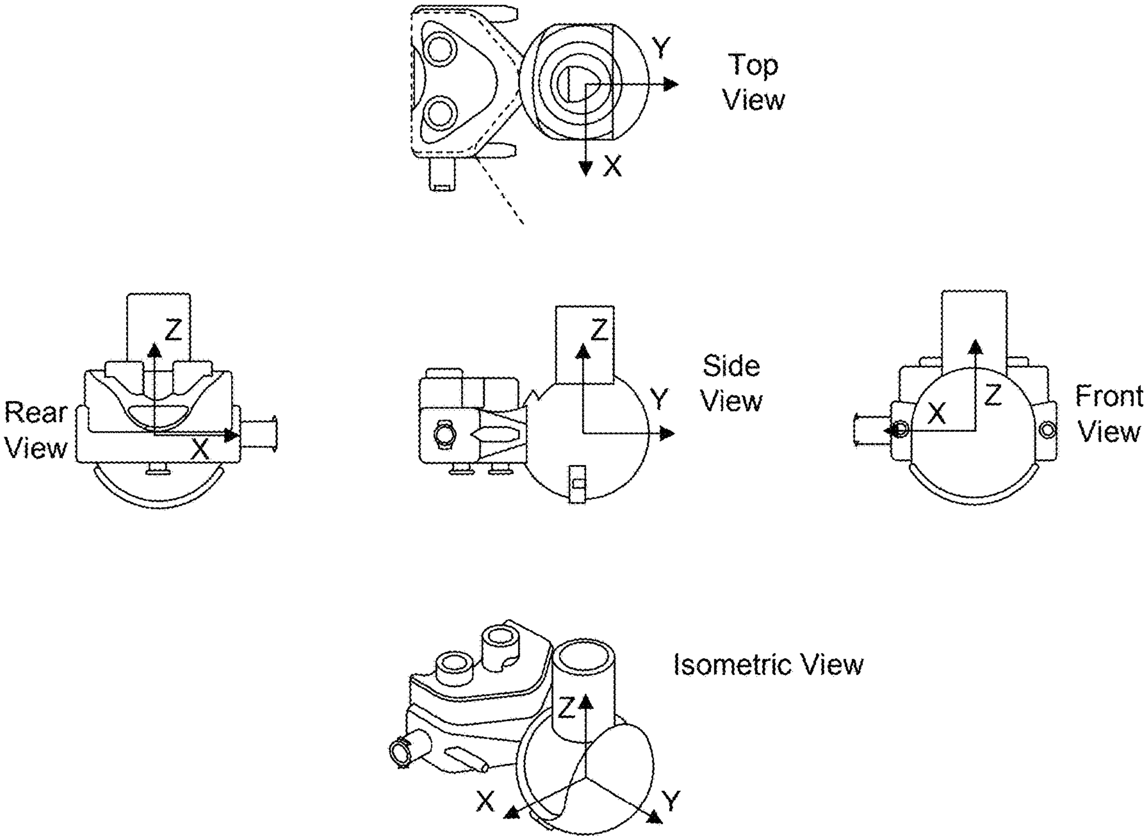
FIG. 43 illustrates nasal dam as part of an articulated nasal respiratory apparatus.

A diagram of a patient's nasal base is illustrated in FIG. 42. An articulated nasal respiratory apparatus with a nasal dam is illustrated in FIG. 43. Although illustrated in combination with an articulated nasal respiratory apparatus, the nasal dam may be used with a non-articulated embodiment described herein. The nasal dam as shown in FIG. 43 seals the perimeter around. The nasal base is nominally planer, including the nares openings into the nasal cavity and fleshy regions that encircle the nares openings called out in FIG. 42. The nasal dam may be made of a soft low durometer material, with a Shore A 10-100 durometer. It surrounds the nares ports and is shaped to have nominally the inverse geometry of the nasal base, in order have a close fit when the nares ports are inserted into the nares opening of the base.

Figure 44:
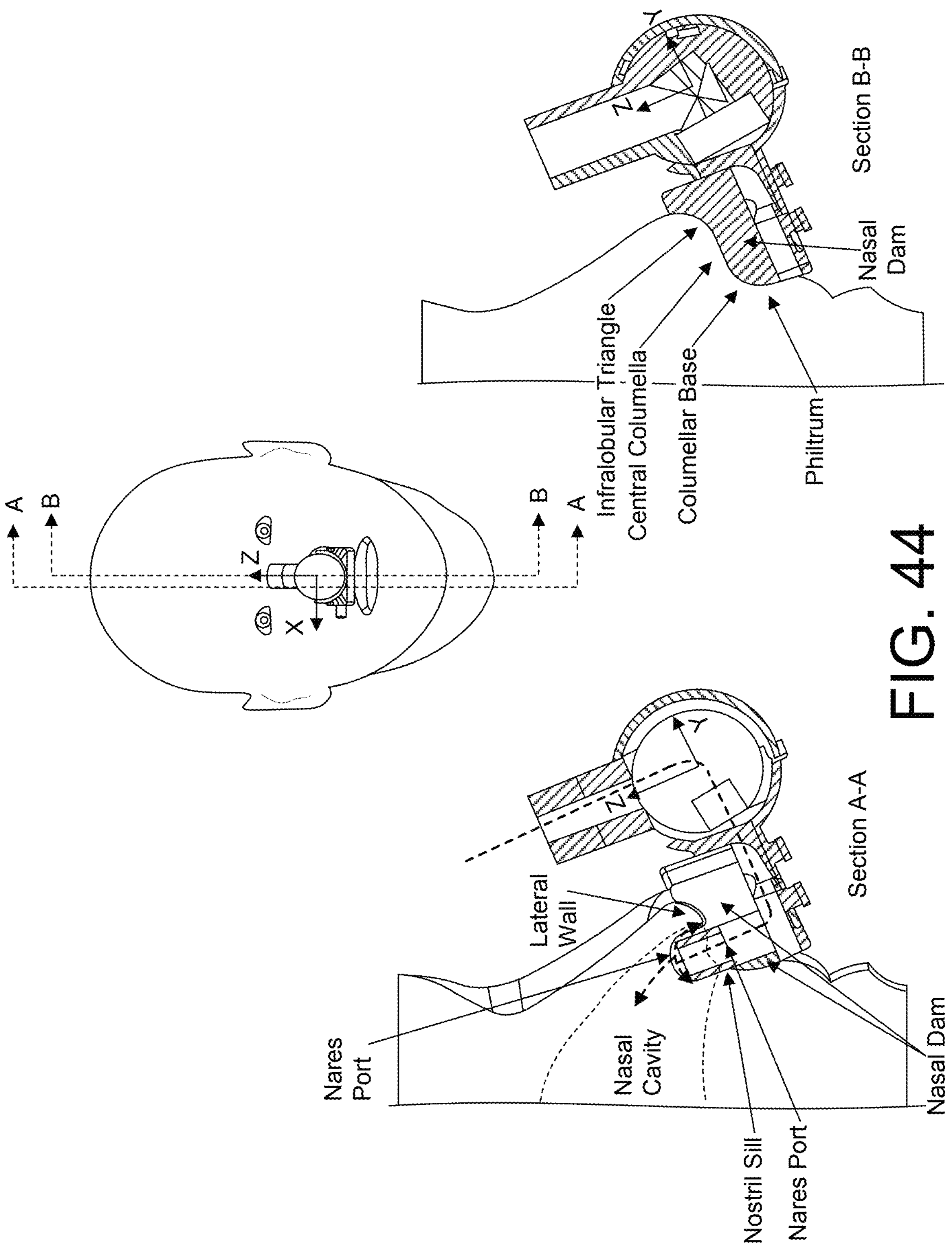
FIG. 44 is a sectional view of articulated nasal respiratory apparatus with nasal dam inserted into the nares.

FIG. 44 shows two cross-sectional views of the nares port inserted into the nares along the Y-Z plane. A force is been applied to the nasal dam in the Z direction, compressing both the compliant tissue in the nasal base and the nasal dam, resulting in a seal about both nares ports. Given the force on the tissue is compressive, a force adequate to withstand pressure in the nasal cavity of greater than 20-30 CM H2O and prevent leaking from the nares can be applied with minimal discomfort, or potential for damaging tissue. Coincident locations of the various nasal base regions and the nasal dam are shown.

Figure 45:
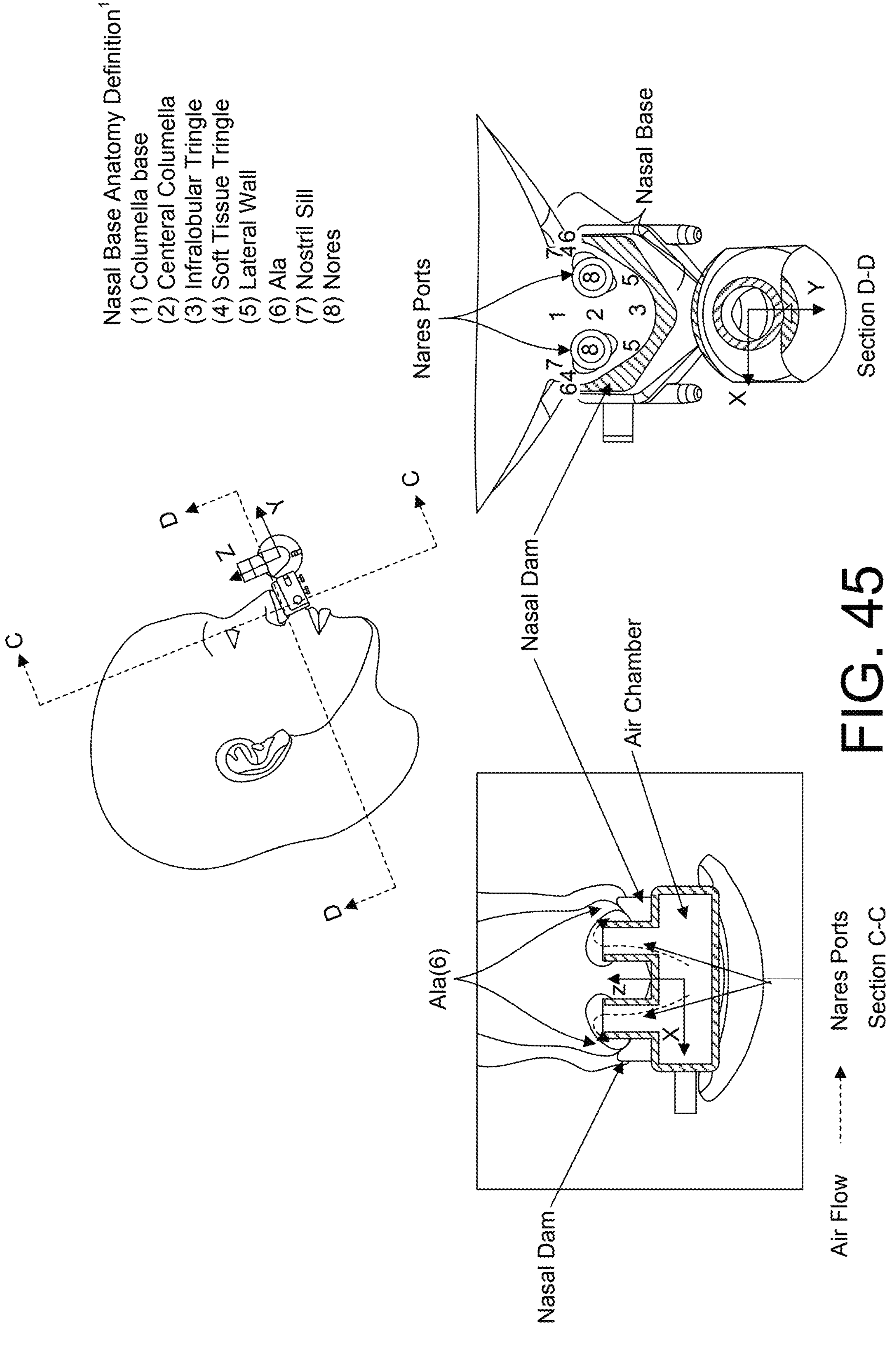
FIG. 45 is a sectional view of articulated nasal respiratory apparatus with nasal dam inserted into the nares.

FIG. 45 provides two additional orthogonal cross-sections showing the nares ports inserted through the nares and against the nasal base, with compressive force applied to the soft tissue of the nasal base in the Z direction. Coincident locations of the various nasal base regions and the nasal dam are called out. The nares are sealed due to the contiguous interface between the Soft Tissue of the nasal base and the nasal dam surrounding the nares ports. Flow from the air chamber through the nasal ports terminate at the nasal base-nasal dam interface as illustrated by the dotted red lie with an arrow.

Figure 46:
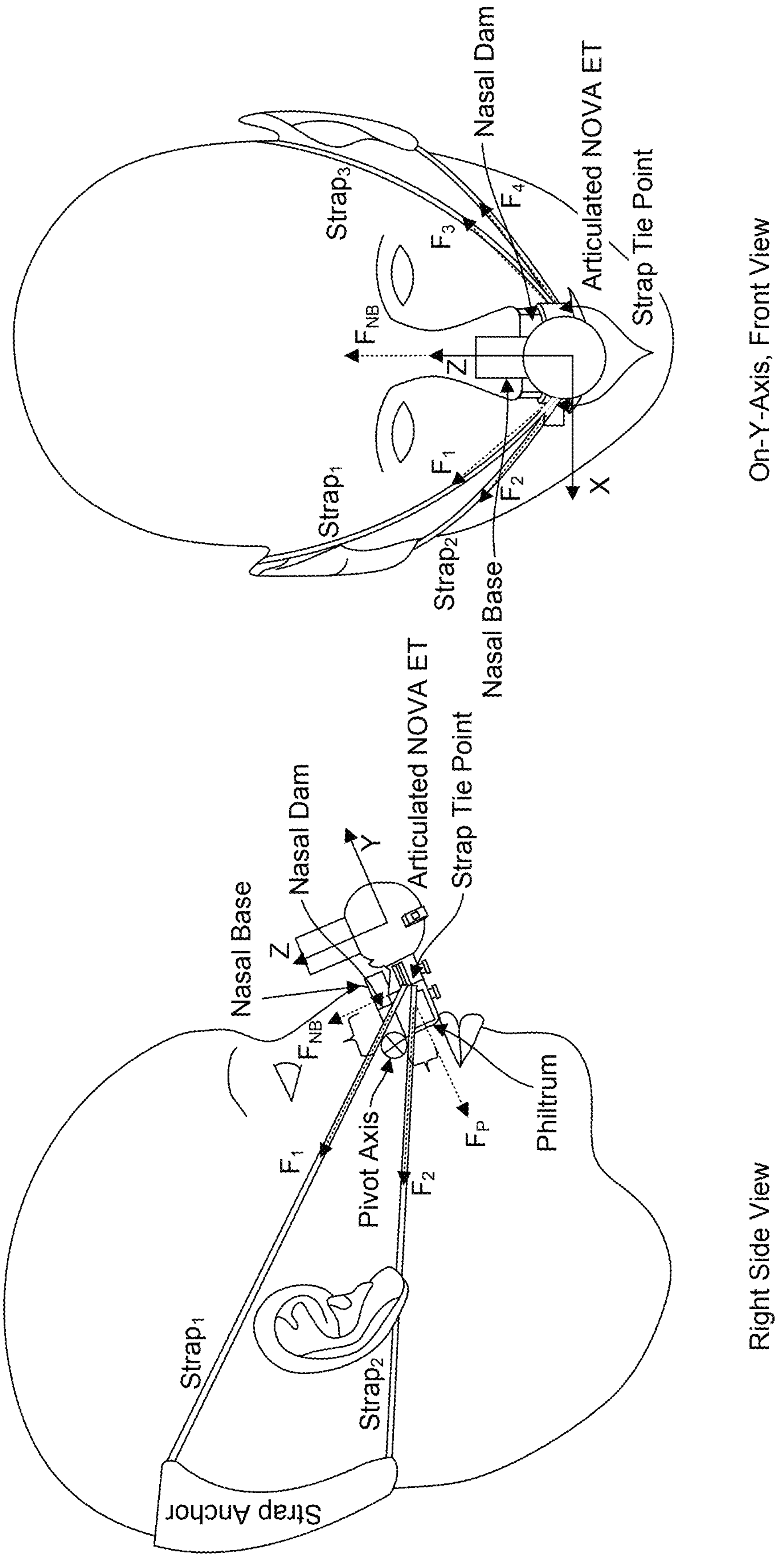
FIG. 46 illustrates a strap configuration providing Compressive Force to the soft tissue of the nasal base.

A compressive force, $F_{NB}$ can be transmitted in the Z direction through the nasal dam to the nasal base using multiple approaches. Force in FIG. 46 is shown as a vector (dashed line terminating in an arrowhead indicating magnitude and direction). One configuration illustrated in FIG. 46 includes one or more elastic straps connected to tie points on either side of the air chamber Assemble of the articulated nasal respiratory apparatus, terminating at a strap anchor located at the back of the head. In this configuration, there are a total of four straps that have been stretched, creating a tensile force, when the ends of the straps are placed over the strap tie points. Straps 1 and 2, providing a tensile force $F_1$ and $F_2$ along the respective strap, attached to the Tie Point on the plus X side of the Y-Z plane and Straps 3 and 4, providing a tensile force $F_3$ and $F_4$ along the respective strap, attached to the Tie Point on the negative X side of the Y-Z plane. The net force from the four straps result in two force vectors in the Y-Z plane. $F_{NB}$, transmitted through the nasal dam, provides a force in the plus Z direction and reacts against an equal and opposite force in the nasal base, compressing the soft tissue and sealing the nares ports. $F_P$, transmitted through the nasal dam, provides a force in the negative Y direction and reacts against an equal and opposite force in the soft tissue of the *Philtrum.*

FIG. 46 shows a pivot axis parallel to the X-axis occurs nominally at the intersection of the plane created by the *Philtrum*, nominally parallel to the X-Z plane, and the nasal base that is nominally parallel to the X-Y plane. The two force vectors $F_P$ reacting against the *Philtrum* a distance $l_P$ from the Pivot Axis and $F_{NB}$ reacting against the nasal base a distance $l_{NB}$ from the Pivot Axis in an equal and opposite manner, must be in Force equilibrium with a net force of zero. The net torques applied to the nasal respiratory apparatus about the pivot axis, the sum of $F_P \times l_P$ plus $F_{NB} \times l_{NB}$ must also be in equilibrium with a net zero torque. This is accomplished by locating the strap tie points so that these two conditions are satisfied.

Figure 47:
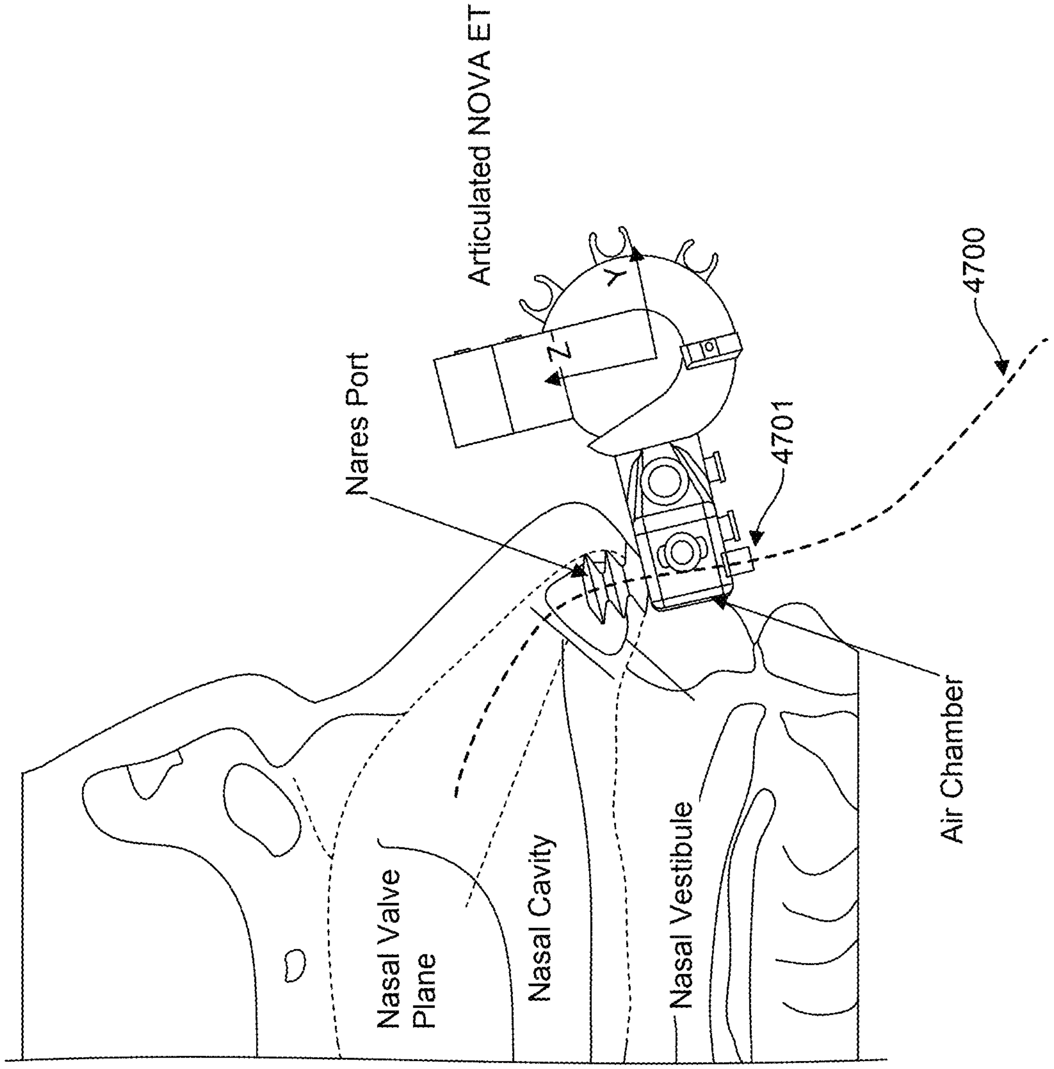
FIG. 47 illustrates an optional catheter port.
Figure 48:
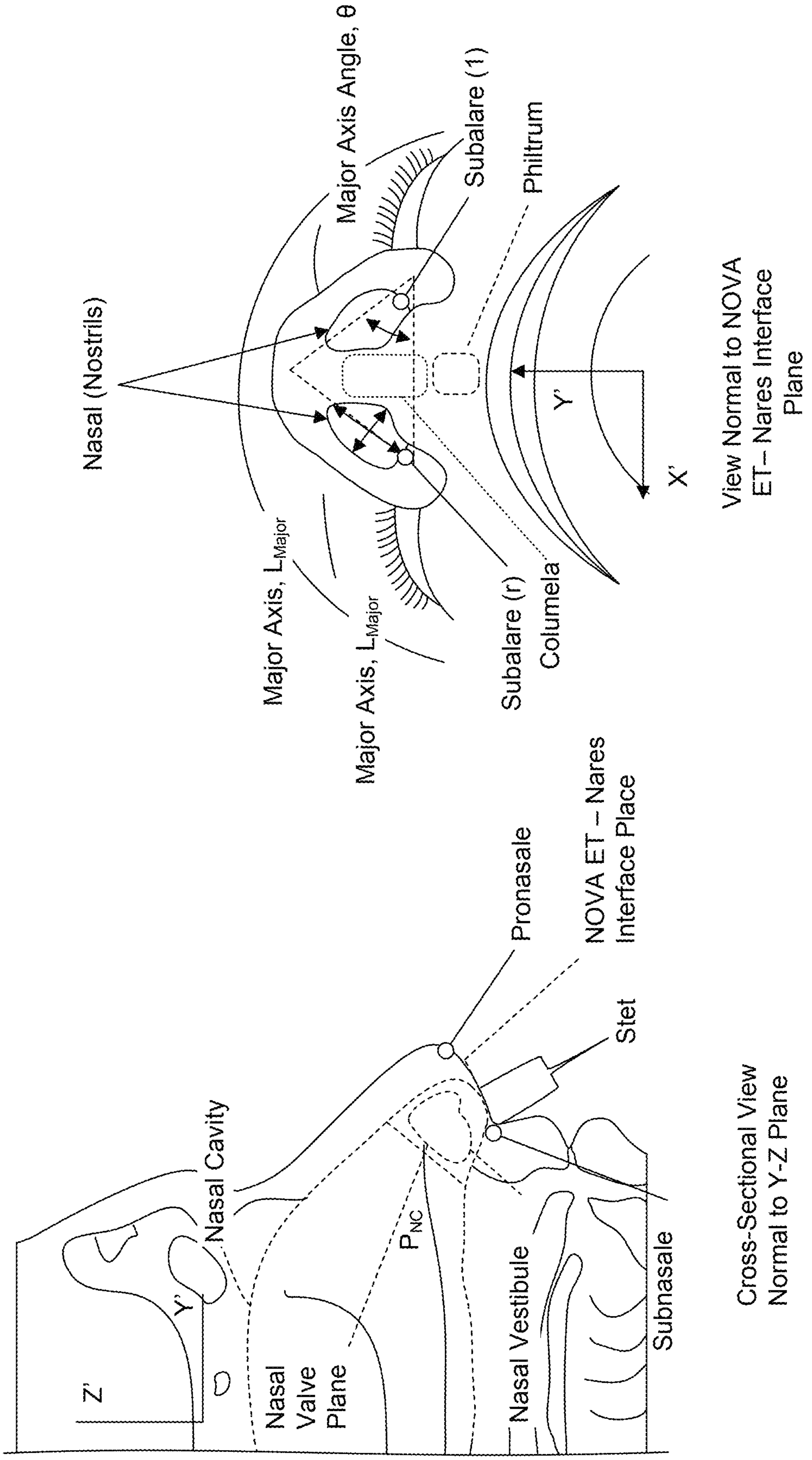
FIG. 48 illustrates nasal anatomy.

An additional feature that could be added to any of the embodiments described herein, including the nasal respiratory apparatus or articulated nasal respiratory apparatus, is a catheter port 4701, as illustrated in FIG. 47. The catheter port 4701 is located below and in line with one of the two nares ports along the Z-axis. The port is capped when not utilized to prevent leakage. When a nasal catheter is required, the port is uncapped and a catheter is inserted into a self-sealing port that encloses the outer circumference of the catheter to prevent leakage from the air chamber. The catheter is fed through the nares port and continues into the nasal cavity. This allows for positive pressure oxygenation and ventilation to be provided to the patient via the second nares port while the catheter is fed through the first nares port.

nasal anatomy relevant to the nasal respiratory apparatus is illustrated in FIG. 48. The cross-sectional view of the nasal structure showing the Y'-Z' plane shows the nares opening in the nasal respiratory apparatus-nares interface plane. The nasal cavity is highlighted by the dotted region. The nasal respiratory apparatus-nares interface plane is a plane nominally parallel and adjacent to the nares openings and the line through the Subnasale-Pronasale points. It is also perpendicular to the Y'-Z' plane. The region inside the nasal cavity is the nasal Vestibule, adjacent to the nares opening. The nasal passage is then constricted by the nasal valve which is adjacent to the nasal Vestibule. The nasal valve creates a plane that is nominally perpendicular to the Y'-Z' plane as shown in FIG. 48.

A view normal to the nasal respiratory apparatus-nares interface plane shows the nares that are nominally elliptical in shape possessing a major axis with a length $L_{Major}$, and a minor axis with a length $L_{Minor}$. The major axis of the nares is rotated towards the tip of the nose at an angle θ. The region between the nares in the nasal respiratory apparatus-nares interface plane is the *Columella* and the region on the lip below the nares is the *Philtrum.*

The nares port could be designed to accommodate a broader demographic by utilizing nares data from a large population, such as that provided in Table 2. The separation distance of the two nares ports would be based on the subnasal width, the distance between the right and left subalare shown in FIG. 48 and the major axes angle θ statistics, provided in Table 1. Statistics of the subnasal width for males and females as a function of age can be found at https://www.facebase.org/facial_norms/summary/index.html#subnasalwidth.

TABLE 1

| Nares Parameter | Mean | Standard Deviation |
|---|---|---|
| Length of major axis, $L_{Major}$ | 1.76 CM | 0.43 CM |
| Length of major axis, $L_{Minor}$ | 0.72 CM | 0.15 CM |
| Major Axis Angle, θ | 53° | 16.6° |

Figure 49:
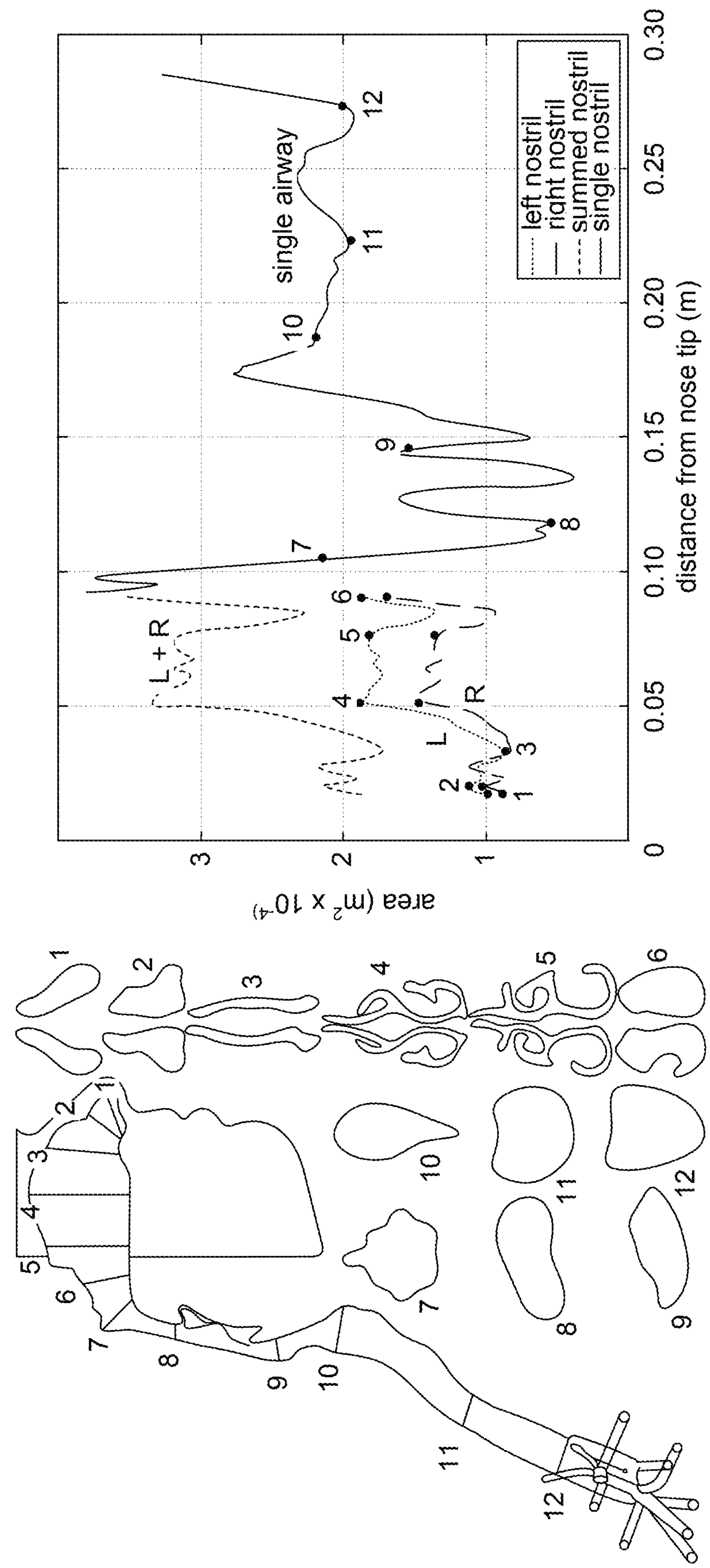
FIG. 49 illustrates geometry of the airway with flow-normal.
Figure 50:
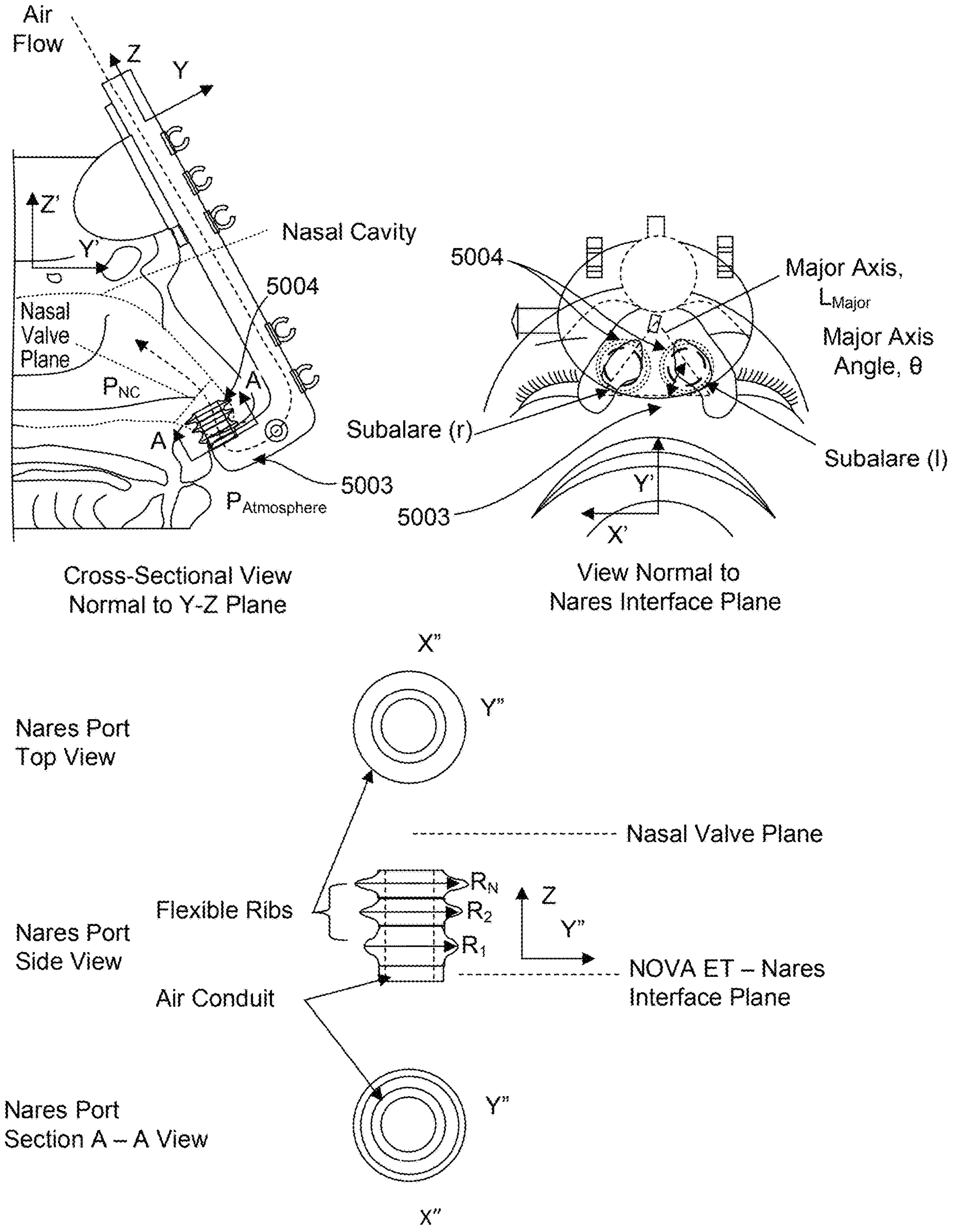
FIG. 50 illustrates nares port with a circular cross-section.
Figure 51:
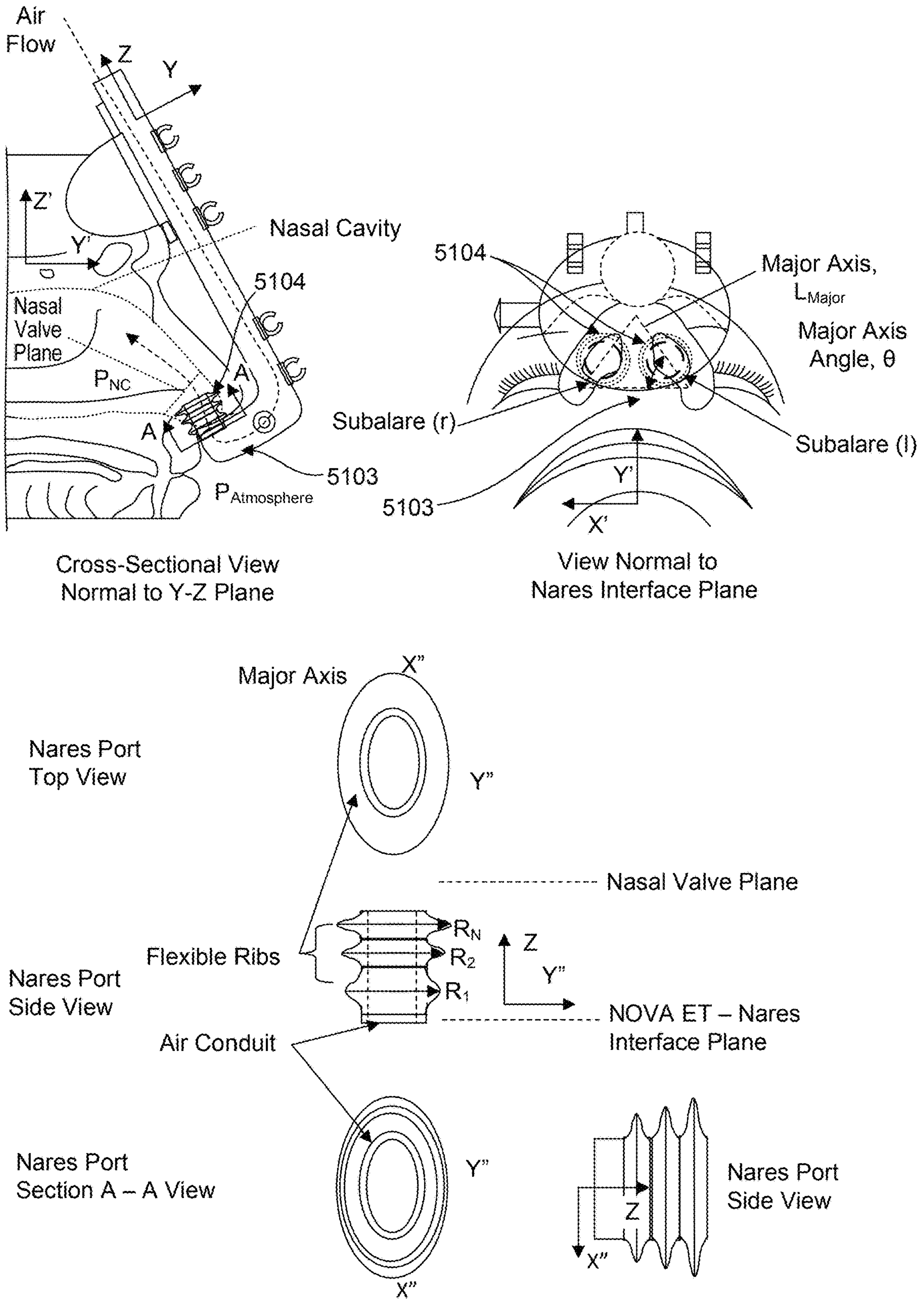
FIG. 51 illustrates nares port with an elliptical cross-section.

Two nares port designs shown in FIG. 50 and FIG. 51 utilize flexible ribs attached to a solid center air conduit. The cross section of the ribs in the X"-Y" plane are intended to be larger than the nasal Vestibule so that when inserted into the vestibule, they compress against the nasal vestibule wall and seal the interface. A feature that would improve the seal of the flexible ribs against the walls of the nasal vestibule would be to increase the area of the flexible ribs in the X"-Y" plane as a function of distance from the nasal respiratory apparatus-nares interface plane. The flow-normal cross-sectional area increases, as shown in FIG. 49 when moving from the nasal respiratory apparatus-nares interface plane (1) and the nasal valve plane (2). Increasing the size of the flexible ribs in order to accommodate the larger cross-sectional area will result in a more secure seal.

The interface between the nasal respiratory apparatus nares port and the nasal cavity is illustrated in FIG. 50. The nares port, mechanically supported by the air chamber, is inserted through the nares into the nasal Vestibule where the sides of the port seal against the vestibule walls. The top of the air chamber interfaces with the *Columella* along the nasal respiratory apparatus-nares interface plane and the front edge of the air chamber rests against the *Philtrum*. The height of the nares port is selected in order that the top of the port avoids touching the nasal valve. The nares port, detailed in Section A-A, includes a rigid air conduit with a circular cross-section that is mechanically connected to the air chamber. It has a hollow center that allows gas to flow between the air chamber and nasal cavity. One or more flexible ribs sized to be larger in diameter than the nasal Vestibule are attached to the outer surface of the air conduit. They deform when inserted through the nares then expand, conforming to the surface of the nasal Vestibule, sealing the nares and allowing for a pressure difference between the nasal cavity at a pressure of PNC, and the atmosphere, $P_{Atmosphere}$, required for Oxygenation and ventilation.

The outer dimensions of the air conduit would be sized so that the diameter was less than the mean length, $L_{Minor}$, minus one or more standard deviations of the minor axis, in order to prevent stretching the nares with a rigid conduit. The flexible rib closest to the nasal respiratory apparatus-nares interface plane would be sized so the diameter equal to the mean major diameter length, $L_{Major}$, plus one or more standard deviations, in order to seal against the nasal vestibule wall.

The position of the nares ports in the X'-Y' plane would be based on the nominal center of the nares where the major and minor axes cross. The intersection of the major axis with the approximate nares ellipse at the nasal base of the left and right nares is separated by a distance equal to the subnasal width, the distance between the right and left subalare shown in FIG. 48. The nares port origin in the X"-Y" plane as shown in the FIG. 50 Section A-A view for the left and right nares ports would be nominally positioned coincident at the crossing for the major and minor nares axes for the left and right nares respectively as illustrated in FIG. 50.

FIG. 51 provides an alternate nares port design based on the nominally elliptical shape of the nares. This configuration provides a tighter seal by more closely conforming to the shape of the nares and nasal Vestibule than a port with a circular cross-section shown in FIG. 50. The nares port, mechanically supported by the air chamber, is inserted through the nares into the nasal Vestibule where the sides of the port seal against the vestibule walls. The top of the air chamber interfaces with the *Columella* along the nasal respiratory apparatus-nares interface plane and the front edge of the air chamber rests against the *Philtrum*. The height of the nares port is selected in order that the top of the port avoids touching the nasal valve. The nares port, detailed in Section A-A of FIG. 51, includes a rigid air conduit with a circular cross-section that is mechanically connected to the air chamber. It has a hollow center that allows gas to flow between the air chamber and nasal cavity. One or more flexible ribs sized to be larger in diameter than the nasal Vestibule are attached to the outer surface of the air conduit. The deform when inserted through the nares then expand, conforming to the walls of the nasal Vestibule, sealing the nares and allowing for a pressure difference between the nasal cavity at a pressure of PNC, and the atmosphere, $P_{Atmosphere}$, required for Oxygenation and ventilation.

The outer dimensions of the air conduit in the X"-Y" plane would be sized so that the lengths of the major and minor axes, $L_{Major}$ and $L_{Minor}$, of the ellipse were less than the mean length minus one or more standard deviations, in order to prevent stretching the nares with a rigid conduit. The flexible rib closest to the nasal respiratory apparatus-nares interface plane would be sized so the ellipse is equal to the mean major and minor axes lengths, $L_{Major}$ and $L_{Minor}$, plus one or more standard deviations, in order to seal against the nasal vestibule wall. Additional flexible ribs extending in the Z direction towards the nasal valve plane can be added, with their cross-sectional areas increasing in order to achieve a better seal by engaging the nasal vestibule wall. This is graphically illustrated by the minor axis near the nasal respiratory apparatus-nares interface plane having a minor axis radius of $R_1$ with subsequent radii of $R_2$-$R_N$ increasing based on the cross-sectional area in the nasal Vestibule.

The intersection of the major axis with the approximate nares ellipse at the nasal base of the left and right nares is separated by a distance equal to the subnasal width, the distance between the right and left subalare shown in FIG. 48. The major axes for both nares ports would be rotated towards each other by the major axis angle θ, as shown in FIG. 51. The nares ports would then be centered over the nares along the left and right major axes as shown in FIG. 51.

Figure 52:
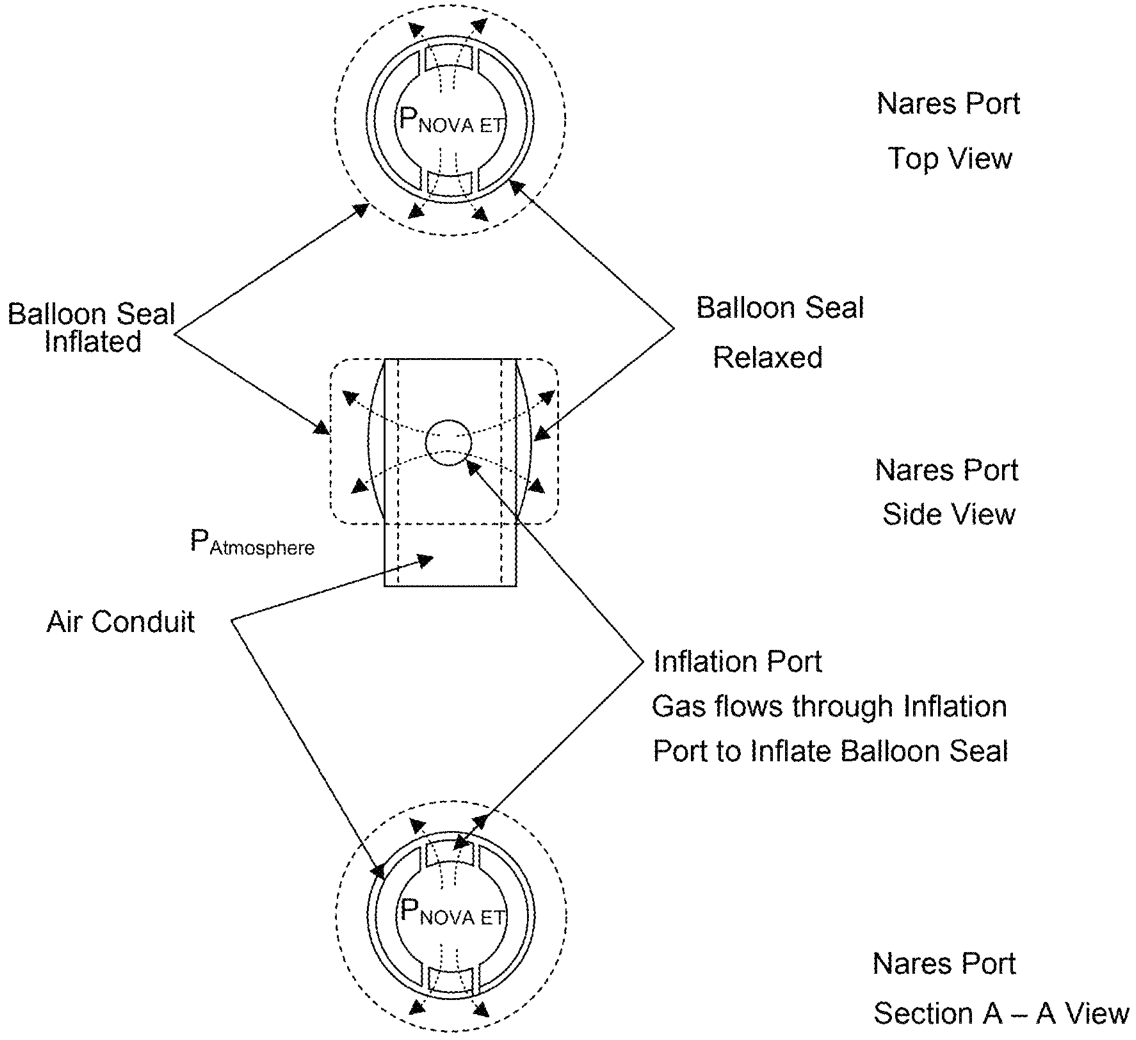
FIG. 52 illustrates a nares port balloon seal configuration.

FIG. 52 shows an alternate nares port seal configuration. In this design, the flexible ribs have been replaced with a balloon membrane that encapsulates the air conduit and is adhered to the top perimeter and an intermediate perimeter of the air conduit. An inflation port also encapsulated by the balloon membrane provides an airpath from the interior of the air conduit to the region between the conduit and the balloon Membrane. After the nares port is inserted into the nasal Vestibule with the balloon seal in a relaxed state, pressure is applied by the gas source for oxygenation resulting in a pressure of $P_{NOVA\ ET}$ that is greater than the pressure of the atmosphere, $P_{Atmosphere}$. This pressure difference forces the balloon seal to inflate, conforming to the walls of the nasal Vestibule and provides an air seal for the nasal cavity.

Figure 53:
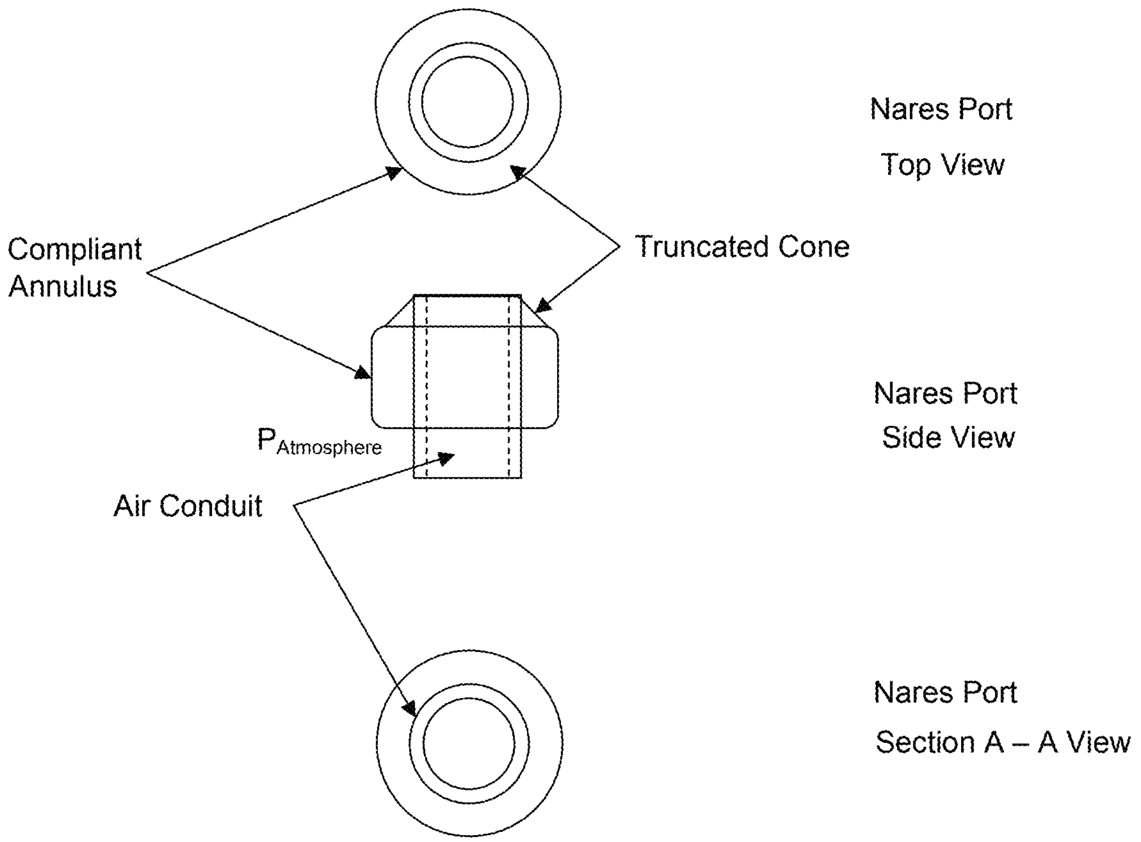
FIG. 53 illustrates a nares port compliant annulus/truncated cone configuration.
Figure 54:
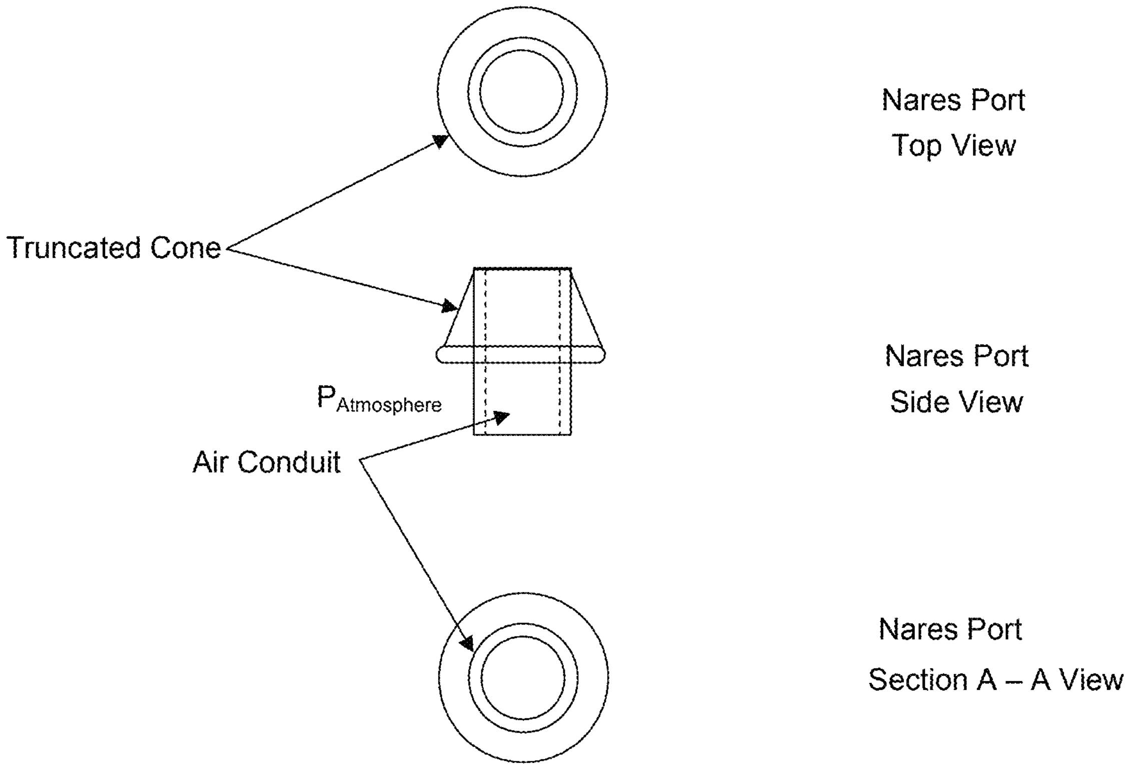
FIG. 54 illustrates a nares port compliant annulus/truncated cone configuration.
Figure 55:
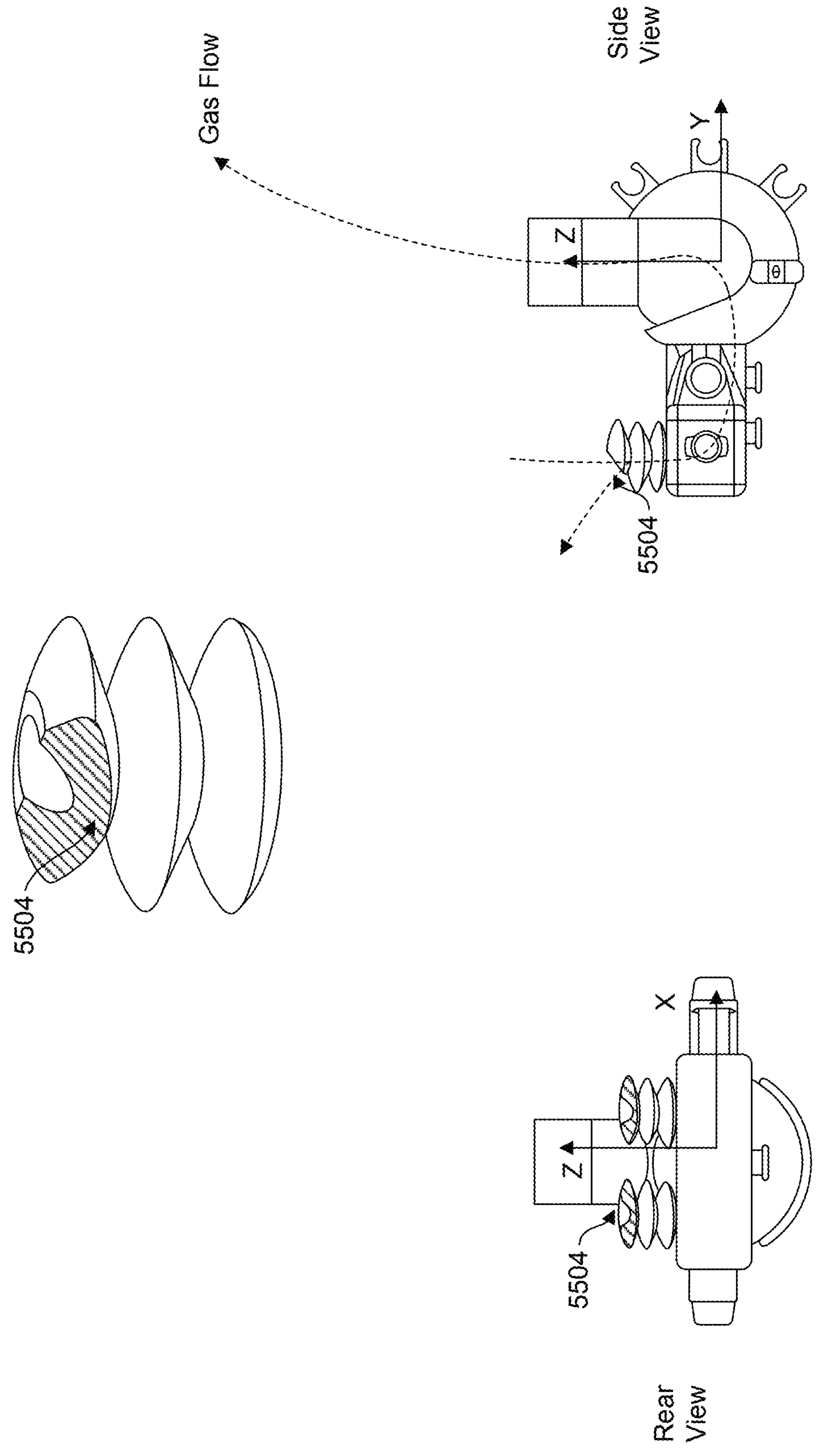
FIG. 55 illustrates truncated nares ports.

Two additional nares port configurations are shown in FIG. 53 and FIG. 54. FIG. 53 shows a nares port with a Compliant Annulus that seals against the nares wall and is attached to an air conduit. A compliant Truncated Cone centers the nares during insertion. FIG. 55 shows a nares port with a Truncated Cone that centers the nares during insertion, seals against the nares wall and is attached to an air conduit.

It may be desirable to have any of the configurations have each nares port rotated about the Y-axis shown, so the openings are tilted towards each other. This configuration would clamp the nasal septum between the nares ports.

Another embodiment for the nares port includes a heat activated seal, where the nasal port expands with increases in temperature such as when placed within the nares.

A further embodiment for the nares port includes a smaller diameter and longer tube, which is movable and expandable and is inserted into the nares port. This tube within the nares port is hollow or solid, extends beyond the soft palate, and is used to provide a mechanical stent between the soft palate and retropharyngeal wall in order to relieve upper airway obstruction. The hollow tube can also be used to suction secretions within the airway.

Figure 56:
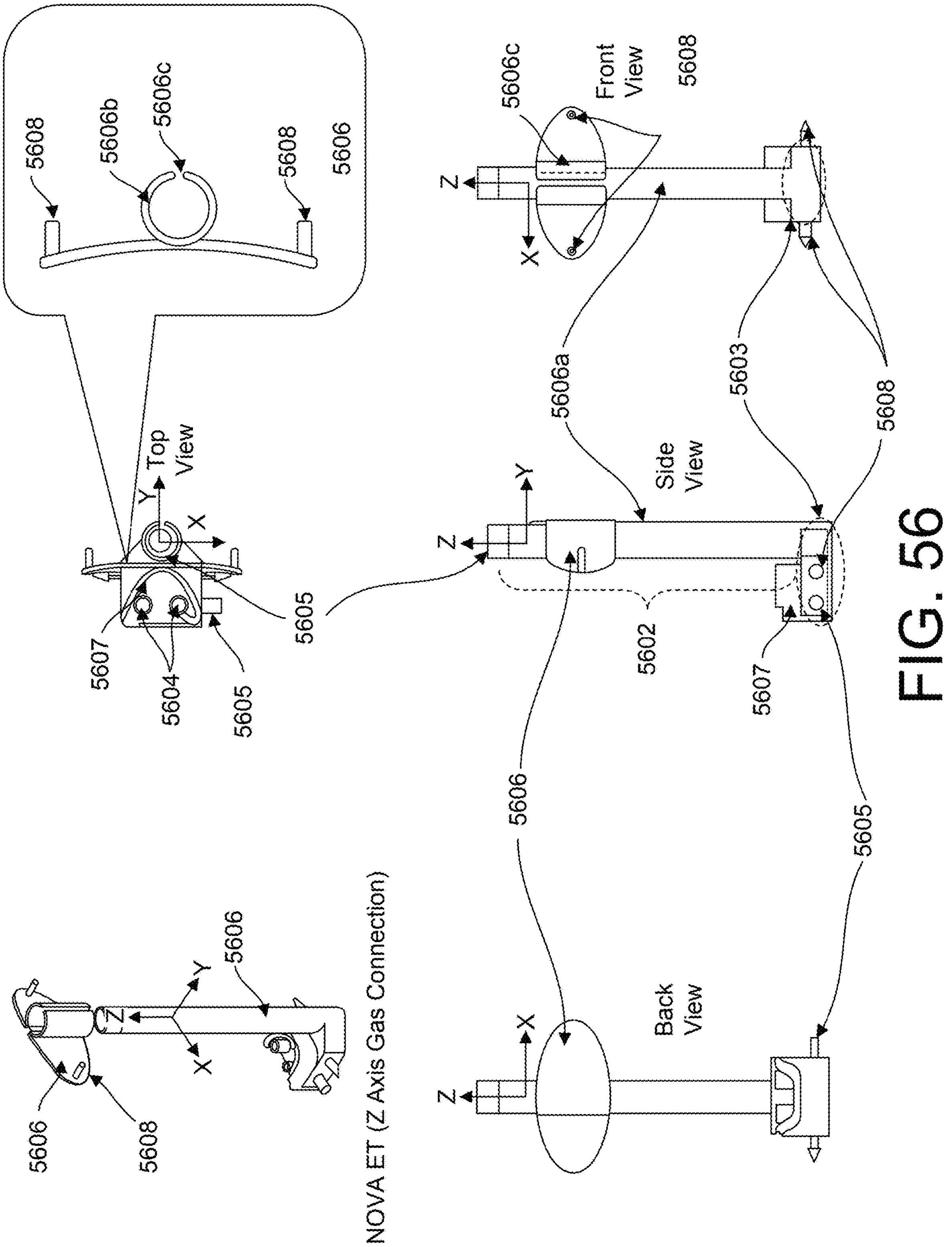
FIG. 56 illustrates a forehead standoff for use with a nasal ventilation appliance.
Figure 57:
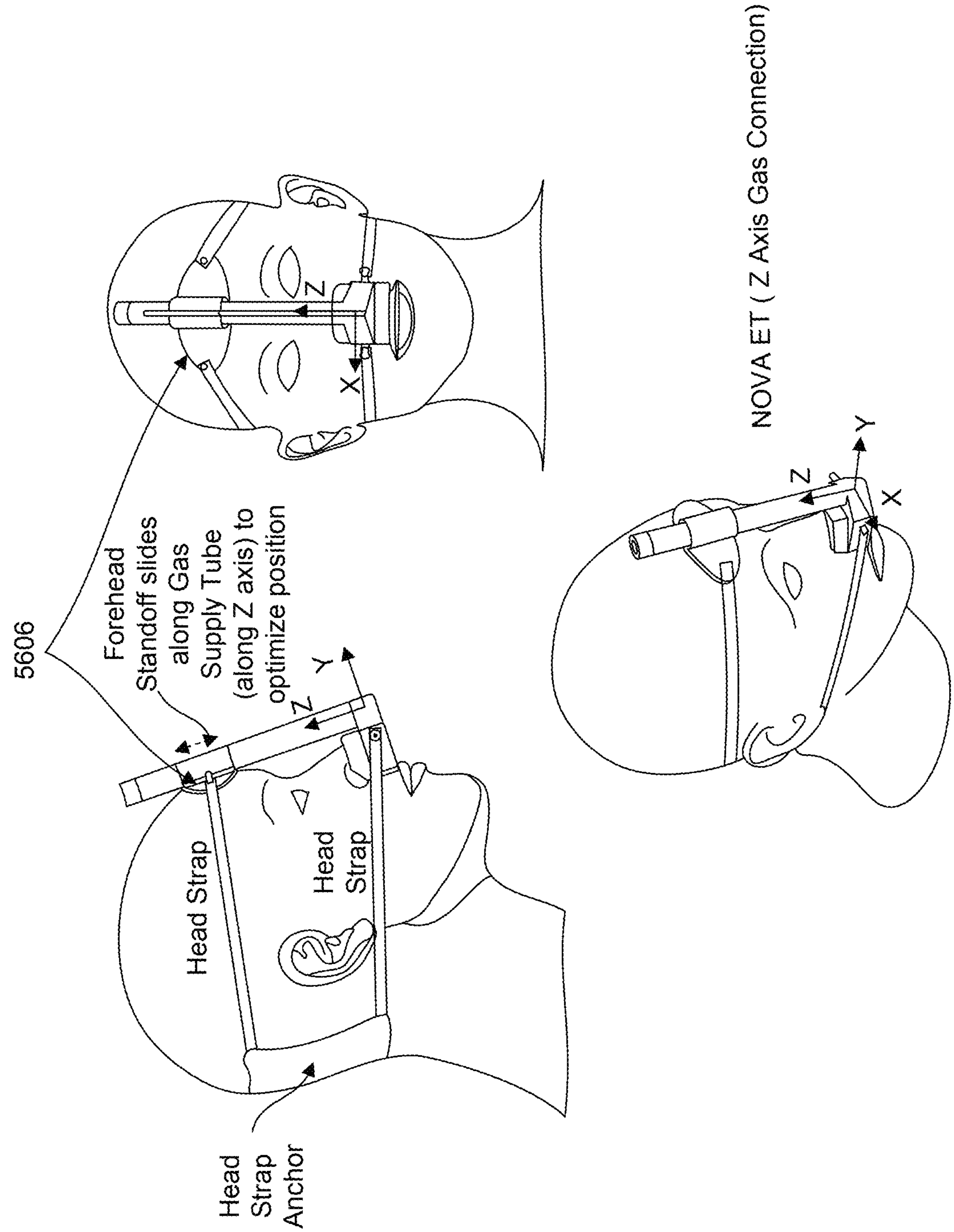
FIG. 57 shows a patient with ventilation appliance with forehead standoff.

In order to minimize pressure form head straps that secure the nasal respiratory apparatus to the patient, a forehead standoff 5606 may be provided, as illustrated in FIG. 56 and FIG. 57. The forehead standoff 5606 attaches to the gas supply tube 5602 by a supply tube clamp 5606*b* that surrounds or substantially surrounds the gas supply tube 5602. The rail slot 5606*c* pinches either side of the rail, having been sized to have a gap that is smaller than the width of the slot. The pinching force is provided by the supply tube clamp 5606*b* that must increase in circumference in order to accommodate the wider rail that runs along the Z-axis of the gas supply tube 5602. This configuration allows for the forehead standoff 5606 to be positioned along the Z-axis of the rail, optimizing placement on the patient's forehead. Its position is maintained by the clamping force of the supply tube clamp 5606*b*. The configuration also reduces rotation of the forehead standoff 5606 about the Z-axis of the gas supply tube 5602, due to the rail 5606*a*, substantially preventing the configuration from rotating.

Figure 58:
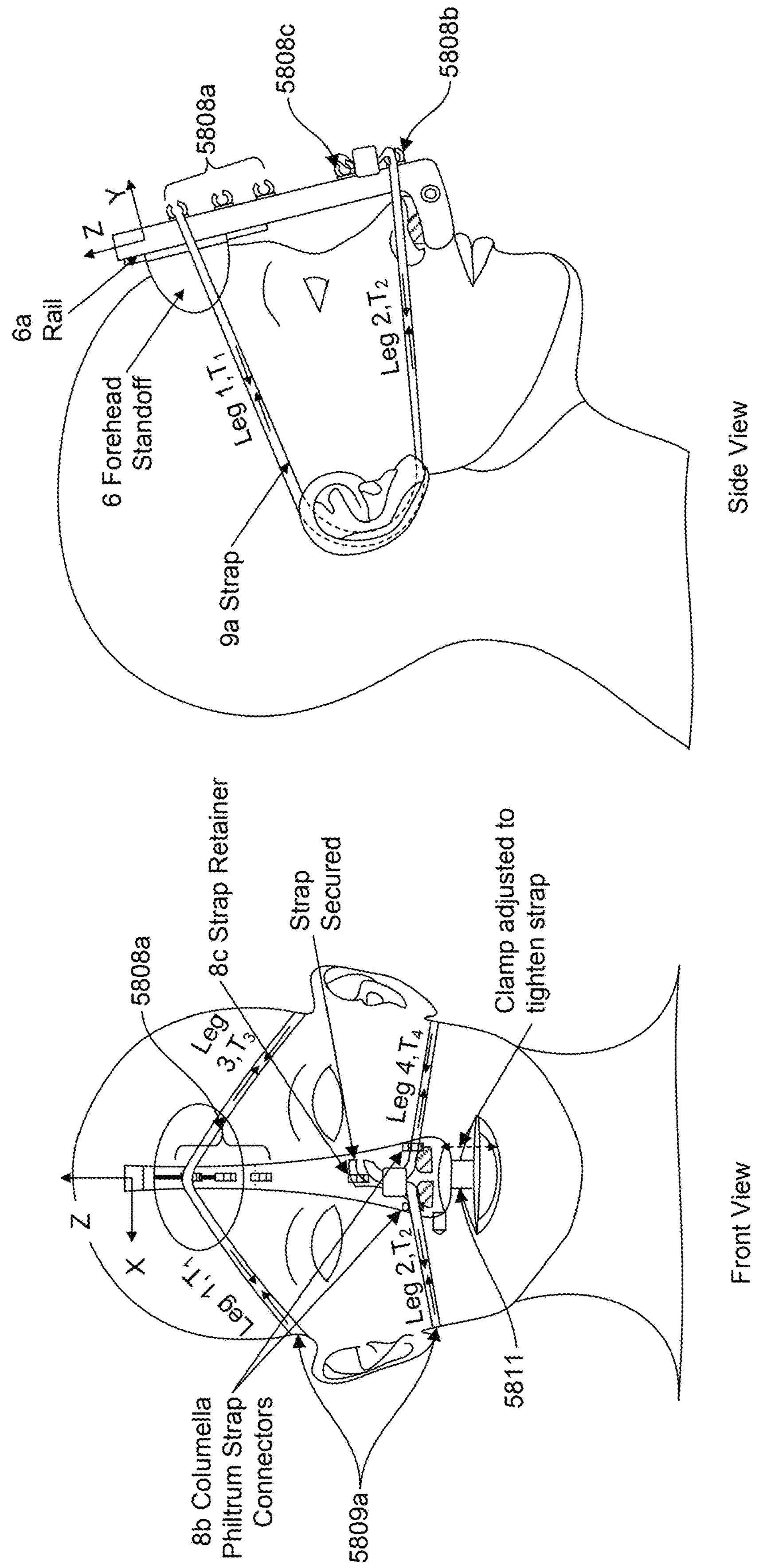
FIG. 58 illustrates a head strap configuration with ear anchor.
Figure 59:
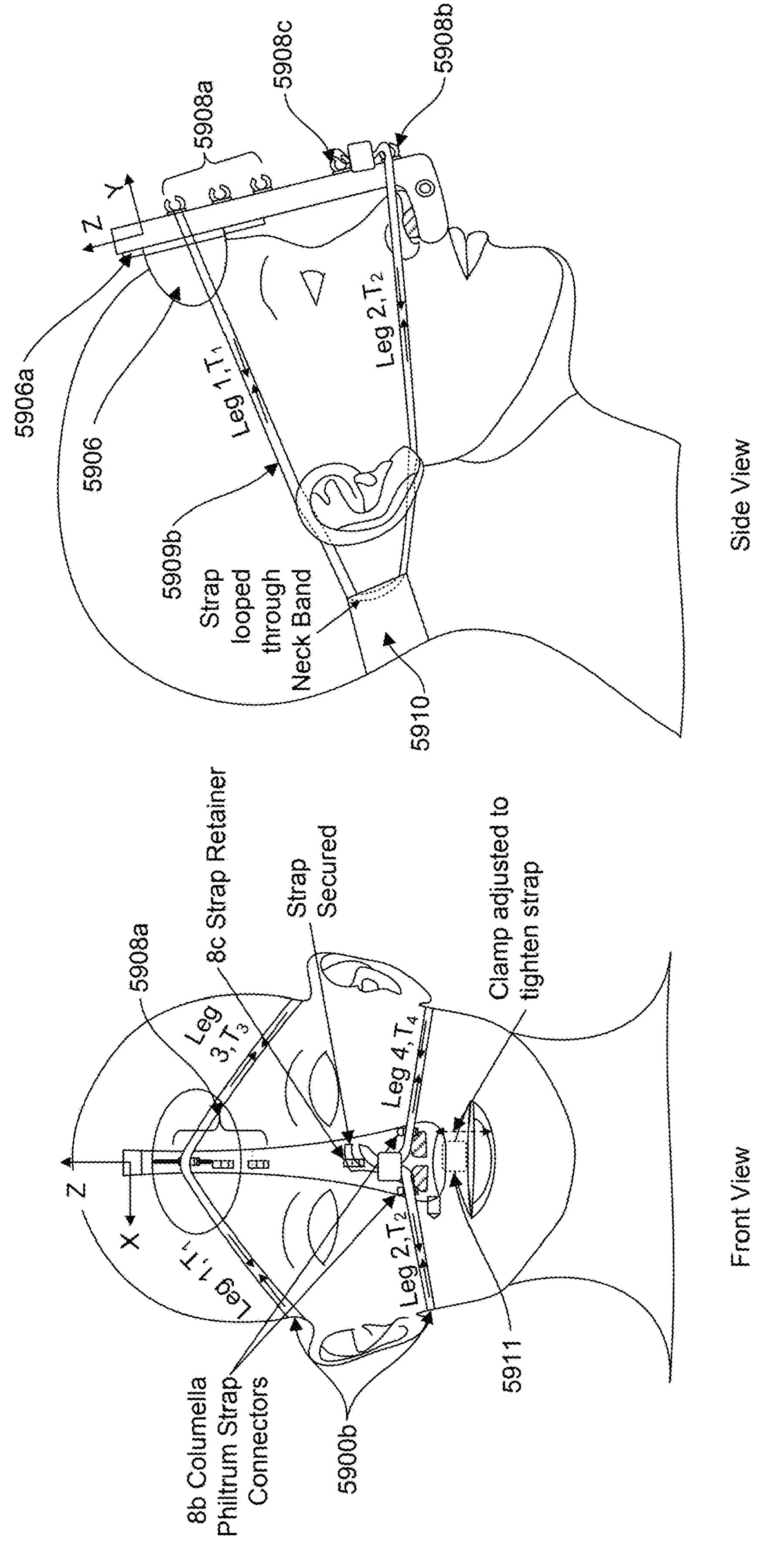
FIG. 59 illustrates a head strap configuration with neck anchor.

The nasal respiratory apparatus can be secured to the patient's head with multiple head strap configurations, two are shown in FIG. 58 and FIG. 59. FIG. 58 shows the ear anchor configuration where after the forehead standoff is centered on the forehead, the strap including one or more elastically compliant cords is looped behind the left and right ear that anchors the nasal respiratory apparatus to the patient's forehead and *Columella-Philtrum* region of the nose. The top of the head strap cord loop is placed in the forehead strap connector, 5808*a*, that is nominally centered over the forehead standoff. The left and right end of the cord terminate between the two *Columella-Philtrum* strap connectors, 5808*b*, and slide through a clamp where the two ends of the cord can be pulled, reducing the cord length between the clamp, in order to increase cord tension or extended to reduce tension. After there is proper tension providing a net force on nasal respiratory apparatus in the negative Y direction, T1-T4, in each of the four Legs of the cord, the free end of the cord is placed in the strap retainer, 5808*b*, in order to keep the strap ends and clamp out of the way of the mouth and eyes.

An alternate head strap configuration is shown in FIG. 59 that provides a different anchor configuration from that shown in FIG. 58. In this configuration, there is a wide band nominally around the back of the patients neck where the head strap cord loops through the neck band on the respective left and right side of the patient. The right side is illustrated in FIG. 59. After the forehead standoff is centered on the forehead, a neck band with the elastically compliant cord looped through the left and right side of the band, is placed behind the back of the neck and anchors the nasal respiratory apparatus to the patient's forehead and *Columella-Philtrum* region of the nose. The top of the head strap cord loop is placed in the forehead strap connector, 5808*a*, that is nominally centered over the forehead standoff. The left and right end of the cord terminate between the two *Columella-Philtrum* strap connectors, 5908*b*, and slide through a clamp where the two ends of the cord can be pulled, reducing the cord length between the clamp, in order to increase cord tension or extended to reduce tension. After there is proper tension providing a net force on nasal respiratory apparatus in the negative Y direction, T1-T4, in each of the four Legs of the cord, the free end of the cord is placed in the strap retainer, 5908*c*, in order to keep the strap ends and clamp out of the way of the mouth and eyes. This configuration substantially eliminates any cord pressure from being applied to the ears and spreads the force due to cord tension over a larger area, resulting in a lower pressure, than in the ear anchor configuration.

Figure 60:
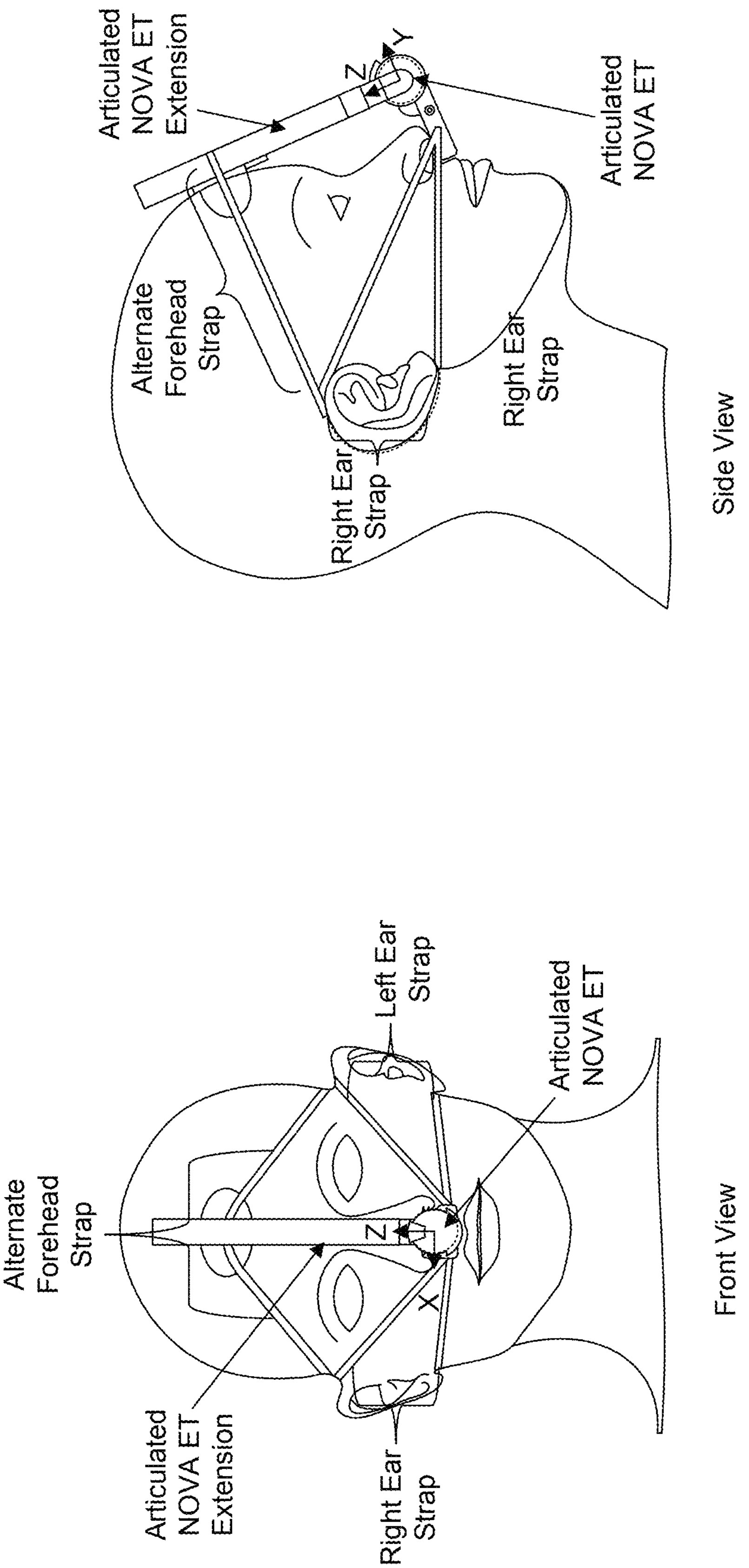
FIG. 60 illustrates an alternate forehead strap configuration with ear strap.

The articulated nasal respiratory apparatus with the Extension can be secured to the patient's head with multiple head strap configurations that under tension when utilized. FIG. 60 shows a right and left ear strap that loop around the respective right and left ears, connecting to the air chamber assembly. Alternatively, the bottom leg of the ear strap, coupled with a forehead strap, as opposed to a top leg, could also be utilized.

Figure 61:
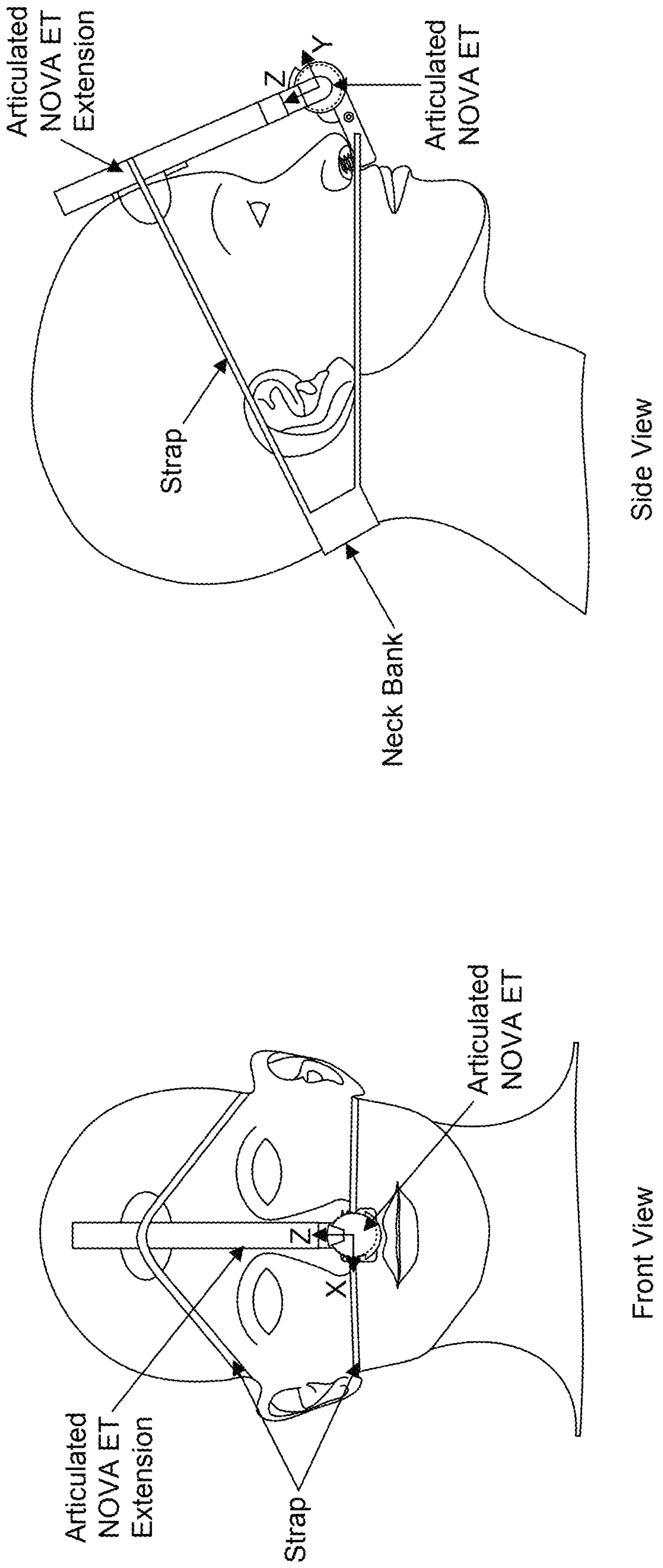
FIG. 61 illustrates an alternate forehead strap configuration with neck band.

An alternate strap configuration for the articulated nasal respiratory apparatus with the Extension is shown in FIG. 61. In this configuration, there is a wide band nominally around the back of the patients neck where the head strap cord loops through the neck band on the respective left and right side of the patient. The right side is illustrated in FIG. 61. After the forehead standoff is centered on the forehead, the neck band with the elastically compliant cord looped through the left and right side of the band, is placed behind the back of the neck and anchors the articulated nasal respiratory apparatus and Extension to the patient's forehead and *Columella-Philtrum* region of the nose. The top of the head strap cord loop is placed in the forehead strap connector, 8*a*, that is nominally centered over the forehead standoff. This configuration virtually eliminates any cord pressure from being applied to the ears and spreads the force due to cord tension over a larger area, resulting in a lower pressure, than in the ear anchor configuration.

All strap configurations could connect to the articulated nasal respiratory apparatus and articulated nasal respiratory apparatus Extension with head strap connectors and or clamp as described earlier in 2.2, or with other connector configurations.

Figure 62:
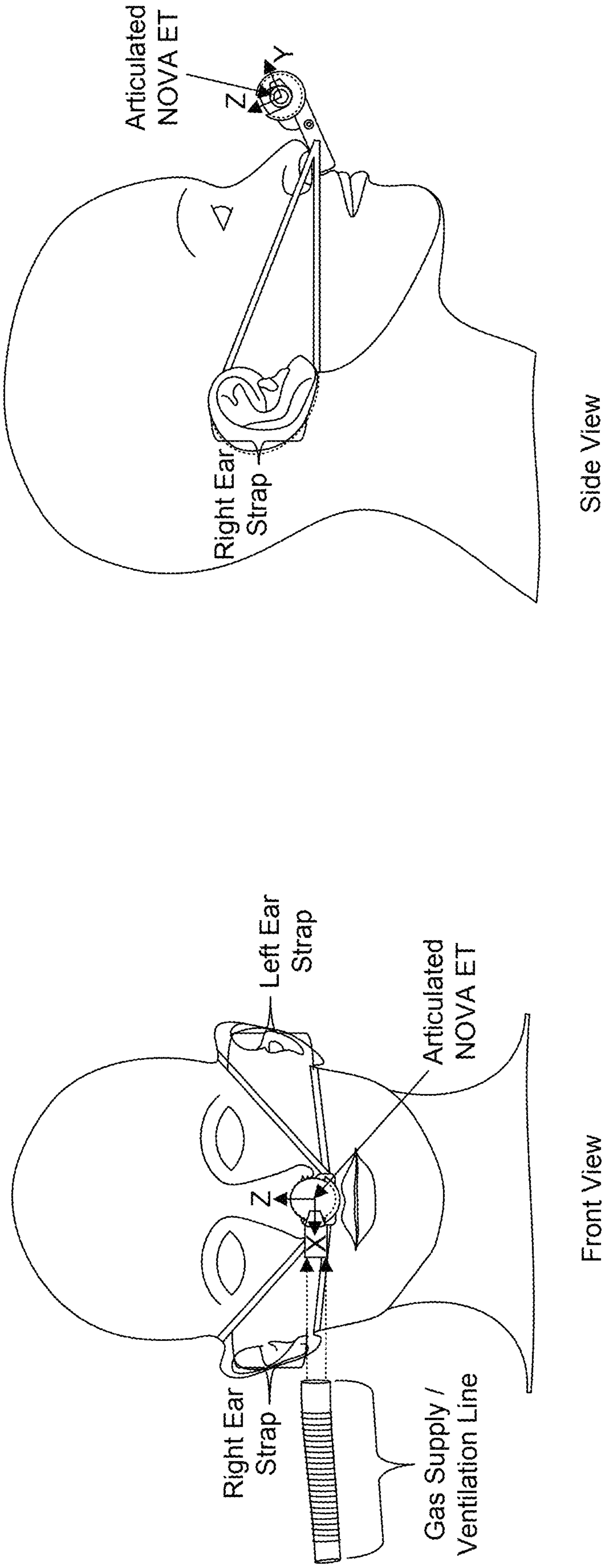
FIG. 62 illustrates an ear strap configuration.

The articulated nasal respiratory apparatus can be secured to the patient's head with multiple head strap configurations that under tension when utilized. FIG. 62 shows a right and left ear strap that loop around the respective right and left ears, connecting to the air chamber assembly. Note the gas port connection assembly is rotated 90° about the Y-axis in this illustration, interfacing with a gas supply/ventilation line. A negative 90° about the Y-axis is also possible.

Figure 63:
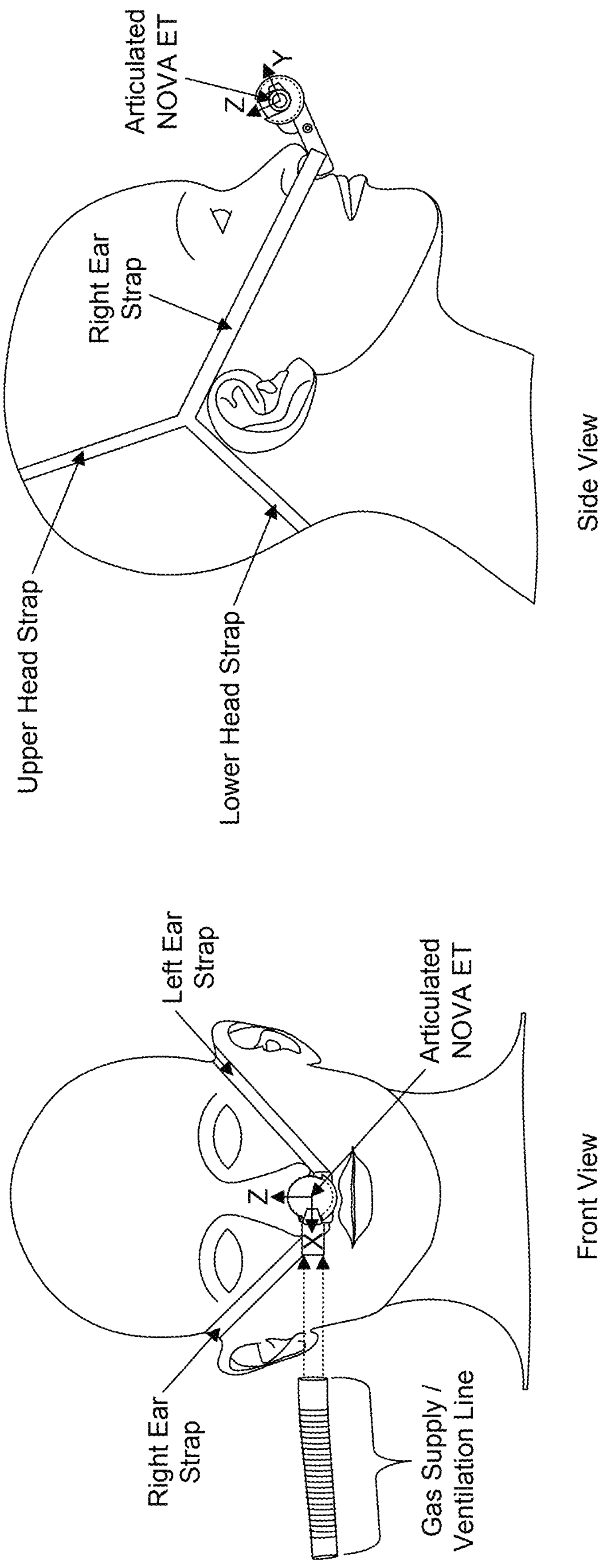
FIG. 63 illustrates a head strap configuration.
Figure 64:
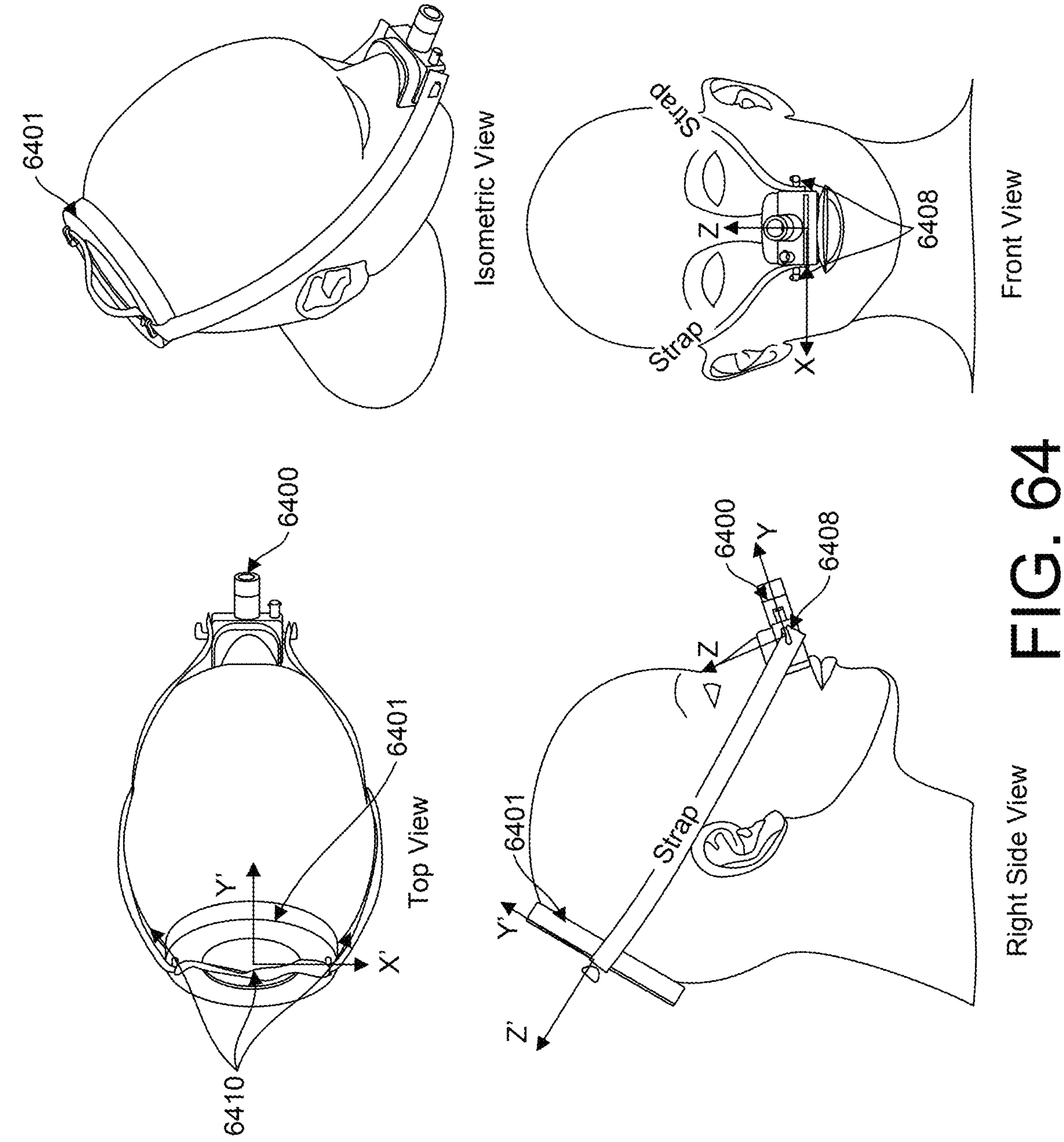
FIG. 64 illustrates a halo head strap.

An alternate head strap configuration for the articulated nasal respiratory apparatus is shown in FIG. 63. In this configuration, there is a, upper and lower head strap connecting to the right and left ear strap. The right and left ear straps connect to the air chamber assembly of the articulated nasal respiratory apparatus. The right side is illustrated in FIG. 63. Note the gas port connection assembly is rotated 90° about the Y-axis in this illustration, interfacing with a gas supply/ventilation line. A negative 90° about the Y-axis is also possible.

All strap configurations could connect to the articulated nasal respiratory apparatus and articulated nasal respiratory apparatus Extension with head strap connectors and or clamp as described earlier, or with other connector configurations.

The coordinate system used in this patent is the right-handed X', Y', Z' axis Cartesian Coordinate system provided in the accompanying figures. The Halo head strap incudes the Halo and the strap shown in FIG. 6, which is described in further detail with respect to FIG. 64 and FIG. 65. The Halo head strap includes the Halo assembly shown in FIG. 64 and the strap shown in FIG. 65.

The is nominally stiff reaction plate 6501 has both the left and right head strap connectors and head strap guides attached. At the opposite side to these elements is attached the Foam Compression Spring. The Reaction Plate spring stiffness in the Z direction, $K_{RP}$, is nominally >10× the spring stiffness of the Foam Compression Spring, K. Spring stiffness is defined as the ratio of applied Force in the Z direction required to achieve a resulting displacement in the Z direction.

The left and right head strap connector 6502, attached to the top of the Reaction Plate, secure the left and right portions of the head strap when attached to the patient.

The left and right head strap guides 6503 retain the associated left and right portion of the strap. The strap is threaded through the corresponding opening of each guide.

The Foam Compression Spring 6504 has a compressive stiffness, $K_F$, units are force per displacement, that results in a tensile load on the strap proportional to the level of compression, ΔZ, in the foam spring. This compression results in the reactive forces F1 and F2 illustrated in FIG. 67. The Foam Compression Spring has a spring rate, $K_F$, that is lower than any other element impacting spring stiffness in the Z direction that influences the force reaction with the nasal respiratory apparatus head strap connector (Tie Point) to the strap by a factor of 10. Spring stiffness is defined as the ratio of applied Force in the Z direction required to achieve a resulting displacement in the Z direction.

Figure 65:
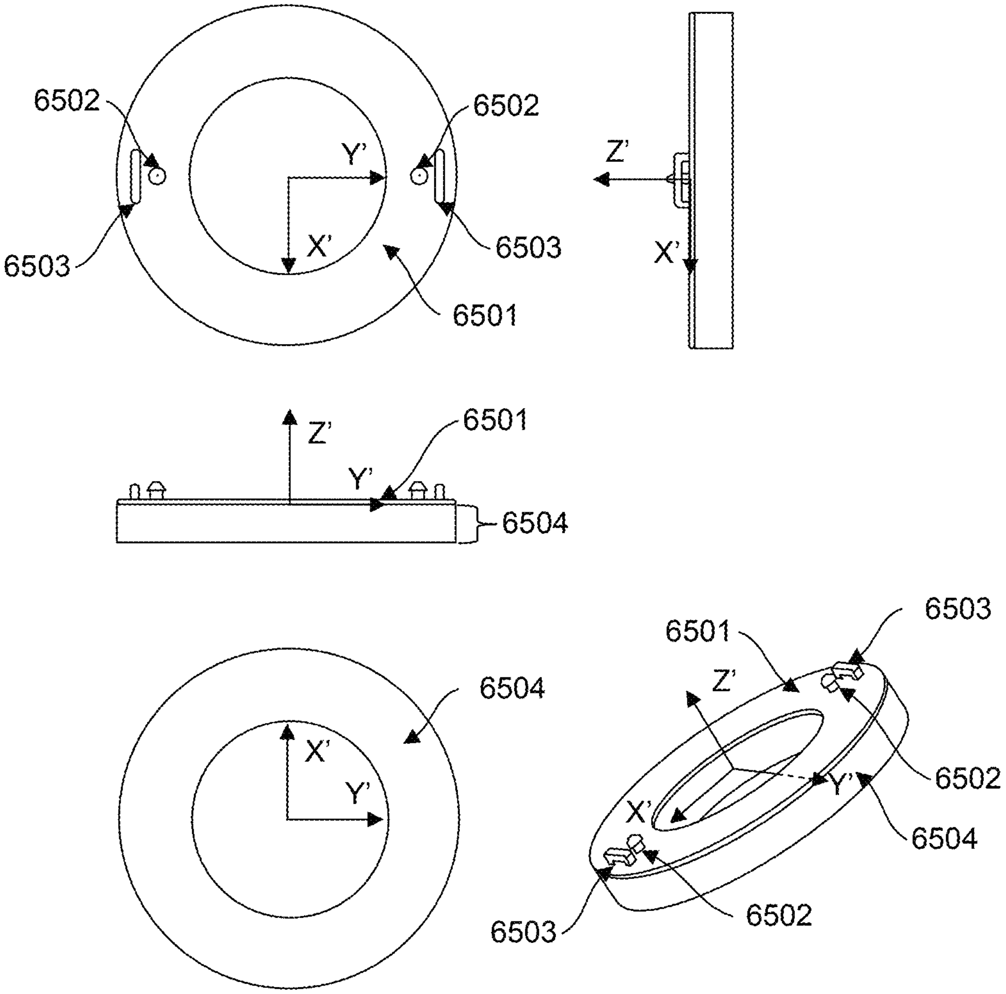
FIG. 65 illustrates a halo assembly.

The strap 6505 shown in FIG. 65 comprises a thin rectangular sheet with multiple holes through the top surface as shown. The holes on the left and right end of the strap interface with the nasal respiratory apparatus strap connectors and the holes in the central portion of the strap interface with the strap connectors on the Halo assembly. The spring stiffness of the strap, $K_S$, is >10× that of the Foam Compression Spring stiffness, $K_F$. Spring stiffness is defined as the ratio of applied Force in the Z direction required to achieve a resulting displacement in the Z direction.

While illustrated in a particular embodiment shown above, the strap is not so limited.

Figure 66:
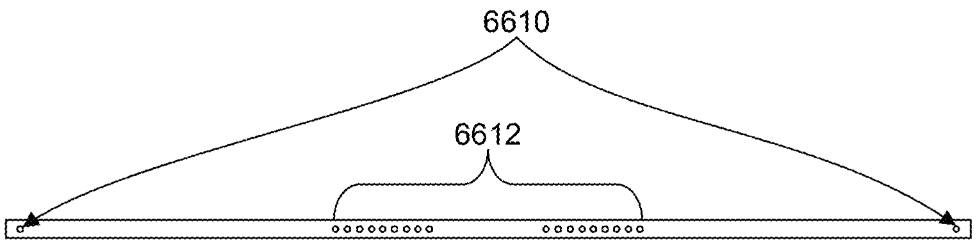
FIG. 66 illustrates a strap for use with the disclosed appliances.

The Halo head strap positioned on the patient as illustrated FIG. 67. View A-A shows the Halo assembly and the nasal respiratory apparatus being placed on the patient's head. The strap is then pulled in the Z direction relative to the Halo assembly tightening the strap and compressing the Foam Compression Spring. This compressing results in the force vectors on the Halo and nasal respiratory apparatus as illustrated, with the system secured to the patient. A strap holes for nasal respiratory apparatus et head strap connector 6610 and strap hole for halo head strap connector 6612 are shown in FIG. 66.

Figure 68:
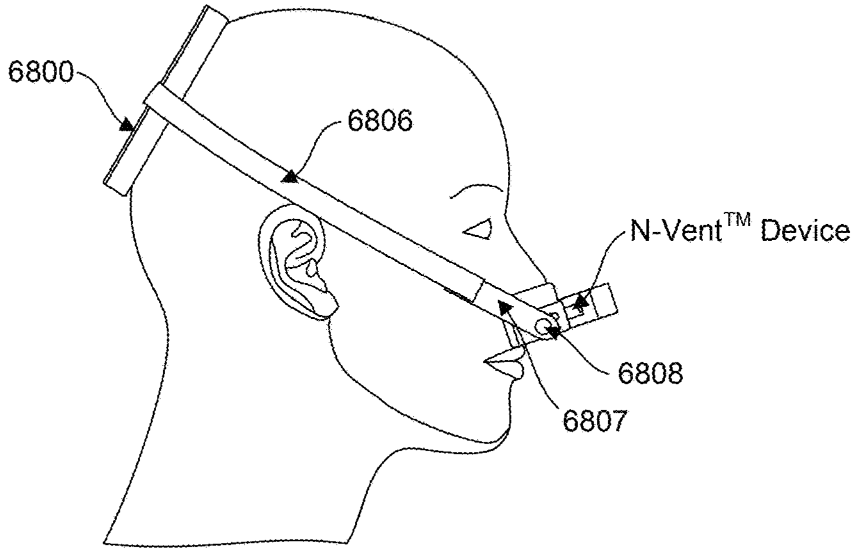
FIG. 68 illustrates a halo head strap assembly.
Figure 69:
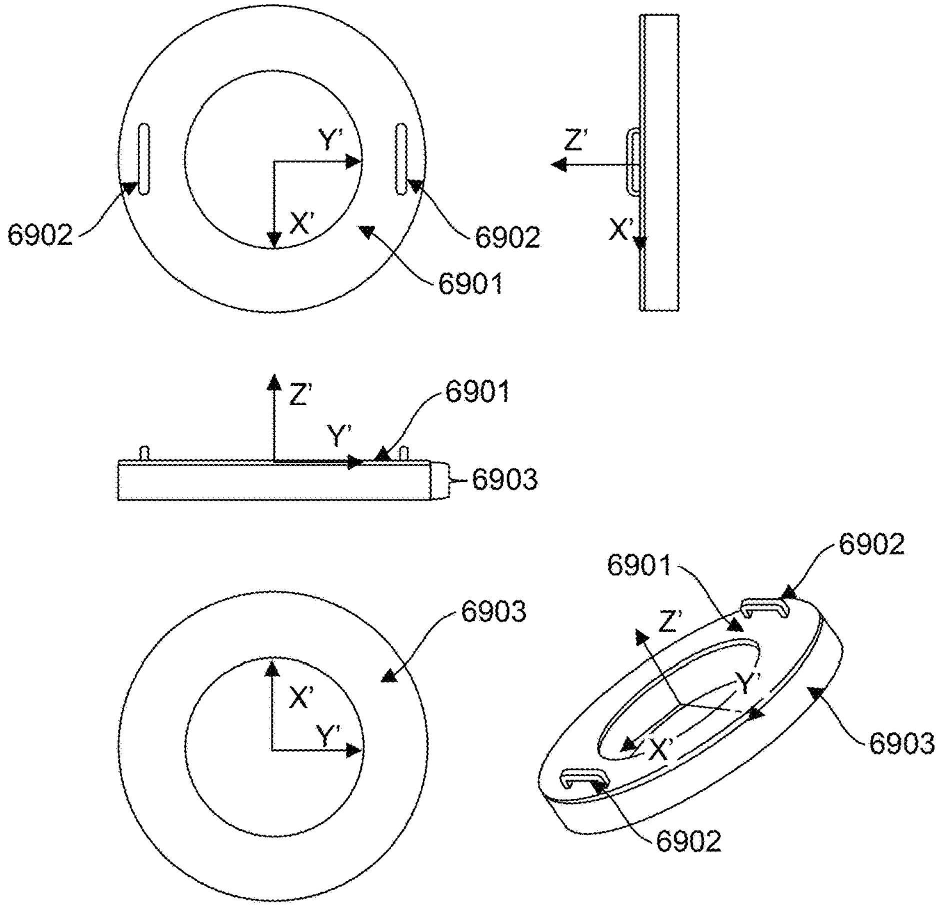
FIG. 69 illustrates a halo assembly.

The Halo head strap assembly shown in FIG. 68 includes the Halo, loop strap that threads through the Halo, and hook straps that attach to the head strap connector located on either side of the nasal respiratory device. Elements of the Halo assembly are shown in FIG. 69.

The nominally stiff reaction plate 6901 has both the left and right head strap connectors and head strap guides attached. At the opposite side to these elements is attached the Foam Compression Spring. The Reaction Plate spring stiffness in the Z direction, $K_{RP}$, is nominally >10× the spring stiffness of the Foam Compression Spring, K. Spring stiffness is defined as the ratio of applied Force in the Z direction required to achieve a resulting displacement in the Z direction. The left and right head strap connector 6902, attached to the top of the Reaction Plate, secure the left and right portions of the head strap when attached to the patient. The left and right head strap guides 6903 retain the associated left and right portion of the strap The strap is threaded through the corresponding opening of each guide. The Foam Compression Spring 6904 has a compressive stiffness, $K_F$, units are force per displacement, that results in a tensile load on the strap proportional to the level of compression, ΔZ, in the foam spring. This compression results in the reactive forces that secure and seal the nasal respiratory device to the nasal base of the patient. The Foam Compression Spring has a spring rate, $K_F$, that is lower than any other element impacting spring stiffness in the Z direction that influences the force reaction with the nasal respiratory apparatus head strap connector (Tie Point) to the strap by a factor of 10. Spring stiffness is defined as the ratio of applied Force in the Z direction required to achieve a resulting displacement in the Z direction.

The Halo head strap positioned on the patient as illustrated FIG. 68. View A-A shows the Halo assembly and the nasal respiratory apparatus being placed on the patient's head. The strap is then pulled in the Z direction relative to the Halo assembly tightening the strap and compressing the Foam Compression Spring. This compressing results in the force vectors on the Halo and nasal respiratory apparatus as illustrated, with the system secured to the patient. Features illustrated in FIG. 68 include the halo 6800, loop strap 6806, hook strap 6807 and connection 6808.

A hook and loop strap is utilized to secure the nasal respiratory device to the patient. FIG. 70 shows the loop strap threaded through the head strap guide of the Halo assembly. The hook straps snap onto the head strap connector located on either side of the nasal respiratory device. The loop strap is then pulled, compressing the Foam Spring of the Halo assembly, where the ends mate to the hook straps securing the nasal respiratory device to the patient. Note that the strap combinations could allow for hook and loop in the Halo and nasal respiratory device as shown or the hook strap could be attached to the Halo assembly and the loop strap attached to the nasal respiratory device. The straps could also be a configuration that utilize a buckle or snaps instead of hook and loop connectors.

Figure 71:
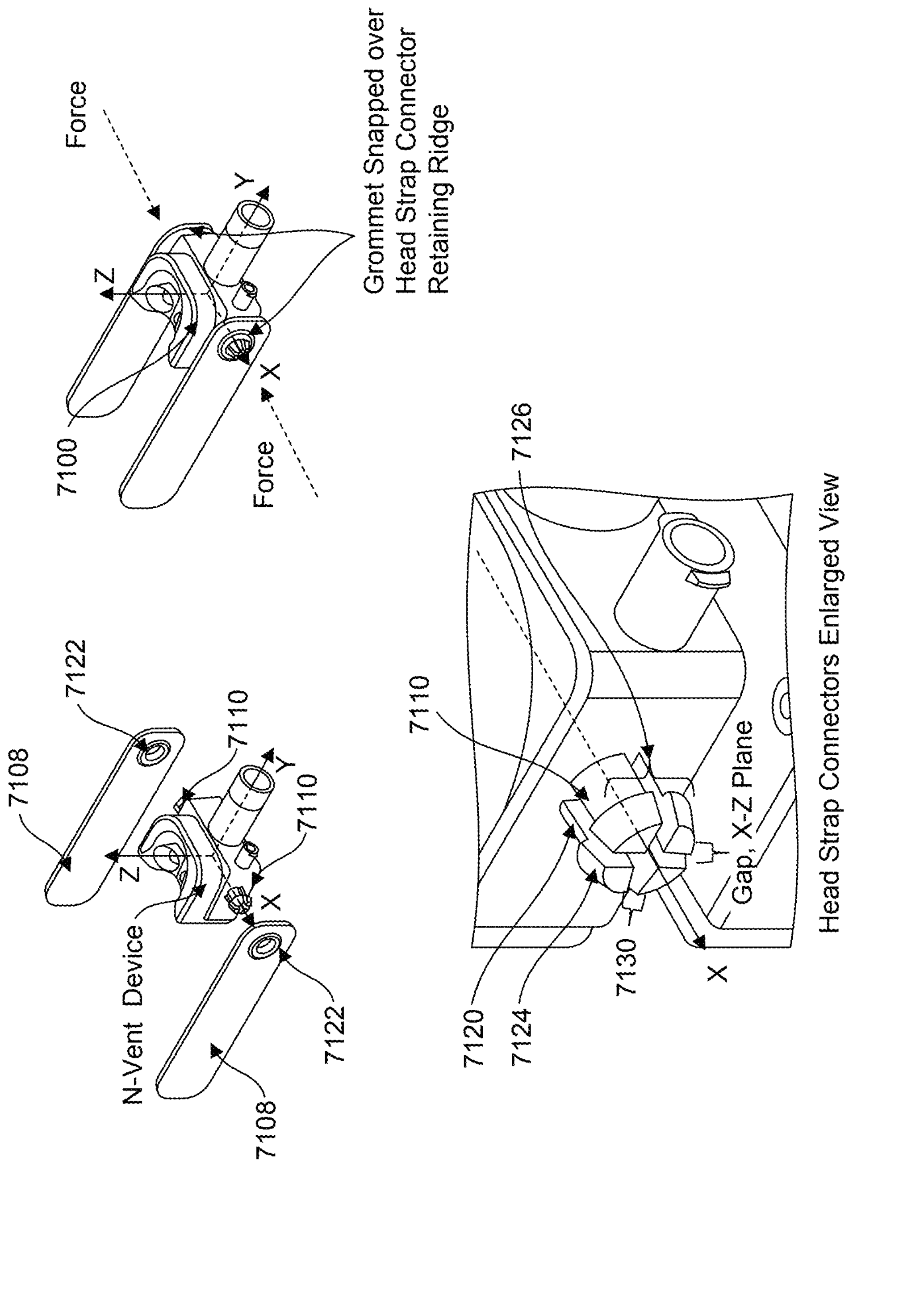
FIG. 71 illustrates a head strap connector.

Detail of how the strap connects to the nasal respiratory Device is shown in FIG. 71. In this configuration, the connector is a shaft that extends along the X-axis. The shaft is sliced with a gap in the X-Y and X-Z planes, resulting in radial compliance perpendicular to the X-axis. The connector has a ridge at the end of the shaft that has a diameter larger than the base diameter of the shaft. The Ridge has a chamfer that slopes towards the X-axis. The strap the is a flexible material with a reinforcing grommet. The strap could have a surface that is a hook or loop composition allowing for connection to the strap associated with the Halo assembly. Other features illustrated in FIG. 71 include strap 7108, Shaft base 7120, Grommet 7122, chamfer 7124, Grommet retaining ridge 7126, Head strap connector retaining ridge 7128, gap 7130 and Tie point 7110.

The interior diameter of the grommet 7122 is sized to allow for insertion over the base diameter of the head strap connector shaft 7120, but to have a diameter that is less than the maximum diameter of the Retaining Ridge 7126. The grommet 7122 is attached to the nasal respiratory device by applying a force along the X-axis that pushes against the chamfer 7124 of the Retaining Ridge 7126. This force is reacted by a radial force due to the chamfer 7124 that causes the head strap connector shaft 7120 to deflect towards the X-axis. The diameter of the ridge 7126 is less than the grommet 7122 when the shaft 7120 is compressed, and the grommet 7122 moves past the ridge 7126 along the X-axis. The Shaft 7120 then expands to its original position radially and the ridge 7126 retains the grommet 7122 on the shaft 7120.

Figure 72:
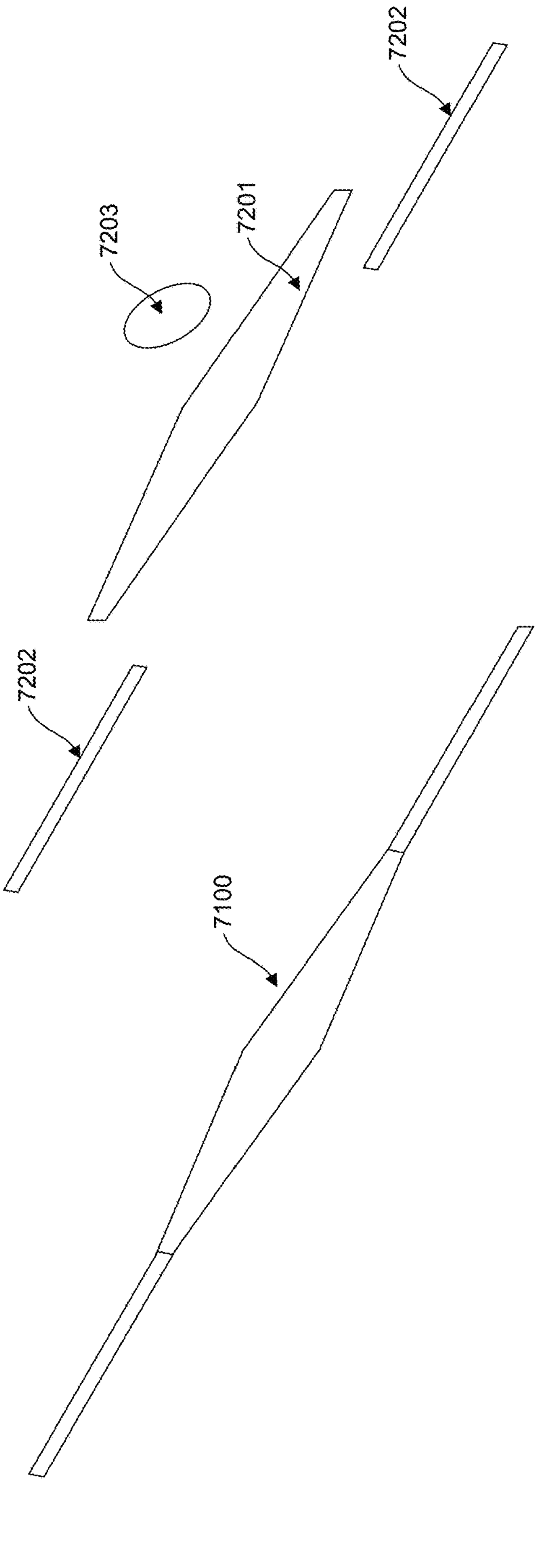
FIGS. 72-74 illustrates an elastic head strap assembly.
Figure 73:
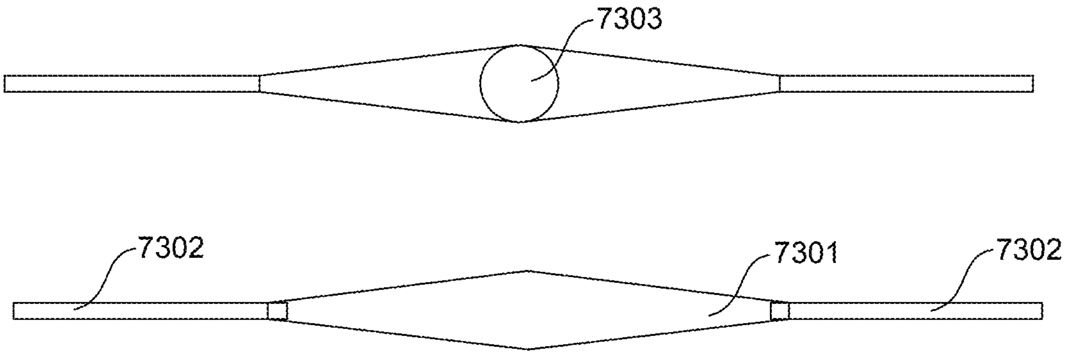
Figure 74:
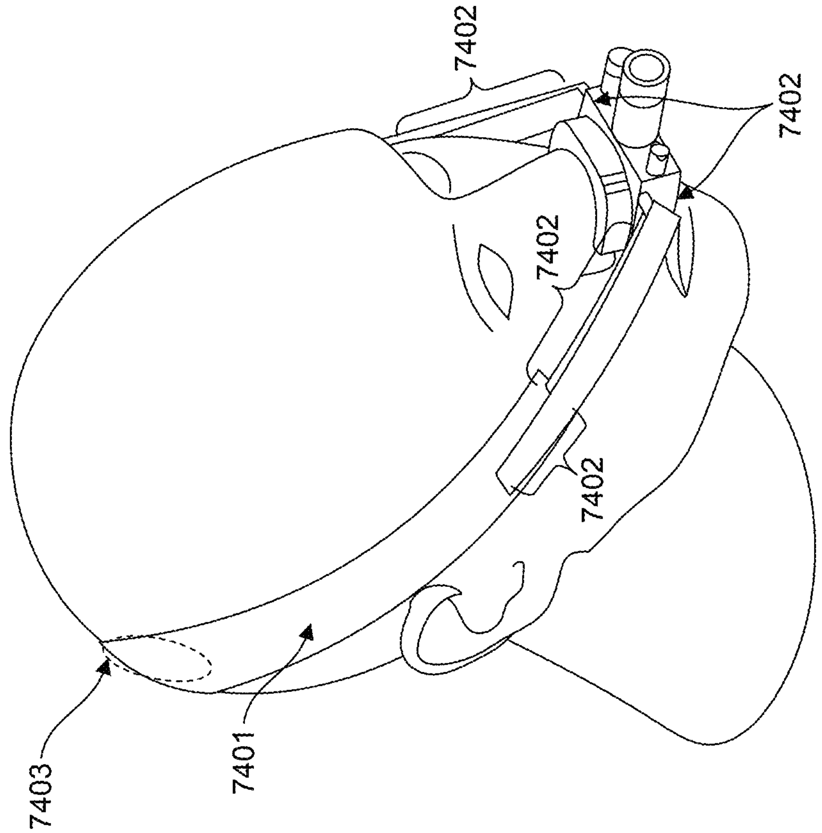

A head strap assembly illustrated in FIGS. 72-74 show a center elastic loop band providing compliance to the strap, two hook straps attached to either side of the elastic loop band, and an adhesive patch attached to the side of the elastic loop band opposite the loops. The adhesive side of the loop band is placed on the patients crown as shown in FIG. 75 then the hoop straps are threaded through the left and right strap connector of the N Vent assembly and the hook face of the hook strap is then attached to the loop face of the elastic loop band, securing the N Vent assembly to the patient.

In view of the features described above, using any of the devices or combination of features described above, a method of supplying a gas, such as oxygen, via a supply tube interfaces directly with one or both nares, requiring no sealed mask is possible. Also possible using any of the devices or combination of features described above is a method of ventilating a patient via a supply tube that interfaces directly with one or both nares, requiring no sealed mask. Also possible using any of the devices or combination of features described above with end tidal sampling is a method sampling $CO_2$ and other gases present in nasal end-tidal exhalation while ventilating a patient via a supply tube that interfaces directly with one or both nares, requiring no sealed mask. Also provided using any of the devices or combination of features described above with end tidal sampling is a method of sampling $CO_2$ and other gases present in oral end-tidal exhalation with an attachment connected to a supply tube that interfaces directly with one or both nares, requiring no sealed mask. Any of the nasal respiratory apparatus described above may include a bite block as described herein for intubation. Any of the nasal respiratory apparatus described above may include a High Flow gas supply with end tidal (ET) sampling. Any of the nasal respiratory apparatus described above may include a Supplementary Oxygen port for supplying $O_2$ to a patient. Providing any of the above steps may be via a supply that interfaces directly with one or both nares of a patient and includes a modular assembly for providing other functions such as end-tidal sampling and bite block for intubation.

The nasal respiratory apparatus described may include permutations and combinations of the following elements: A gas port connection provides interface with standard $O_2$ source, anesthesia machine, continuous positive airway pressure (CPAP) machine, hyper-inflation bag, high-flow source or ventilator (e.g., 8.5 mm, 11.5 mm, 15 mm or 22 mm conical connectors as defined by ISO 5356 or current equivalent standard). Other connector interfaces are possible. This port is designed to fit male or female connectors. A male connection interface is shown on this illustration. interfaces with multiple oxygenation and ventilation devices via the gas connection port, such as, but not limited to $O_2$ source with hyper-inflation bag, Anesthesia machine, Ventilator, and AMBU Bag, Continuous positive airway pressure (CPAP) machine, and High-flow $O_2$ source. Any of the embodiments described herein may include a gas supply tube allowing for transfer of gasses for oxygenation and ventilation, providing a structural interface with the air chamber, with or without a forehead standoff.

Any of the embodiments described herein may include an air chamber that provides the structural and gas flow interface between the gas supply tube, the nares ports and/or the end tidal sampling port. Two connection pins may be located on the −Z face of the appliance to attach to the bite block interface shelf and/or the oral end tidal (ET) attachment or other modular device desired. The connection pin may include a pin cap on top of a narrower pin.

Any of the embodiments described herein may include One or two nares ports provide the mechanical and gas flow interface between the nares and the nasal respiratory apparatus. The outer portion of the nares port provides a pressure seal in order to contain airflow between the nasal pharynx and the nasal respiratory apparatus. Nares ports may be based on the demographic statistics of the following parameters: Length of the major nares axis and/or; Length of the minor nares axis and/or; Angle of the Major axis and/or; Cross-sectional area of the nasal vestibule as a function of distance from the nasal respiratory apparatus-nares interface plane and the nasal valve plane. The nares ports may be a rigid air conduit covered by flexible ribs. The nares ports may be a rigid air conduit covered by flexible ribs having cross-section that varies in area as a function of distance from the nasal respiratory apparatus-nares interface plane and the nasal valve plane, for example, the cross section may be circular or elliptical or include an arc appropriately shaped for a patient's nares. Nares ports may be a rigid air conduit covered by flexible ribs having an elliptical cross-section that varies in area as a function of distance from the nasal respiratory apparatus-nares interface plane and the nasal valve plane. The nares ports may be a rigid air conduit covered by a balloon seal that inflates, sealing the region between the nares port and nasal vestibule wall when pressurized by a gas supply. The nares ports may be a rigid air conduit covered by a compliant annulus topped by a compliant truncated cone having a circular cross-section. The nares ports may be a rigid air conduit covered by compliant annulus topped by a compliant truncated cone having an elliptical cross-section. The nares points may be a rigid air conduit covered by a compliant truncated cone having a circular cross-section. The nares ports may be a rigid air conduit covered by a compliant truncated cone having an elliptical cross-section. The nares ports may be heat activated and expand with increasing temperatures in order to create a seal. The nares ports may have a smaller diameter and longer tube, which is movable and expandable and is inserted into the nares port. This tube within the nares port may be hollow or solid, extend beyond the soft palate, and used to provide a mechanical stent between the soft palate and retropharyngeal wall in order to relieve upper airway obstruction. If a hollow tube, it can also be used to suction secretions within the airway.

Any of the herein described embodiments of the nasal respiratory apparatus may include An portend tidal sample port allowing for sampling of the end tidal $CO_2$ and/or other gas levels from nasal exhalation by a sampling device such as a Capnography Sensor. The port exterior is a standard luer lock connector or other connector that interfaces with a sampling line per ISO 80396-7: 2016(E) or current equivalent. A male or female connector can be implemented, a female interface is shown in the illustration. Alternate interfaces can also exist.

Any of the embodiments described herein may include a forehead standoff is a cushioned mechanical interface between the nasal respiratory apparatus and the patient's forehead. Additionally, the forehead standoff provides space between the gas supply tube and forehead allowing various connectors to connect to the tube without interference from the forehead. A rail is an optional configuration where the rail is part of the gas supply tube. In this configuration, the forehead standoff is separate from the gas supply tube, constrained by the rail in the X and Y directions, but can slide along the Z-axis, allowing the forehead standoff to be centered on the forehead. This allows the nasal respiratory apparatus to accommodate a wide range of patient head sizes. The rail and gas supply tube can either be rigid, flexible, and/or expandable. Being expandable will accommodate for different size heads and allow the tubing to expand and retract as patients move head up and down, side to side, or rotate.

Any of the embodiments described herein may include *Columella-Philtrum* to nasal respiratory apparatus interface is a cushioned mechanical interface between the nasal respiratory apparatus and the patient.

Any of the embodiments described herein may include head strap connectors that provide mechanical tie points between the nasal respiratory apparatus and the head strap that secures the nasal respiratory apparatus to the patient's head. In one configuration, the head strap connector side view is nominally C shaped in order to clamp around the head strap cord once the cord is snapped in place. A strap configuration may secure the nasal respiratory apparatus with a strap around the left and right ear. A strap configuration may secure the nasal respiratory apparatus with a strap that passes above and below the left and right ear through a neck band. The tension of the straps can be adjusted by varying the strap length and then securing with a clamp.

Any of the embodiments described herein may include a supplementary $O_2$ port extending from the air chamber. The supplementary $O_2$ port interfaces with an oxygen supply line and allows for additional oxygen to be provided to the patient via a wall or other oxygen supply source.

Any of the embodiments described herein may include an optional oral end tidal attachment. The oral ET attachment is relatively rigid and clips onto the lower outer surface of the nasal respiratory apparatus air chamber. A flexible seal surrounds the perimeter of the oral Attachment and conforms to the perimeter of the mouth forming an air seal when the oral Attachment is secured to the air chamber. The device may include a gap in the flexible seal in order to allow flow from oral exhalation to exhaust to the atmosphere. The gap may be located near the portend tidal sample port, downstream, in order for gas to flow past the portend tidal sample port in order to be sampled. An interface shelf may include one or more pin openings and pin lock slots through the X'-Y' surface accept pins attached to the nasal respiratory apparatus. A pin opening may have pin opening diameter that is larger than the pin cap and allows the pins to be inserted into the openings. A pin lock slot where the pin portion of the connection pin slides down the pin lock slot with until it locks into place on the interface shelf may be provided.

An portend tidal sample port allowing for sampling of the end tidal $CO_2$ and/or other gas concentration levels from oral exhalation by a sampling device such as a Capnography Sensor. The port exterior is a standard luer lock connector or other connector that interfaces with a sampling line per ISO 80396-7: 2016(E) or current equivalent. Alternate interfaces can also exist. It is envisioned that in this configuration, the sample line from the oral ET attachment interfaces with one of two ports in a Y connector and then continues to the sensor through a single sample line.

Articulated nasal respiratory apparatus according to principles described herein may include a gas port connection to the interface with external gas supply and ventilation systems; a gas supply channel containing and allowing for the flow of gas between the gas connection port assembly and the air chamber assembly; gas connectors attach to this portion of the assembly. With the entrance port at the top of the channel. It will interface with a standard $O_2$ source, anesthesia machine, continuous positive airway pressure (CPAP) machine, hyper-inflation bag, high-flow source or ventilator 8.5 mm, 11.5 mm, 15 mm or 22 mm conical connectors as defined by ISO 5356 or current equivalent standard. Other connector interfaces are possible. This port is designed to interface with male or female connectors. The gas supply channel may terminate into a ball. Internal to the ball may be a channel for gas flow with a cross section of an L or elbow. gas flows out the exit port nominally at a 90° angle to the entrance flow direction. The ball interfaces with the socket portion of the air chamber assembly, creating a leak-free seal due to mechanical force conforming the ball surface to the socket surface. air flows between the gas port connection assembly and the air chamber assembly through the socket-chamber opening, part of the socket. Z-axis rotation retainer may be provided to keep the ball exit port within the boundary of the socket-chamber opening, required for gas flow. The Z-axis rotation retainer prevents the gas port connection assembly from rotating about the Z-axis of the gas supply channel. An entrance port may be provided at the top of the gas supply channel to interface with external gas supply and ventilation devices. An exit port, where gas flows from the gas port connection assembly to the air chamber assembly, or visa-versa, may be provided. A circular or oval-like perimeter of the opening can have the same radius as the socket, be slightly raised in order to accomplish a seal, or have a rubberized flexible consistency in order to support a seal between the socket and the ball. The articulated nasal respiratory apparatus may include an air chamber assembly to provide the structural and gas flow interface between the gas port connection assembly, nares ports and the end tidal sampling port. The air chamber may structurally support the nares ports, the end tidal sample port and is the gas flow channel between the ball opening and the nares ports. A socket may provide the mechanical support and sealing interface with the ball. An air dome may be included and contain gas flow from the atmosphere and provides a volumetric space for unhindered gas flow from the ball exit port, through the socket-chamber opening to the chamber. The device may include a Y-axis port slot on either side of the socket running parallel to the Z-axis and allows the gas port connection assembly to be rotated about the Y-axis +/−90° and may include an X-axis port slot allowing the gas port connection assembly to be rotated about the X-axis from 0° to approximately 20°. Note the articulated appliance may rotate approximately 20° about the X-axis for any Y-axis rotation from −90° to 90° or any other desired angle if the X-axis port slot is enlarged about the Y-axis to accommodate the additional range. The device may include a socket-chamber opening that is part of the socket and allows for gas to flow between the chamber and the ball through the air dome. A circular or oval-like perimeter of the opening can have the same radius as the socket, be slightly raised in order to accomplish a seal, or have a rubberized flexible consistency in order to support a seal between the socket and the ball. The device may include a *Columella-Philtrum* to articulated nasal respiratory apparatus interface, which is a cushioned mechanical interface between the articulated appliance and the patient. The device may include one or more nasal respiratory apparatus connection pins located on the −Z face of the articulated nasal respiratory apparatus attach to the bite block's nasal respiratory apparatus interface shelf or the oral end tidal (ET) attachment. The connection pin includes a pin cap on top of a narrower pin.

The articulated appliance may include one or two nares ports provide the mechanical and gas flow interface between the nares and the nasal respiratory apparatus. The outer portion of the nares port provides a pressure seal in order to contain airflow between the nasal pharynx and the nasal respiratory apparatus. Nares ports may be based on the demographic statistics of the following parameters: Length of the major nares axis and/or; Length of the minor nares axis and/or; Angle of the Major axis and/or; Cross-sectional area of the nasal vestibule as a function of distance from the nasal respiratory apparatus-nares interface plane and the nasal valve plane. The nares ports may be a rigid air conduit covered by flexible ribs. The nares ports may be a rigid air conduit covered by flexible ribs having cross-section that varies in area as a function of distance from the nasal respiratory apparatus-nares interface plane and the nasal valve plane, for example, the cross section may be circular or elliptical or include an arc appropriately shaped for a patient's nares. Nares ports may be a rigid air conduit covered by flexible ribs having an elliptical cross-section that varies in area as a function of distance from the nasal respiratory apparatus-nares interface plane and the nasal valve plane. The nares ports may be a rigid air conduit covered by a balloon seal that inflates, sealing the region between the nares port and nasal vestibule wall when pressurized by a gas supply. The nares ports may be a rigid air conduit covered by a compliant annulus topped by a compliant truncated cone having a circular cross-section. The nares ports may be a rigid air conduit covered by compliant annulus topped by a compliant truncated cone having an elliptical cross-section. The nares points may be a rigid air conduit covered by a compliant truncated cone having a circular cross-section. The nares ports may be a rigid air conduit covered by a compliant truncated cone having an elliptical cross-section. The nares ports may be heat activated and expand with increasing temperatures in order to create a seal. The nares ports may have a smaller diameter and longer tube, which is movable and expandable and is inserted into the nares port. This tube within the nares port may be hollow or solid, extend beyond the soft palate, and used to provide a mechanical stent between the soft palate and retropharyngeal wall in order to relieve upper airway obstruction. If a hollow tube, it can also be used to suction secretions within the airway.

The herein described embodiments of the articulated appliance may include an portend tidal sample port allowing for sampling of the end tidal $CO_2$ level from nasal exhalation by a sampling device such as a Capnography Sensor. The port exterior is a standard luer lock or other connector that interfaces with a sampling line per ISO 80396-7: 2016(E) or current equivalent. A male or female connector can be implemented, a female interface is shown in the illustration. Alternate interfaces can also exist. The herein described embodiments of the articulated appliance may include a supplementary $O_2$ port extends from the air chamber. It interfaces with an oxygen supply line and allows for additional oxygen to be provided to the patient via a wall or other oxygen supply source.

Any of the embodiments described herein may include an extension device for the nasal oxygenation and ventilation device, whether articulated or not, the extension device including a gas connection port entrance provides an interface with standard $O_2$ source, anesthesia machine, hyperinflation bag, high-flow source or ventilator 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. The extension device may include a gas supply tube is a conduit containing and allowing for the flow of gas between the gas connection port and the gas port connection assembly of the articulated nasal respiratory apparatus. The device may include a gas connection port exit to provide an interface with the gas supply channel. This port is designed to fit male or female connectors. A female connection interface is shown on this illustration. An embodiment including the extension device may include a forehead standoff, which is a cushioned mechanical interface between the nasal respiratory apparatus and the patient's forehead. Additionally, the forehead standoff provides space between the gas supply tube and forehead allowing various connectors to connect to the tube without interference from the forehead. A rail is an optional configuration where the rail is part of the gas supply tube. In this configuration, the forehead standoff is separate from the gas supply tube, constrained by the rail in the X and Y directions, but can slide along the Z-axis, allowing the forehead standoff to be centered on the forehead. This allows the nasal respiratory apparatus to accommodate a wide range of patient head sizes. Head strap connectors that provide mechanical tie points between the Extension device and/or the nasal respiratory apparatus. The head strap that secures the Extension device and/or the nasal respiratory apparatus to the patient's head. A configuration the head strap connector side view may nominally C shaped in order to clamp around the head strap cord once the cord is snapped in place. A strap configuration may secure the articulated nasal respiratory apparatus with a strap around the left and right ear. A strap configuration may secure the nasal respiratory apparatus and/or and the extension device with a strap around the left and right ear. A strap configuration may secure the nasal respiratory apparatus and/or and the extension device with a strap that passes above and below the left and right ear through a neck band. strap tension may can be adjusted by varying the strap length and then securing with a clamp. A strap configuration may secure the nasal respiratory apparatus and/or and the extension device with a strap over the left and right ear, connecting to an upper and lower head strap.

Any of the embodiments described herein may include an oral ET attachment that is relatively rigid and clips onto the lower outer surface of the articulated appliance's air chamber assembly. A flexible seal may surround the perimeter of the oral ET attachment and conforms to the perimeter of the mouth forming an air seal when the oral Attachment is secured to the air chamber. The device may include a gap in the flexible seal in order to allow flow from oral exhalation to exhaust to the atmosphere. The gap may be located near the portend tidal sample port (10), downstream, in order for gas to flow past the portend tidal sample port (10) in order to be sampled. The device may include an interface shelf; One or more pin openings and pin lock slots through the X'-Y' surface accept pins attached to the nasal respiratory apparatus; A pin opening where pin opening diameter is larger than the pin cap and allows the pins to be inserted into the openings; pin lock slot where the pin portion of the connection pin slides down the pin lock slot with until it locks into place on the interface shelf; and/or an portend tidal sample port allowing for sampling of the end tidal $CO_2$ level from oral exhalation by a sampling device such as a Capnography Sensor. The port exterior is a standard luer lock connector that interfaces with a sampling line per ISO 80396-7: 2016(E) or current equivalent. Alternate interfaces can also exist. It is envisioned that in this configuration, the sample line from the oral ET attachment interfaces with one of two ports in a Y connector and then continues to the sensor through a single sample line.

Any of the herein described embodiments, whether articulated or not, may include High Flow articulated nasal respiratory apparatus Configuration gas port connection is one of two assemblies making up the High Flow articulated nasal respiratory apparatus. It provides the interface with external gas supply and ventilation systems. A gas supply channel is a conduit containing and allowing for the flow of gas between the gas connection port assembly and the air chamber assembly. gas connectors attach to this portion of the assembly. With the entrance port at the top of the channel. It will interface with a high-flow Other connector interfaces are possible. This port is designed to interface with male or female connectors. The gas supply channel may termination terminating into a ball of an articulated embodiment. Internal to the ball is a channel for gas flow with a cross section of an L or elbow. gas flows out the exit port nominally at a 90° angle to the entrance flow direction. The ball interfaces with the socket portion of the air chamber assembly, creating a leak-free seal due to mechanical force conforming the ball surface to the socket surface. air flows between the gas port connection assembly and the air chamber assembly through the socket-chamber opening, part of the socket. The device may include a Z-axis rotation retainer that will keep the ball exit port within the boundary of the socket-chamber opening, required for gas flow, the Z-axis rotation retainer prevents the gas port connection assembly from rotating about the Z-axis of the gas supply channel. The device may include an entrance port at the top of the gas supply channel that interfaces with external gas supply and ventilation devices and/or An exit port, where gas flows from the gas port connection assembly to the air chamber assembly, or vice versa. The perimeter of the entrance could be slightly raised radially outward from the ball, have a rubber coating or a seal illustrated as an option in order to improve the gas seal against the socket interface where it rests. The device may include an air chamber assembly, which provides the structural and gas flow interface between the gas port connection assembly, the nares port, the High Flow nasal Cannula port and the end tidal sample port. The air chamber assembly may include a chamber that structurally supports the nares ports, the end tidal sample port and is the gas flow channel between the ball opening and the nares ports; a socket provides the mechanical support and sealing interface with the ball; an air dome contains gas flow from the atmosphere and provides a volumetric space for unhindered gas flow from the ball exit port, through the socket-chamber opening to the chamber; a Y-axis port slot on either side of the socket running parallel to the Z-axis and allows the gas port connection assembly to be rotated about the Y-axis +/−90°; an X-axis port slot allows the gas port connection assembly to be rotated about the X-axis from 0° to approximately 20°; a socket-chamber opening that is part of the socket and allows for gas to flow between the chamber and the ball through the air dome. An oval-like perimeter of the opening can have the same radius as the socket, be slightly raised in order to accomplish a seal, or have a rubberized flexible consistency in order to support a seal between the socket and the ball; and/or A *Columella-Philtrum* to articulated nasal respiratory apparatus interface, which is a cushioned mechanical interface between the articulated nasal respiratory apparatus and the patient.

The high flow embodiment may include or One nares port provide the mechanical and gas flow interface between the nares and the end-tidal port. The outer portion of the nares port provides a pressure seal in order to contain airflow between the nasal pharynx and the nasal respiratory apparatus. The nares ports design may be based on the demographic statistics of the following parameters: Length of the major nares axis And/or Length of the minor nares axis And/or Angle of the Major axis And/or Cross-sectional area of the nasal vestibule as a function of distance from the nasal respiratory apparatus-nares interface plane and the nasal valve plane. The nares port may include a rigid air conduit covered by flexible ribs. The nares port may include a rigid air conduit covered by flexible ribs having a circular cross-section that varies in area as a function of distance from the nasal respiratory apparatus-nares interface plane and the nasal valve plane. The nares port may include a rigid air conduit covered by flexible ribs having an elliptical cross-section that varies in area as a function of distance from the nasal respiratory apparatus-nares interface plane and the nasal valve plane. The nares port may include a rigid air conduit covered by a balloon seal that inflates, sealing the region between the nares port and nasal vestibule wall when pressurized by a gas supply. The nares port may include with a rigid air conduit covered by a compliant annulus topped by a compliant truncated cone having a circular cross-section. The nares port may include a rigid air conduit covered by compliant annulus topped by a compliant truncated cone having an elliptical cross-section. The nares port may include a rigid air conduit covered by a compliant truncated cone having a circular cross-section. The nares port may include a rigid air conduit covered by a compliant truncated cone having an elliptical cross-section. The “high flow” embodiment includes a High Flow nasal Cannula port to provide the mechanical and gas flow interface between the nares and gas flowing from the air chamber. The cannula port is not sealed against the nares wall and the pressure adjacent to the cannula is at atmospheric pressure. Any pressure due to the high gas flow is due to the static pressure associated with the gas flow rate.

The high flow embodiment may include an portend tidal sample port allowing for sampling of the end tidal $CO_2$ level from nasal exhalation by a sampling device such as a Capnography Sensor. The port exterior is a standard luer lock connector that interfaces with a sampling line per ISO 80396-7: 2016(E) or current equivalent. A male or female connector can be implemented, a female interface is shown in the illustration. Alternate interfaces can also exist. The high flow embodiment may further include a nares port-portend tidal sample port connector that provides a sealed gas flow path between the nares port and portend tidal sample port for gas entering the nares due to exhalation.

Any of the embodiments described herein may include A bite block that integrates with the nasal respiratory apparatus providing oral access are currently used for patients undergoing anesthesia when the option of using an intubation tube is desired. The bite block may include a bite block tube that provides the oral access along the Y-axis of the device and allows for breathing through the mouth. Inserted into the patient’s mouth, it provides the structural integrity for the device when clamped on by the patient’s teeth; an oral Access opening is the open region inside the bite block tube. It allows for gas flow during breathing as well as external access for placing an intubation tube or other device; and/or A bite block internal rim, located on the −Y face of the bite block tube, provides a dental catch that prevents the bite block device from slipping along the Y-axis when the teeth are closed around it. The rear oral access opening is at its nominal center; and/or A compliant tube cover wraps around the external side of the bite block tube along the Y-axis. It cushions the teeth when clamping the bite block. The bite block may further include a bite block Face is the structural element that interfaces to the +Y-axis of the BITE Block tube and the left and right head strap connectors. The front oral access opening is at its nominal center; and/or A $CO_2$ sample channel is an opening that runs through the wall of the bite block tube along the Y-axis. The entrance of the tube can exist either on the −Y face, and or the interior of the tube. The $CO_2$ sample channel terminates on the +Y face of the bite block tube where it interfaces with an portend tidal sample port. The purpose of the channel is to allow for sampling of exhaled $CO_2$ gas from the oral cavity. The bite block may further include an portend tidal sample port is an optional interface allowing for sampling of the end tidal $CO_2$ level from oral exhalation travelling through the $CO_2$ sample channel by a sampling device such as a Capnography Sensor. The port exterior is a standard luer lock connector that interfaces with a sampling line per ISO 80396-7: 2016(E) or current equivalent. A male or female connector can be implemented, a female interface is shown in the illustration. Alternate interfaces can also exist. The bite block may further include a head strap secures the bite block to the patient. An elastic strap that runs behind the patient's head and attaches to the right and left connector. A vertical slot parallel to the Z-axis is one location where the strap can loop through for attachment. The bite block may further include an interface shelf having one or more pin openings and pin lock slots through the X'-Y' surface accept pins attached to the nasal respiratory apparatus. The pin opening may have a pin opening diameter larger than the pin cap and allows the pins to be inserted into the openings. The device may include a pin lock slot where the pin portion of the connection pin slides down the pin lock slot with until it locks into place on the interface shelf.

A bite block may be included as part of an articulated embodiment of the herein described nasal respiratory apparatus to provide for patients undergoing anesthesia when the option of using an intubation tube is desired. The bite block may include a bite block tube that provides the oral access along the Y-axis of the device and allows for breathing through the mouth. Inserted into the patient's mouth, it provides the structural integrity for the device when clamped on by the patient's teeth; an oral Access opening is the open region inside the bite block tube and allows for gas flow during breathing as well as external access for placing an intubation tube or other device; and/or A bite block internal rim, located on the −Y face of the bite block tube, provides a dental catch that prevents the bite block device from slipping along the Y-axis when the teeth are closed around it and the rear oral access opening may be at its nominal center; and/or a compliant tube cover wraps around the external side of the bite block tube along the Y-axis. It cushions the teeth when clamping the bite block; and/or a bite block face that is the structural element that interfaces to the +Y-axis of the bite block tube and the left and right head strap connectors. The front oral access opening is at its nominal center; and/or a $CO_2$ sample channel, an opening that runs through the wall of the bite block tube along the Y-axis. The entrance of the tube can exist either on the −Y face, and or the interior of the tube. The $CO_2$ sample channel terminates on the +Y face of the bite block tube where it interfaces with an portend tidal sample port. The purpose of the channel is to allow for sampling of exhaled $CO_2$ gas from the oral cavity. The device may further include an portend tidal sample port is an optional interface allowing for sampling of the end tidal $CO_2$ level from oral exhalation travelling through the $CO_2$ sample channel by a sampling device such as a Capnography Sensor. The port exterior is a standard luer lock connector that interfaces with a sampling line per ISO 80396-7: 2016(E) or current equivalent. A male or female connector can be implemented, a female interface is shown in the illustration. Alternate interfaces can also exist. The device may further include a head strap secures the bite block to the patient. The head strap may include an elastic strap that runs behind the patient's head and attaches to the right and left connector. The device may further include a vertical slot parallel to the Z-axis is one location where the strap can loop through for attachment. The device may further include a nasal respiratory apparatus interface shelf. one or more pin openings and pin lock slots through the X'-Y' surface accept pins attached to the nasal respiratory apparatus. The pin opening may have a pin opening diameter larger than the pin cap and allows the pins to be inserted into the openings. The device may include a pin lock slot where the pin portion of the connection pin slides down the pin lock slot with until it locks into place on the interface shelf.

Any of the herein described embodiments, articulated or not, may include be included as a kit, wherein any of the herein described embodiments is included with an anesthesia circuit supporting the following functions: delivery of anesthetic gases and vapors; and/or oxygenation of the patient; and/or $CO_2$ elimination. The kit may include a Mapleson Circuit: (http://www.anaesthesia.med-.usyd.edu.au/resources/lectures/gas_supplies_clt/breathing-syste ms.html and https://www.ncbi.nlm.gov/pmc/articles/PMS3821268/) (e.g., Mapleson A, Mapleson B, Mapleson C, Mapleson D, Mapleson E (Jackson Rees modification), Mapleson F (Jackson Rees modification), Hyper-inflation bag circuit, etc.). The kit may further include Rebreathing circuits; and/or CO2 ABSORPTION (CIRCLE) CIRCUITS; and/or Bag-Mask ventilation systems (Ambu bag); and/or Lacks system; and/or Magills circuit; and/or Ayre's T-piece circuit; and/or Bain's modification of Mapleson D system; and/or Circuit for a Continuous Positive Airway Pressure (CPAP) system; and/or Circuit for a high-flow nasal ventilation System; and/or Circuit for a ventilator; and/or Capnography sampling systems; and/or Rebreathing circuits and the vaporizer location; and/or Circuit for a noninvasive ventilator/Bi-level positive airway pressure machine; and/or Kitted with supplemental oxygen tubing; and/or gas blender.

A method using any of the herein described embodiments may include a method of supplying a gas such as oxygen via a supply tube that interfaces directly with one or both nares, requiring no sealed mask; A method of ventilating a patient via a supply tube that interfaces directly with one or both nares, requiring no sealed mask; A method sampling $CO_2$ and other gases present in nasal end-tidal exhalation while ventilating a patient via a supply tube that interfaces directly with one or both nares, requiring no sealed mask; A method of sampling $CO_2$ and other gases present in oral end-tidal exhalation with an attachment connected to a supply tube that interfaces directly with one or both nares, requiring no sealed mask. The method may use any or all of the following features described herein, a bite block as described herein for intubation, High Flow gas supply with end tidal (ET) sampling; Supplementary Oxygen provided by the nasal respiratory apparatus; providing the above steps via a supply that interfaces directly with one or both nares of a patient and includes a modular assembly for providing other functions such as end-tidal sampling and bite block for intubation.

Any of the herein described embodiments or method may include methods or devices with gas port opening in a ±direction of the Z-axis. Any of the herein described embodiments or method may include methods or devices with end tidal sampling on any of one of or combination of port extending in the ±X, ±Y or ±Z-axis direction.

Any of the herein described embodiments, articulated or not articulated, may include an airtight seal about the nares and nares port allowing for pressurization of the nasal cavity relative to the atmosphere via air flow from the air chamber through the nares port, caused applying a compressive load nominally in the positive Z direction by the nasal respiratory apparatus through a nasal dam to the soft tissue in the nasal base nominally located in the X-Y plane. The device may also include the nasal dam having nominally the inverse Z surface geometry of the nasal base in the X-Y plane, allowing for a closer geometric interface, minimizing the deformation of the soft tissue and nasal dam required for sealing the nasal cavity. The nasal dam may comprise a low durometer material, substantially Shore A 10-100, that will allow for mutual conformance between the soft tissue of the nasal base and the appliance. One or more nares ports provide a gas pathway between the air chamber and the nasal cavity. The device may include one or more straps capable of providing tension, the straps attaching to one or more strap Tie Points resulting in a net positive force in the Z direction and/or a strap tension-tie point location/locations such that the forces and torques applied to the appliance by the strap tension are in equilibrium.

Any of the embodiments described herein may include a forehead standoff that interfaces with the patient and the nasal respiratory apparatus. The forehead standoff may comprise any or all of the following: a clamp and slot on the forehead standoff that interfaces with a rail that runs along the Z-axis of the gas supply tube; optionally including a slot that is sized to have a gap that is narrower than the rail causing the clamp to expand, resulting in a clamping force on the rail; and/or a rail that allows for forehead standoff travel along the Z-axis of the gas supply tube and prevents rotation about the Z-axis; and/or head straps that attach to one or more connectors on the forehead standoff; and/or head straps that attach to head strap connectors on the base of the air chamber.

Any of the embodiments described herein may include a forehead standoff that interfaces with the patient and the articulated nasal respiratory apparatus Extension, comprising any or all of the following: a clamp and slot on the forehead standoff that interfaces with a rail that runs along the Z-axis of the gas supply tube; optionally including a slot that is sized to have a gap that is narrower than the rail causing the clamp to expand, resulting in a clamping force on the rail; and/or a rail that allows for forehead standoff travel along the Z-axis of the gas supply tube and prevents rotation about the Z-axis; and/or head straps that attach to one or more connectors on the forehead standoff; and/or head straps that attach to head strap connectors on the base of the air chamber.

Method employing a nasal respiratory apparatus according to any of the embodiments described herein include a method of supplying a gas such as oxygen via a supply tube that interfaces directly with one or both nares, requiring no sealed mask; a method of ventilating a patient via a supply tube that interfaces directly with one or both nares, requiring no sealed mask; a method sampling $CO_2$ and other gases present in nasal end-tidal exhalation while ventilating a patient via a supply tube that interfaces directly with one or both nares, requiring no sealed mask; a method of sampling $CO_2$ and other gases present in oral end-tidal exhalation with an attachment connected to a supply tube that interfaces directly with one or both nares, requiring no sealed mask; and/or bite block as described herein for intubation; and/or High Flow gas supply with end tidal (ET) sampling; and/or Supplementary Oxygen provided by the nasal respiratory apparatus; and/or providing the above steps via a supply that interfaces directly with one or both nares of a patient and includes a modular assembly for providing other functions such as end-tidal sampling and bite block for intubation.

Any of the embodiments described herein may include an oral ventilation scoop located below the air chamber, near the mouth. It is substantially isolated from the air chamber from a gas pressure and flow perspective. It may be common to an oral portend tidal sample port. When gas is expelled from the mouth, a portion flows into the oral ventilation scoop to the oral portend tidal sample port and onto a gas monitoring device if it is connected by a sample line.

Any of the embodiments described herein may include And/or An portend tidal sample port allowing for sampling of the end tidal $CO_2$ and/or other gas levels from nasal exhalation by a sampling device such as a Capnography Sensor. The port exterior is a standard luer lock connector or other connector that interfaces with a sampling line per ISO 80396-7: 2016(E) or current equivalent. A male or female connector can be implemented, a female interface is shown in the illustration. Alternate interfaces can also exist. The end tidal sample port comprising a combined oral/nasal end tidal sample port (single or double nasal), and/or wherein the end tidal sample port is connected to a sample line attached to a gas monitoring device; and/or a supplemental $O_2$ port is provided as part of a ventilation scoop where the supply line from an $O_2$ source can be plugged into the $O_2$ port, providing gases orally, the ventilation scoop and supplemental $O_2$ port element including: A ventilation chamber having an opening near the patient's mouth and providing a channel to the oral opening to end tidal sample channel of the nasal respiratory device; a ventilation chamber to nasal respiratory apparatus oral opening is located on the chamber Top Wall of the ventilation chamber. It is coincident with the oral opening of the nasal respiratory device and allows exhaled gas to enter the oral opening of the nasal respiratory device; a supplemental $O_2$ chamber has an opening near the patient's mouth and allows for flow from the supplemental $O_2$ port to the patient who is breathing orally; a supplemental $O_2$ port is located on the chamber Front Wall of the supplemental $O_2$ chamber and connects to the supply line of an $O_2$ or air source; an $O_2$ port opening to $O_2$ chamber allows for gas flow between the supplemental $O_2$ port and the supplemental $O_2$ chamber; a chamber Separation Wall separates supplemental $O_2$ flow in the supplemental $O_2$ chamber and ventilation flow in the ventilation chamber. This is intended to minimize dilution of the exhaled gases that are sampled via the nasal/oral end tidal port of the nasal respiratory apparatus gas port Clip secures the ventilation scoop and supplemental $O_2$ port to the nasal respiratory device. This occurs when the nasal respiratory apparatus gas port Clip is forced onto the gas connection port of the nasal respiratory device in the Z direction and the opening of the clip separates in the X-Z plane. As it continues to move in the Z direction, it wraps around the gas connection port and is clipped to the port, securing it. The chamber Top Wall is then coincident with the bottom surface of the nasal respiratory device, preventing rotation about the Y-axis; a Push-Pull Tab allows the clinician to attach or detach the ventilation scoop and supplemental $O_2$ port to/from the nasal respiratory device. This is accomplished by pushing with a force in the Z direction to attach and pulling with a force in the −Z direction to detach; a chamber Outer Wall separates the supplemental $O_2$ chamber and ventilation chamber from the outside environment radially about the Y-axis in the −Z direction; a chamber Top Wall separates the supplemental $O_2$ chamber and ventilation chamber from the outside environment radially about the Y-axis in the Z direction. The exception is the ventilation chamber to nasal respiratory apparatus oral opening in the ventilation chamber; a chamber Front Wall separates the supplemental $O_2$ chamber and ventilation chamber from the outside environment axially in the Y direction; chamber opening(s) such that the supplemental $O_2$ chamber and ventilation chamber are open to the outside environment axially in the −Y direction, near the patient's mouth; and/or A *Columella-Philtrum* to nasal respiratory apparatus interface is a cushioned mechanical interface between the nasal respiratory apparatus and the patient; and/or head strap connectors (Tie Points) that provide mechanical tie points between the nasal respiratory apparatus and the head strap that secures the nasal respiratory apparatus to the patient's head; and/or A strap configuration that secures the nasal respiratory apparatus with a strap around the left and right ear; and/or A strap configuration that secures the nasal respiratory apparatus with a strap that passes above and below the left and right ear through a neck band; and/or A strap the tension of which can be adjusted by varying the strap length and then securing with a clamp; and/or A supplementary $O_2$ port extends from the air chamber. It interfaces with an oxygen supply line and allows for additional oxygen to be provided to the patient via a wall or other oxygen supply source.

Any of the embodiments described herein may include A head strap assembly for use with any of the above described systems, methods or devices, comprising a circular ring-shaped headpiece ("halo") and a strap, wherein the ring shaped headpiece comprises: a reaction plate, the reaction plate being normally stiff plate having the left and right head strap connectors and head strap guides attached. At the opposite side to these elements is attached the Foam Compression Spring. The Reaction Plate spring stiffness in the Z direction, $K_{RP}$, is nominally >10× the spring stiffness of the Foam Compression Spring, K. Spring stiffness is defined as the ratio of applied Force in the Z direction required to achieve a resulting displacement in the Z direction; The head strap connector attached to the top of the reaction plate and securing/holding left and right portions of the strap when attached to the patient; the head strap guides including left and right head strap guides retaining respective left and right portions of the strap wherein the strap is threaded through corresponding openings in each of the head strap guides; a foam compression spring having a compressive stiffness, $K_F$, units are force per displacement, that results in a tensile load on the strap proportional to the level of compression, $\Delta Z$, in the foam spring. This compression results in the reactive forces F1 and F2 illustrated in FIG. 67. The Foam Compression Spring has a spring rate, $K_F$, that is lower than any other element impacting spring stiffness in the Z direction that influences the force reaction with the nasal respiratory apparatus head strap connector (Tie Point) to the strap by a factor of 10. Spring stiffness is defined as the ratio of applied Force in the Z direction required to achieve a resulting displacement in the Z direction. The strap may comprise a thin rectangular sheet with multiple holes through the top surface as shown. The holes on the left and right end of the strap interface with the nasal respiratory apparatus strap connectors and the holes in the central portion of the strap interface with the strap connectors on the Halo assembly. The spring stiffness of the strap, $K_S$, is >10× that of the Foam Compression Spring stiffness, $K_F$. Spring stiffness is defined as the ratio of applied Force in the Z direction required to achieve a resulting displacement in the Z direction.

A method of using the head strap assembly as described herein, the method comprising: Placing the head strap assembly on the crown of a patient's head; Pulling the strap in a z direction relative to the reaction plate; Tightening the strap by pulling to compress the foam compression spring; securing the straps after compression of the foam compression spring.

Any of the embodiments described herein may include a head strap assembly, wherein the strap comprises: A hook and loop strap utilized to secure the nasal respiratory device to the patient, and/or wherein the loop strap is threaded through the head strap guide of the Halo assembly; and/or the spring stiffness of the strap, $K_S$, is >10× that of the Foam Compression Spring stiffness, $K_F$. Spring stiffness is defined as the ratio of applied Force in the Z direction required to achieve a resulting displacement in the Z direction; and/or the strap is elastically compliant; and/or the strap is substantially non-elastic.

Any of the methods or devices disclosed herein, wherein or further comprise: a nasal cushion, which may be an overmold on an external surface of the air chamber or nasal dam having nares ports; an air chamber, the chamber including an upper wall/boundary having nasal openings corresponding to nares ports of the nasal overmold or nasal dam, wherein the nasal openings are in fluid communication with the respective nares ports upon engagement with the nasal overmold or nasal dam; and/or the nasal dam and the air chamber engage via snap fit; and/or the snap fit is between the nares ports and the nasal openings; and/or the removable end cap including at least one fastening member for engaging with a complimentary fastening member of the air chamber.

Any of the methods or devices disclosed herein, wherein or further comprise: an oral ventilation scoop, comprising: a ventilation chamber for receiving orally exhaled gasses, the ventilation chamber optionally connected to an end tidal sample port; a supplemental Oxygen $O_2$ chamber for receiving a supplemental oxygen supply to be delivered orally to a patient; the ventilation chamber adjacent and spaced apart from the supplemental oxygen chamber such that a gap is formed between the supplemental Oxygen chambers to allow access to a patient's mouth for inserting and endoscope or other medical device to the patient's mouth; and/or a clip shaped to engage a gas connection port extending from an air chamber of the nasal respiratory apparatus device; and/or a nasal/oral portend tidal sample port parallel to the Y-axis is an optional interface allowing for sampling of the end tidal $CO_2$, etc. level from nasal exhalation by a sampling device such as a Capnography Sensor, an oxygen sensor, or gas analyzer. The port exterior is a standard luer lock connector that interfaces with a sampling line per ISO 80396-7: 2016(E) or current equivalent. A male or female connector can be implemented, a female interface is shown in the illustration. Alternate interfaces can also exist. Note the end tidal port can be on the plus or minus X-axis side of the air chamber. Note the end tidal port can be on the plus or minus X or Z-axis side of the air chamber. and/or an end tidal sample channel having an opening into the air chamber via the nasal opening to the end tidal sample channel and the oral scoop via the oral opening to the end tidal sample channel where it then terminates into/at the port opening; and/or an opening to the end tidal sample channel such that $CO_2$ exhaled nasal into the air chamber enters the end tidal sample channel via the nasal opening to the end tidal sample channel; and/or an oral opening to the end tidal sample channel such that $CO_2$ exhaled orally into the ventilation enters the end tidal sample channel via the ventilation; and/or a nasal dam surrounding the nares ports and interfaces with the soft tissue of the nasal base, providing a pressure seal in order to contain airflow between the nasal pharynx and the nasal respiratory apparatus; and/or head strap connectors providing mechanical tie points between the nasal respiratory apparatus and the head strap that secures the nasal respiratory apparatus to the patient's head;

and/or the ventilation chamber having an opening near the patient's mouth and providing a channel to end tidal sample channel of the nasal respiratory device; and/or a ventilation chamber to nasal respiratory apparatus oral opening located on the chamber Top Wall of the ventilation chamber. It is coincident with the oral opening of the nasal respiratory device and allows exhaled gas to enter the oral opening of the nasal respiratory device; and and/or a supplemental $O_2$ port located on a chamber Front Wall of the supplemental $O_2$ chamber and connected to the supply line of an $O_2$ or air source; and/or an $O_2$ port opening fluidically connected to the $O_2$ chamber to allow for gas flow between the supplemental $O_2$ port and the supplemental $O_2$ chamber.

Any of the ventilation mask assemblies and embodiments as described and claimed herein may be combined with a head strap assembly as follows in place of or in combination any previously disclosed head strap assembly.

Any of the embodiments described herein may include a head strap assembly having a center elastic loop band providing compliance to the strap, two hook straps attached to either side of the elastic loop band, and an adhesive patch attached to the side of the elastic loop band opposite the loops. The Adhesive side of the loop band is placed on the patients crown then the hoop straps are threaded through the left and right strap connector of the N Vent assembly and the hook face of the hook strap is then attached to the loop face of the elastic loop band, securing the N Vent assembly to the patient.

Any of the embodiments described herein may include a head strap assembly having an elastic band having a connector surface portion with at least one of a plurality of hooks and a plurality loops; and an adhesive patch having at least one adhesive surface, the adhesive patch coupled to a side of the elastic band opposite the connector surface portion; and wherein the adhesive surface of the adhesive patch is configured to be placed on a patient's crown; left and right straps, each of the left and right straps having a strap connector surface portion with a plurality of hoops or a plurality of loops complementary to the connector surface portion of the elastic band; and left and right strap connectors for coupling the straps to the ventilation mask (N Vent assembly).

Any of the above methods or devices disclosed herein, wherein or further comprising a method of applying a ventilation mask (N Vent assembly) to a patient via a strap assembly comprising an elastic band having a connector surface portion with at least one of a plurality of hooks and a plurality loops; and an adhesive patch having at least one adhesive surface, the adhesive patch coupled to a side of the elastic band opposite the connector surface portion; and Wherein the adhesive surface of the adhesive patch is configured to be placed on a patient's crown; left and right straps, each of the left and right straps having a strap connector surface portion with a plurality of hoops or a plurality of loops complementary to the connector surface portion of the elastic band; and Left and right strap connectors for coupling the straps to the ventilation mask (N Vent assembly), the method comprising: Applying the adhesive patch to the to the crown of the patient; threading the left and right straps through respective ones of the left and right strap connectors; attaching the connector surface portions of the left and right straps to the complementary connector surface portion of the elastic band, thereby securing the ventilation mask (N Vent assembly) to the patient.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A nasal respiratory apparatus comprising:

an air chamber having a gas connection port, first and second nasal conduits, a nasal end tidal sample port, and an isolation wall, wherein:

the gas connection port is configured to receive an externally supplied gas via a gas supply tube, the gas connection port being defined on a first wall of the air chamber;

the first and second nasal conduits are in fluid communication with the gas connection port via the air chamber;

the nasal end tidal sample port is defined on the first wall of the air chamber and is in fluid communication with both of the first nasal conduit and the second nasal conduit, the nasal end tidal sample port for receiving sample nasal gas from both the first nasal conduit and the second nasal conduit and the nasal end tidal sample port is for receiving sample nasal gas from one of a nasal conduit of the first and second nasal conduits and the nasal end tidal sample port configured to cause the sample nasal gas to exit the air chamber; and the isolation wall extends from the first wall of the air chamber toward an opposite and spaced apart wall of the air chamber, wherein the isolation wall is disposed between the gas connection port and the nasal end tidal sample port, wherein the isolation wall has a fixed end coupled to the first wall and a free end positioned within the air chamber, the free end being that is spaced apart from the first wall, the first and second nasal conduits, and the opposite and spaced apart wall of the air chamber, wherein a space between the free end and the nasal conduit that defines a flow path for the externally supplied gas to the first or the second nasal conduit during inhalation, and the isolation wall is configured to substantially prevent the externally supplied gas from entering the nasal end tidal sample port during exhalation.

2. The nasal respiratory apparatus of claim 1, wherein the air chamber comprises a removable end cap, the end cap comprising at least one wall of the air chamber.

3. The nasal respiratory apparatus of claim 1, wherein the air chamber is a substantially closed chamber except for the gas connection port, the first and second nasal conduits, and the nasal end tidal sample port.

4. The nasal respiratory apparatus of claim 1, wherein the gas supply tube extends from the gas connection port external to the air chamber, the gas supply tube parallel to one of an X-axis, Y-axis or Z-axis.

5. The nasal respiratory apparatus of claim 1, wherein a gas flow path when worn by a patient and connected to an external gas supply comprises:

inhaled gas flows from the external gas supply through the gas supply tube through the gas connection port into the air chamber and through the first and second nasal conduits to a patient's nares; and exhaled gas flows from the patient's nares through the first and second nasal conduits into the air chamber and through the gas connection port through the gas supply tube and through the first and second nasal conduits into the air chamber and to the nasal end tidal sample port.

6. The nasal respiratory apparatus of claim 5, wherein the exhaled gas passes through the nasal end tidal sample port to an external sample device.

7. The nasal respiratory apparatus of claim 1, further comprising connection pins extending from an external lower surface of the air chamber.

8. The nasal respiratory apparatus of claim 1, further comprising an oral end tidal scoop removably connected to the air chamber, the oral end tidal scoop having an oral end tidal sampling port.

9. The nasal respiratory apparatus of claim 8, wherein the oral end tidal scoop is fluidically isolated from the air chamber.

10. The nasal respiratory apparatus of claim 7, wherein an oral end tidal scoop is removably attached to the external lower surface of the air chamber via the connection pins.

11. The nasal respiratory apparatus of claim 1, further comprising a nasal cushion, the nasal cushion having at least one nare port therethrough in fluid communication with the first and second nasal conduits and the air chamber via the first and second nasal conduits.

12. The nasal respiratory apparatus of claim 11, wherein the nasal cushion comprises a nasal overmold to an external upper surface of the air chamber.

13. The nasal respiratory apparatus of claim 11, wherein the nasal cushion comprises a removable nasal dam corresponding to an external upper surface of the air chamber.

14. The nasal respiratory apparatus of claim 1, further comprising a head strap, the head strap connected to external side walls of the air chamber.

15. The nasal respiratory apparatus of claim 14, further comprising strap connectors on respective ones of the external side walls of the air chamber for connecting the head strap to the external side walls of the air chamber.

16. The nasal respiratory apparatus of claim 14, the head strap comprising a center elastic loop band and two hook straps, a first of the two hook straps attached to a first side of the elastic loop band and a second of the two hook straps attached to a second side of the elastic loop band.

17. The nasal respiratory apparatus of claim 1, wherein the air chamber is configured to establish an airtight seal between the nasal respiratory apparatus and the nares of a patient.

18. The nasal respiratory apparatus of claim 1, wherein the first and second nasal conduits are positioned adjacent the opposite and spaced apart wall of the air chamber.

19. The nasal respiratory apparatus of claim 1, wherein the isolation wall extends from the first wall towards the first and second nasal conduits, and wherein the gas connection port and the nasal end tidal sample port each extend from the first wall in the same direction.

* * * * *